(12) United States Patent
Burel

(10) Patent No.: US 10,745,756 B2
(45) Date of Patent: *Aug. 18, 2020

(54) METHODS OF PREDICTING TOXICITY

(71) Applicant: Ionis Pharmaceuticals, Inc., Carlsbad, CA (US)

(72) Inventor: Sebastien Burel, San Diego, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/659,378

(22) Filed: Jul. 25, 2017

(65) Prior Publication Data

US 2017/0327893 A1 Nov. 16, 2017

Related U.S. Application Data

(63) Continuation of application No. 14/932,018, filed on Nov. 4, 2015, now abandoned, which is a continuation of application No. 13/692,968, filed on Dec. 3, 2012, now Pat. No. 9,243,291.

(60) Provisional application No. 61/565,835, filed on Dec. 1, 2011.

(51) Int. Cl.
  C07H 21/04   (2006.01)
  C12Q 1/6883  (2018.01)
  C12Q 1/6876  (2018.01)

(52) U.S. Cl.
  CPC ......... *C12Q 1/6883* (2013.01); *C12Q 1/6876* (2013.01); *C12Q 2600/136* (2013.01); *C12Q 2600/142* (2013.01); *C12Q 2600/158* (2013.01); *C12Q 2600/16* (2013.01)

(58) Field of Classification Search
  None
  See application file for complete search history.

(56) References Cited

U.S. PATENT DOCUMENTS

| | | | | |
|---|---|---|---|---|
| 6,828,149 B2 * | 12/2004 | Freier | ............... | C12N 15/1137 435/325 |
| 2006/0063730 A1 * | 3/2006 | Monia | ................... | C12N 15/111 514/44 A |
| 2011/0118127 A1 * | 5/2011 | Ryu | .................... | C12Q 1/6883 506/7 |

OTHER PUBLICATIONS

Lee, Joseph H., et al. ("Examination of TOMM40, APOE, and PCDH11X in Caribbean Hispanics with late-onset Alzheimer's disease." Alzheimer's & Dementia: The Journal of the Alzheimer's Association 5.4 (2009): p. 472.).*

Li, Xu, et al. ("Levels of mTOR and its downstream targets 4E-BP1, eEF2, and eEF2 kinase in relationships with tau in Alzheimer's disease brain." The FEBS journal 272.16 (2005): 4211-4220), 2005.*

Keller, Lina, et al. ("The obesity related gene, FTO, interacts with APOE, and is associated with Alzheimer's disease risk: a prospective cohort study." Journal of Alzheimer's Disease 23.3 (2011): 461-469) 2011.*

Burel et al., "Hepatotoxicity of High Affinity Gapmer Antisense Oligonucleotides is Mediated by RNase H1 Dependent Promiscuous Reduction of Very Long Pre-mRNA Transcripts," Nucleic Acids Research, 2016, 44(5):2093-2109.

* cited by examiner

*Primary Examiner* — Kimberly Chong

(74) *Attorney, Agent, or Firm* — McNeill Naur PLLC

(57) ABSTRACT

Described herein are compounds useful for the treatment and investigation of diseases, methods for the prediction of in vivo toxicity of compounds useful for the treatment and investigation of diseases, and methods of discovering and identifying compounds useful for the treatment and investigation of diseases that have reduced in vivo toxicity.

18 Claims, No Drawings

Specification includes a Sequence Listing.

METHODS OF PREDICTING TOXICITY

SEQUENCE LISTING

The present application is being filed along with a Sequence Listing in electronic format. The Sequence Listing is provided as a file entitled CORE0101USC2SEQ_ST25.txt, created Nov. 3, 2015, which is 8 Kb in size. The information in the electronic format of the sequence listing is incorporated herein by reference in its entirety.

BACKGROUND

Oligonucleotides have been used in various biological and biochemical applications. They have been used as primers and probes for the polymerase chain reaction (PCR), as antisense agents used in target validation, drug discovery and development, as ribozymes, as aptamers, and as general stimulators of the immune system. Antisense compounds have been used to modulate target nucleic acids. Antisense compounds comprising a variety of chemical modifications and motifs have been reported. In certain instances, such compounds are useful as research tools, diagnostic reagents, and as therapeutic agents. In certain instances antisense compounds have been shown to modulate protein expression by binding to a target messenger RNA (mRNA) encoding the protein. In certain instances, such binding of an antisense compound to its target mRNA results in cleavage of the mRNA. Antisense compounds that modulate processing of a pre-mRNA have also been reported. Such antisense compounds alter splicing, interfere with polyadenlyation or prevent formation of the 5'-cap of a pre-mRNA. Certain antisense compounds have undesired toxixity. See e.g., Swayze et al., "Antisense oligonucleotides containing locked nucleic acid improve potency but cause significant hepatotoxicity in animals" Nucleic Acid Research (2007) 35(2):687-700.). This widespread use of antisense compounds and their vast potential as a potent therapeutic platform has led to an increased demand for rapid, inexpensive, and efficient methods to analyze and quantify the in vitro and in vivo properties of these compounds.

SUMMARY

The present disclosure provides the following non-limited numbered embodiments:

Embodiment 1

A method of predicting the in vivo toxicity of an oligomeric compound, wherein the method comprises:
contacting a cell in vitro with the oligomeric compound; and
measuring the modulation of the amount or activity of one or more off-target genes.

Embodiment 2

The method of embodiment 1, wherein the oligomeric compound comprises a gapmer oligonucleotide consisting of 10 to 30 linked nucleosides, wherein the gapmer oligonucleotide has a 5' wing region positioned at the 5' end of a deoxynucleotide gap, and a 3' wing region positioned at the 3' end of the deoxynucleotide gap.

Embodiment 3

The method of embodiment 2, wherein each of the wing regions is between about 1 to about 7 nucleotides in length.

Embodiment 4

The method of embodiment 2, wherein each of the wing regions is between about 1 to about 3 nucleotides in length.

Embodiment 5

The method of embodiment 2, wherein the deoxy gap region is between about 7 to about 18 nucleotides in length.

Embodiment 6

The method of embodiment 2, wherein the deoxy gap region is between about 11 to about 18 nucleotides in length.

Embodiment 7

The method of embodiment 2, wherein the deoxy gap region is between about 7 to about 10 nucleotides in length.

Embodiment 8

The method of any of embodiments 1 to 7, wherein the oligomeric compound comprises at least one modified nucleoside.

Embodiment 9

The method of embodiment 8, wherein the modified nucleoside is a bicylic modified nucleoside.

Embodiment 10

The method of embodiment 9, wherein the bicylic modified nucleoside is an LNA nucleoside.

Embodiment 11

The method embodiment 9, wherein the bicylic modified nucleoside is a 4'-$CH_2$—O-2' nucleoside.

Embodiment 12

The method embodiment 9, wherein the bicylic modified nucleoside is a 4'-$CH(CH_3)$—O-2' nucleoside.

Embodiment 13

The method of embodiment 8, wherein the modified nucleoside is a 2'-modified nucleoside.

Embodiment 14

The method of embodiment 12, wherein the 2'-modified nucleoside is substituted at the 2' position with a substituted or unsubstituted —O-alkyl or substituted or unsubstituted —O-(2-acetylamide), wherein the non-bicyclic 2'-modified nucleoside comprises a 2'-$OCH_3$, 2'-$O(CH_2)_2OCH_3$, or 2'-$OCH_2C(O)$—$NR_1R_2$, wherein $R_1$ and $R_2$ are independently hydrogen or substituted or unsubstituted alkyl or, in the alternative, are taken together to make a heterocyclic moiety.

Embodiment 15

The method of embodiment 1, wherein the oligomeric compound comprises a gapmer oligonucleotide consisting of 10 to 30 linked nucleosides wherein the gapmer oligonucleotide has a 5' wing region positioned at the 5' end of a deoxynucleotide gap, and a 3' wing region positioned at the 3' end of the deoxynucleotide gap, wherein at least one nucleoside of at least one of the wing regions is a 4' to 2' bicyclic nucleoside, and wherein at least one nucleoside of at least one of the wing regions is a non-bicyclic 2'-modified nucleoside.

Embodiment 16

The method of embodiment 15, wherein the 3' wing of the oligomeric compound comprises at least one 4' to 2' bicyclic nucleoside.

Embodiment 17

The method of any of embodiments 15 to 16, wherein the 5' wing of the oligomeric compound comprises at least one 4' to 2' bicyclic nucleoside.

Embodiment 18

The method of any of embodiments 15 to 16, wherein the 3' wing of the oligomeric compound comprises at least one non-bicyclic 2' modified nucleoside.

Embodiment 19

The method of any of embodiments 15 to 18, wherein the 5' wing of the oligomeric compound comprises at least one non-bicyclic 2'-modified nucleoside.

Embodiment 20

The method of embodiment 15, wherein the 3' wing of the oligomeric compound comprises at least three 4' to 2' bicyclic nucleosides.

Embodiment 21

The method of embodiment 15, wherein the 3' wing of the oligomeric compound comprises at least three non-bicyclic 2'-modified nucleosides.

Embodiment 22

The method of embodiment 15, wherein the 5' wing of the oligomeric compound comprises at least three 4' to 2' bicyclic nucleosides.

Embodiment 23

The method of embodiment 15, wherein the 5' wing of the oligomeric compound comprises at least three non-bicyclic 2'-modified nucleosides.

Embodiment 24

The method of embodiment 15, wherein the 5' wing of the oligomeric compound comprises at least three 4' to 2' bicyclic nucleosides, and wherein the 3' wing of the oligomeric compound comprises at least three non-bicyclic 2'-modified nucleosides.

Embodiment 25

The method of embodiment 15, wherein the 3' wing of the oligomeric compound comprises at least three 4' to 2' bicyclic nucleosides, and wherein the 5' wing of the oligomeric compound comprises at least three non-bicyclic 2'-modified nucleosides.

Embodiment 26

The method of any of embodiments 1 to 25, wherein the non-bicyclic 2'-modified nucleoside is substituted at the 2' position with a substituted or unsubstituted —O-alkyl or substituted or unsubstituted —O-(2-acetylamide), wherein the non-bicyclic 2'-modified nucleoside comprises a 2'-OCH$_3$, 2'-O(CH$_2$)$_2$OCH$_3$, or 2'-OCH$_2$C(O)—NR$_1$R$_2$, wherein R$_1$ and R$_2$ are independently hydrogen or substituted or unsubstituted alkyl or, in the alternative, are taken together to make a heterocyclic moiety.

Embodiment 27

The method of embodiment 26, wherein the non-bicyclic 2'-modified nucleoside is a 2'-O-methyl nucleoside.

Embodiment 28

The method of embodiment 26, wherein the non-bicyclic 2'-modified nucleoside is a 2'-O(CH$_2$)$_2$OCH$_3$.

Embodiment 29

The method of any of embodiments 1 to 28, wherein the oligomeric compound comprises at least one modified internucleoside linkage.

Embodiment 30

The method of any of embodiments 1 to 29, wherein at least one modified internucleoside linkage is a phosphorothioate linkage.

Embodiment 31

The method of any of embodiments 1 to 30, wherein the oligomeric compound comprises at least 3 phosphorothioate linkages.

Embodiment 32

The method of any of embodiments 1 to 31, wherein each internucleoside linkage in the oligomeric compound comprises a phosphorothioate linkage.

Embodiment 33

The oligomeric compound of any of embodiments 1 to 32, wherein each of the wing regions is between about 1 to about 7 nucleosides in length.

Embodiment 34

The oligomeric compound of any of embodiments 1 to 32, wherein each of the wing regions is between about 1 to about 3 nucleosides in length.

Embodiment 35

The method of any of embodiments 1 to 34, wherein the method of measuring modulation of the amount or activity of one or more off-target genes comprises measuring the increase in expression of one or more off-target genes and the reduction in expression of one or more off-target genes.

Embodiment 36

The method of any of embodiments 1 to 34, wherein the method of measuring modulation of the amount or activity of one or more off-target genes comprises measuring the increase in expression of one or more off-target genes.

Embodiment 37

The method of embodiment 1, wherein the method of measuring modulation of the amount or activity of one or more off-target genes comprises measuring the decrease in expression of one or more off-target genes.

Embodiment 38

The method of any of embodiments 1 to 37, wherein the off-target gene is a sentinel gene.

Embodiment 39

The method of any of embodiments 1 to 38, wherein at least one sentinel gene is selected from the group consisting of Fbxl17, Fto, Gphn, Cadps2, Bcas3, Msi2, BC057079, Chn2, Tbc1d22a, Macrod1, Iqgap2, Vps13b, Atg10, Fggy, Odz3, Vps53, Cgn11, RAPTOR, Ptprk, Vti1a, Ubac2, Fars2, Ppm11, Adk, 0610012H03Rik, Itpr2, Sec1512///Exoc6b, Atp9b, Atxn1, Adcy9, Mcph1, Ppp3ca, Bre, Dus41, Rassf1, Mdm2, Brp16, 0610010K14Rik, Rce1, Ilf2, Setd1a, and Gar1.

Embodiment 40

The method of any of embodiments 1 to 38, wherein at least two sentinel genes are selected from the group consisting of Fbxl17, Fto, Gphn, Cadps2, Bcas3, Msi2, BC057079, Chn2, Tbc1d22a, Macrod1, Iqgap2, Vps13b, Atg10, Fggy, Odz3, Vps53, Cgn11, RAPTOR, Ptprk, Vti1a, Ubac2, Fars2, Ppm11, Adk, 0610012H03Rik, Itpr2, Sec1512///Exoc6b, Atp9b, Atxn1, Adcy9, Mcph1, Ppp3ca, Bre, Dus41, Rassf1, Mdm2, Brp16, 0610010K14Rik, Rce1, Ilf2, Setd1a, and Gar1.

Embodiment 41

The method of any of embodiments 1 to 38, wherein at least three sentinel genes are selected from the group consisting of Fbxl17, Fto, Gphn, Cadps2, Bcas3, Msi2, BC057079, Chn2, Tbc1d22a, Macrod1, Iqgap2, Vps13b, Atg10, Fggy, Odz3, Vps53, Cgn11, RAPTOR, Ptprk, Vti1a, Ubac2, Fars2, Ppm11, Adk, 0610012H03Rik, Itpr2, Sec1512///Exoc6b, Atp9b, Atxn1, Adcy9, Mcph1, Ppp3ca, Bre, Dus41, Rassf1, Mdm2, Brp16, 0610010K14Rik, Rce1, Ilf2, Setd1a, and Gar1.

Embodiment 42

The method of any of embodiments 1 to 38, wherein at least four sentinel genes are selected from the group consisting of Fbxl17, Fto, Gphn, Cadps2, Bcas3, Msi2, BC057079, Chn2, Tbc1d22a, Macrod1, Iqgap2, Vps13b, Atg10, Fggy, Odz3, Vps53, Cgn11, RAPTOR, Ptprk, Vti1a, Ubac2, Fars2, Ppm11, Adk, 0610012H03Rik, Itpr2, Sec1512///Exoc6b, Atp9b, Atxn1, Adcy9, Mcph1, Ppp3ca, Bre, Dus41, Rassf1, Mdm2, Brp16, 0610010K14Rik, Rce1, Ilf2, Setd1a, and Gar1.

Embodiment 43

The method of any of embodiments 1 to 42, wherein one sentinel gene is Fbxl17.

Embodiment 44

The method of any of embodiments 1 to 43, wherein one sentinel gene is Fto.

Embodiment 45

The method of any of embodiments 1 to 44, wherein one sentinel gene is Gphn.

Embodiment 46

The method of any of embodiments 1 to 45, wherein one sentinel gene is Cadps2.

Embodiment 47

The method of any of embodiments 1 to 46, wherein one sentinel gene is Bcas3.

Embodiment 48

The method of any of embodiments 1 to 47, wherein one sentinel gene is Msi2.

Embodiment 49

The method of any of embodiments 1 to 48, wherein one sentinel gene is BC057079.

Embodiment 50

The method of any of embodiments 1 to 49, wherein one sentinel gene is Chn2.

Embodiment 51

The method of any of embodiments 1 to 50, wherein one sentinel gene is Tbc1d22a.

Embodiment 52

The method of any of embodiments 1 to 51, wherein one sentinel gene is Macrod1.

Embodiment 53

The method of any of embodiments 1 to 52, wherein one sentinel gene is Iqgap2.

Embodiment 54

The method of any of embodiments 1 to 53, wherein one sentinel gene is Vps13b.

Embodiment 55

The method of any of embodiments 1 to 54, wherein one sentinel gene is Atg10.

Embodiment 56

The method of any of embodiments 1 to 55, wherein one sentinel gene is Fggy.

Embodiment 57

The method of any of embodiments 1 to 56, wherein one sentinel gene is Odz3.

Embodiment 58

The method of any of embodiments 1 to 57, wherein one sentinel gene is Vps53.

Embodiment 59

The method of any of embodiments 1 to 58, wherein one sentinel gene is Cgn11.

Embodiment 60

The method of any of embodiments 1 to 59, wherein one sentinel gene is RAPTOR.

Embodiment 61

The method of any of embodiments 1 to 60, wherein one sentinel gene is Ptprk.

Embodiment 62

The method of any of embodiments 1 to 61, wherein one sentinel gene is Vti1a.

Embodiment 63

The method of any of embodiments 1 to 62, wherein one sentinel gene is Ubac2.

Embodiment 64

The method of any of embodiments 1 to 63, wherein one sentinel gene is Fars2.

Embodiment 65

The method of any of embodiments 1 to 64, wherein one sentinel gene is Ppm1l.

Embodiment 66

The method of any of embodiments 1 to 65, wherein one sentinel gene is Adk.

Embodiment 67

The method of any of embodiments 1 to 66, wherein one sentinel gene is 0610012H03Rik.

Embodiment 68

The method of any of embodiments 1 to 67, wherein one sentinel gene is Itpr2.

Embodiment 69

The method of any of embodiments 1 to 68, wherein one sentinel gene is Sec15l2///Exoc6b.

Embodiment 70

The method of any of embodiments 1 to 69, wherein one sentinel gene is Atp9b.

Embodiment 71

The method of any of embodiments 1 to 70, wherein one sentinel gene is Atxn1.

Embodiment 72

The method of any of embodiments 1 to 71, wherein one sentinel gene is Adcy9.

Embodiment 73

The method of any of embodiments 1 to 72, wherein one sentinel gene is Mcph1.

Embodiment 74

The method of any of embodiments 1 to 73, wherein one sentinel gene is Ppp3ca.

Embodiment 75

The method of any of embodiments 1 to 74, wherein one sentinel gene is Bre.

Embodiment 76

The method of any of embodiments 1 to 38, wherein the modulation of the amount or activity of Adcy9, Ptprk, Tbc1d22a, and Exoc6b is measured.

Embodiment 77

The method of any of embodiments 1 to 38, wherein the modulation of the amount or activity of Fbxl17, Fto, Gphn, and Cadps2 is measured.

Embodiment 78

The method of any of embodiments 1 to 38, wherein the modulation of the increase in expression of one or more of Dus41, Rassf1, Mdm2, Brp16, 0610010K14Rik, Rce1, Ilf2, Setd1a, and Gar1 is measured.

Embodiment 79

The method of any of embodiments 1 to 38, wherein the modulation of the amount or activity of one or more of ADK, FTO, IQGAP2, PPP3CA, PTPRK, and/or RAPTOR is measured.

Embodiment 80

The method of any of embodiments 1 to 38, wherein the modulation of the amount or activity of ADK and one or more of FTO, IQGAP2, PPP3CA, PTPRK, and/or RAPTOR is measured.

Embodiment 81

The method of any of embodiments 1 to 38, wherein the modulation of the amount or activity of FTO and one or more of ADK, IQGAP2, PPP3CA, PTPRK, and/or RAPTOR is measured.

Embodiment 82

The method of any of embodiments 1 to 38, wherein the modulation of the amount or activity of IQGAP2 and one or more of ADK, FTO, PPP3CA, PTPRK, and/or RAPTOR is measured.

Embodiment 83

The method of any of embodiments 1 to 38, wherein the modulation of the amount or activity of PPP3CA and one or more of ADK, FTO, IQGAP2, PTPRK, and/or RAPTOR is measured.

Embodiment 84

The method of any of embodiments 1 to 38, wherein the modulation of the amount or activity of PPP3CA and one or more of ADK, FTO, IQGAP2, PTPRK, and/or RAPTOR is measured.

Embodiment 85

The method of any of embodiments 1 to 38, wherein the modulation of the amount or activity of PTPRK and one or more of ADK, FTO, IQGAP2, PPP3CA, and/or RAPTOR is measured.

Embodiment 86

The method of any of embodiments 1 to 38, wherein the modulation of the amount or activity of RAPTOR and one or more of ADK, FTO, IQGAP2, PPP3CA, and/or PTPRK is measured.

Embodiment 87

The method of any of embodiments 1 to 38, wherein the down-regulated sentinel gene has a pre-mRNA length of greater than 176442 nucleobases.

Embodiment 88

The method of any of embodiments 1 to 38, wherein the down-regulated sentinel gene has a pre-mRNA length of greater than 19862 nucleobases.

Embodiment 89

The method of any of embodiments 1 to 38, wherein the up-regulated sentinel gene has a pre-mRNA length of less than 19862 nucleobases.

Embodiment 90

The method of any of embodiments 1 to 38, wherein the up-regulated sentinel gene has a pre-mRNA length of less than 7673 nucleobases.

Embodiment 91

The method of any of embodiments 1 to 38, wherein the down-regulated sentinel gene has an mRNA length of greater than 3962 nucleobases.

Embodiment 92

The method of any of embodiments 1 to 38, wherein the down-regulated sentinel gene has an mRNA length of greater than 2652 nucleobases.

Embodiment 93

The method of any of embodiments 1 to 38, wherein the up-regulated sentinel gene has an mRNA length of less than 2652 nucleobases.

Embodiment 94

The method of any of embodiments 1 to 38, wherein the up-regulated sentinel gene has an mRNA length of less than 1879 nucleobases.

Embodiment 95

The method of any of embodiments 1 to 94, wherein the predicted in vivo toxicity of the oligomeric compound is predicted by measurement of hepatotoxicity.

Embodiment 96

The method of any of embodiments 1 to 94, wherein the predicted in vivo toxicity of the oligomeric compound is predicted by a change in the amount of a liver enzyme.

Embodiment 97

The method of any of embodiments 1 to 94, wherein the predicted in vivo toxicity of the oligomeric compound is predicted by measurement of ALT.

Embodiment 98

The method of any of embodiments 1 to 94, wherein the predicted in vivo toxicity of the oligomeric compound is predicted by measurement of AST.

Embodiment 99

The method of any of embodiments 1 to 94, wherein the cell contacted with the oligomeric compound in vitro is a bEnd3 cell.

Embodiment 100

An oligomeric compound identified by the method of any of embodiments 1 to 99.

Embodiment 101

A method of administering the compound of embodiment 100 to an animal.

Embodiment 102

The in vitro method of determining the in vivo toxicity of any of embodiments 1 to 100, wherein the method comprises administering the oligomeric compound to an animal.

Embodiment 103

A method of determining the in vivo toxicity of an oligomeric compound, wherein the method comprises:
  contacting a cell with the oligomeric compound in vitro;
  measuring modulation of the amount or activity of one or more off-target genes;
  determining the in vivo toxicity of the oligomeric compound based on the level of amount or activity of the off-target genes; and
  administering the oligomeric compound to an animal.

Embodiment 104

The method of embodiment 103, wherein the off-target gene is a sentinel gene.

Embodiment 105

A method of predicting the in vivo or in vitro toxicity of an oligomeric compound, wherein the method comprises:
  setting a minimum amount of complementarity between the nucleobase sequence of the oligomeric compound and an off-target gene;
  determining the amount of complementarity between the sequence of the oligomeric compound and a group of one or more off-target genes in a genome;
  setting a minimum number of off-target genes that have an equal to or greater amount of complementarity between the sequence of the oligomeric compound and a group of one or more off-target genes; and
  determining the number of off-target genes in a genome that have an equal to or greater amount of complementarity between the sequence of the oligomeric compound and a group of one or more off-target genes.

Embodiment 106

The method of embodiment 105, wherein a computer is used to determine the amount of complementarity between the sequence of the oligomeric compound and a group of one or more off-target genes.

Embodiment 107

The method of any one of embodiments 105 to 106, wherein a computer is used to determine the number of off-target genes that have an equal to or greater amount of complementarity between the sequence of the oligomeric compound and a group of one or more off-target genes.

Embodiment 108

The method of any one of embodiments 105 to 107, wherein the amount of complementarity is a measure of the number of consecutive complementary nucleobases between the oligomeric compound and a group of one or more off-target genes.

Embodiment 109

The method of any one of embodiments 105 to 108, wherein each off-target gene is a sentinel gene.

Embodiment 110

A method of identifying a sentinel gene, wherein the method comprises:
  administering a compound to an animal;
  assessing the toxicity of the compound at a timepoint after administration of the compound; measuring the degree of modulation of one or more one off-target genes;
  calculating the correlation between the degree of off-target gene modulation and toxicity; identifying any off-target genes having a coefficient of determination greater than 0.

Embodiment 111

The method of embodiment 110, wherein the coefficient of determination is greater than 0.5.

Embodiment 112

The method of embodiment 110, wherein the coefficient of determination is greater than 0.6.

Embodiment 113

The method of embodiment 110, wherein the coefficient of determination is greater than 0.7.

Embodiment 114

The method of embodiment 110, wherein the coefficient of determination is greater than 0.8.

Embodiment 115

The method of embodiment 110, wherein the coefficient of determination is greater than 0.9.

Embodiment 116

The method of embodiment any of embodiments 110 to 115, wherein the toxicity is assessed 24 hours after administration of the compound.

Embodiment 117

The method of any of embodiments 110 to 115, wherein the toxicity is assessed 48 hours after administration of the compound.

Embodiment 118

The method of any of embodiments 110 to 116, wherein the degree of modulation of one or more one off-target genes is greater than one-fold.

Embodiment 119

The method of any of embodiments 110 to 116, wherein the degree of modulation of one or more one off-target genes is greater than two-fold.

Embodiment 120

A method of predicting in vivo toxicity of an oligonucleotide comprising comparing the nucleobase sequence of the oligonucleotide to the nucleobase sequence of at least one sentinel gene transcript;
  determining whether the oligonucleotide is complementary to any regions of the the at least one sentinel gene transcript;
  predicting whether the oligonucleotide will hybridize to the sentinel gene transcript under physiologically relevant conditions; and
  predicting toxicity based on the prediction of hybridization.

Embodiment 121

A method of identifying at least one antisense compound that is predicted not to be toxic in vivo comprising:
  identifying a set of potential antisense compounds, each having a nucleobase sequence complementary to a target nucleic acid;
  comparing the nucleobase sequence of each potential antisense compound to the nucleobase sequence of at least one sentinel gene transcript;
  identifying potential antisense compounds having a nucleobase sequence complementary to at least one sentinel gene transcript as predicted toxic antisense compounds;
  removing the predicted toxic compounds from the set of potential antisense compounds;
  identifying one or more of the remaining potential antisense compounds as predicted not to be toxic in vivo.

Embodiment 122

The method of embodiment 120 or 121, wherein the predicted toxic compounds are 100% complementary to at least one sentinel gene transcript.

Embodiment 123

The method of embodiment 122, wherein the predicted toxic compounds have not more than one mismatch relative to at least one sentinel gene transcript.

Embodiment 124

The method of embodiment 122, wherein the predicted toxic compounds have not more than two mismatches relative to at least one sentinel gene transcript.

Embodiment 125

The method of embodiment 120 or 121, wherein each potential antisense compound is compared to the nucleobase sequence of at least two sentinel gene transcripts.

Embodiment 126

The method of embodiment 120 or 121, wherein each potential antisense compound is compared to the nucleobase sequence of at least three sentinel gene transcripts.

Embodiment 127

The method of any of embodiments 120 to 126, wherein at least one sentinel gene is selected from the group consisting of Fbxl17, Fto, Gphn, Cadps2, Bcas3, Msi2, BC057079, Chn2, Tbc1d22a, Macrod1, Iqgap2, Vps13b, Atg10, Fggy, Odz3, Vps53, Cgn11, RAPTOR, Ptprk, Vti1a, Ubac2, Fars2, Ppm1l, Adk, 0610012H03Rik, Itpr2, Sec1512///Exoc6b, Atp9b, Atxn1, Adcy9, Mcph1, Ppp3ca, Bre, Dus41, Rassf1, Mdm2, Brp16, 0610010K14Rik, Rce1, Ilf2, Setd1a, and Gar1.

Embodiment 128

The method of any of embodiments 1 to 127 comprising making at least one antisense compound that is predicted not to be toxic in vivo and testing it in an animal.

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference in their entirety for any purpose.

A. Definitions

Unless specific definitions are provided, the nomenclature used in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., 21$^{st}$ edition, 2005; and "Antisense Drug Technology, Principles, Strategies, and Applications" Edited by Stanley T. Crooke, CRC Press, Boca Raton, Fla.; and Sambrook et al., "Molecular Cloning, A laboratory Manual," 2$^{nd}$ Edition, Cold Spring Harbor Laboratory Press, 1989, which are hereby incorporated by reference for any purpose. Where permitted, all patents, applications, published applications and other publications and other data referred to throughout in the disclosure are incorporated by reference herein in their entirety.

Unless otherwise indicated, the following terms have the following meanings:

As used herein, "nucleoside" means a compound comprising a nucleobase moiety and a sugar moiety. Nucleosides include, but are not limited to, naturally occurring nucleosides (as found in DNA and RNA) and modified nucleosides. Nucleosides may be linked to a phosphate moiety.

As used herein, "chemical modification" means a chemical difference in a compound when compared to a naturally occurring counterpart. Chemical modifications of oligonucleotides include nucleoside modifications (including sugar moiety modifications and nucleobase modifications) and internucleoside linkage modifications. In reference to an oligonucleotide, chemical modification does not include differences only in nucleobase sequence.

As used herein, "furanosyl" means a structure comprising a 5-membered ring comprising four carbon atoms and one oxygen atom.

As used herein, "naturally occurring sugar moiety" means a ribofuranosyl as found in naturally occurring RNA or a deoxyribofuranosyl as found in naturally occurring DNA.

As used herein, "sugar moiety" means a naturally occurring sugar moiety or a modified sugar moiety of a nucleoside.

As used herein, "modified sugar moiety" means a substituted sugar moiety or a sugar surrogate.

As used herein, "substituted sugar moiety" means a furanosyl that is not a naturally occurring sugar moiety. Substituted sugar moieties include, but are not limited to furanosyls comprising substituents at the 2'-position, the 3'-position, the 5'-position and/or the 4'-position. Certain substituted sugar moieties are bicyclic sugar moieties.

As used herein, "2'-substituted sugar moiety" means a furanosyl comprising a substituent at the 2'-position other than H or OH. Unless otherwise indicated, a 2'-substituted sugar moiety is not a bicyclic sugar moiety (i.e., the 2'-substituent of a 2'-substituted sugar moiety does not form a bridge to another atom of the furanosyl ring.

As used herein, "MOE" means —OCH$_2$CH$_2$OCH$_3$.

As used herein, "2'-F nucleoside" refers to a nucleoside comprising a sugar comprising fluoroine at the 2' position. Unless otherwise indicated, the fluorine in a 2'-F nucleoside is in the ribo position (replacing the OH of a natural ribose).

As used herein, "2'-(ara)-F" refers to a 2'-F substituted nucleoside, wherein the fluoro group is in the arabino position.

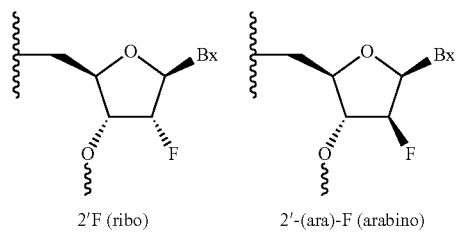

2'F (ribo)    2'-(ara)-F (arabino)

As used herein the term "sugar surrogate" means a structure that does not comprise a furanosyl and that is capable of replacing the naturally occurring sugar moiety of a nucleoside, such that the resulting nucleoside sub-units are capable of linking together and/or linking to other nucleosides to form an oligomeric compound which is capable of hybridizing to a complementary oligomeric compound. Such structures include rings comprising a different number of atoms than furanosyl (e.g., 4, 6, or 7-membered rings); replacement of the oxygen of a furanosyl with a non-oxygen atom (e.g., carbon, sulfur, or nitrogen); or both a change in the number of atoms and a replacement of the oxygen. Such structures may also comprise substitutions corresponding to those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholinos, cyclohexenyls and cyclohexitols.

As used herein, "bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl.

As used herein, "nucleotide" means a nucleoside further comprising a phosphate linking group. As used herein, "linked nucleosides" may or may not be linked by phosphate linkages and thus includes, but is not limited to "linked nucleotides." As used herein, "linked nucleosides" are nucleosides that are connected in a continuous sequence (i.e. no additional nucleosides are present between those that are linked).

As used herein, "nucleobase" means a group of atoms that can be linked to a sugar moiety to create a nucleoside that is capable of incorporation into an oligonucleotide, and wherein the group of atoms is capable of bonding with a complementary naturally occurring nucleobase of another oligonucleotide or nucleic acid. Nucleobases may be naturally occurring or may be modified.

As used herein the terms, "unmodified nucleobase" or "naturally occurring nucleobase" means the naturally occurring heterocyclic nucleobases of RNA or DNA: the purine bases adenine (A) and guanine (G), and the pyrimidine bases thymine (T), cytosine (C) (including 5-methyl C), and uracil (U).

As used herein, "modified nucleobase" means any nucleobase that is not a naturally occurring nucleobase.

As used herein, "modified nucleoside" means a nucleoside comprising at least one chemical modification compared to naturally occurring RNA or DNA nucleosides. Modified nucleosides comprise a modified sugar moiety and/or a modified nucleobase.

As used herein, "bicyclic nucleoside" or "BNA" means a nucleoside comprising a bicyclic sugar moiety.

As used herein, "constrained ethyl nucleoside" or "cEt" means a nucleoside comprising a bicyclic sugar moiety comprising a 4'-CH(CH$_3$)—O-2'bridge.

As used herein, "locked nucleic acid nucleoside" or "LNA" means a nucleoside comprising a bicyclic sugar moiety comprising a 4'-CH$_2$—O-2'bridge.

As used herein, "2'-substituted nucleoside" means a nucleoside comprising a substituent at the 2'-position other than H or OH. Unless otherwise indicated, a 2'-substituted nucleoside is not a bicyclic nucleoside.

As used herein, "2'-deoxynucleoside" means a nucleoside comprising 2'-H furanosyl sugar moiety, as found in naturally occurring deoxyribonucleosides (DNA). In certain embodiments, a 2'-deoxynucleoside may comprise a modified nucleobase or may comprise an RNA nucleobase (e.g., uracil).

As used herein, "RNA-like nucleoside" means a modified nucleoside that adopts a northern configuration and functions like RNA when incorporated into an oligonucleotide. RNA-like nucleosides include, but are not limited to 3'-endo furanosyl nucleosides and RNA surrogates.

As used herein, "3'-endo-furanosyl nucleoside" means an RNA-like nucleoside that comprises a substituted sugar moiety that has a 3'-endo conformation. 3'-endo-furanosyl nucleosides include, but are not limited to: 2'-MOE, 2'-F, 2'-OMe, LNA, ENA, and cEt nucleosides.

As used herein, "RNA-surrogate nucleoside" means an RNA-like nucleoside that does not comprise a furanosyl. RNA-surrogate nucleosides include, but are not limited to hexitols and cyclopentanes.

As used herein, "oligonucleotide" means a compound comprising a plurality of linked nucleosides. In certain embodiments, an oligonucleotide comprises one or more unmodified ribonucleosides (RNA) and/or unmodified deoxyribonucleosides (DNA) and/or one or more modified nucleosides.

As used herein "oligonucleoside" means an oligonucleotide in which none of the internucleoside linkages contains a phosphorus atom. As used herein, oligonucleotides include oligonucleosides.

As used herein, "modified oligonucleotide" means an oligonucleotide comprising at least one modified nucleoside and/or at least one modified internucleoside linkage.

As used herein "internucleoside linkage" means a covalent linkage between adjacent nucleosides in an oligonucleotide.

As used herein "naturally occurring internucleoside linkage" means a 3' to 5' phosphodiester linkage.

As used herein, "modified internucleoside linkage" means any internucleoside linkage other than a naturally occurring internucleoside linkage.

As used herein, "oligomeric compound" means a polymeric structure comprising two or more sub-structures. In certain embodiments, an oligomeric compound comprises an oligonucleotide. In certain embodiments, an oligomeric compound comprises one or more conjugate groups and/or terminal groups. In certain embodiments, an oligomeric compound consists of an oligonucleotide.

As used herein, "terminal group" means one or more atom attached to either, or both, the 3' end or the 5' end of an oligonucleotide. In certain embodiments a terminal group is a conjugate group. In certain embodiments, a terminal group comprises one or more terminal group nucleosides.

As used herein, "conjugate" means an atom or group of atoms bound to an oligonucleotide or oligomeric compound. In general, conjugate groups modify one or more properties of the compound to which they are attached, including, but not limited to pharmacodynamic, pharmacokinetic, binding, absorption, cellular distribution, cellular uptake, charge and/or clearance properties.

As used herein, "conjugate linking group" means any atom or group of atoms used to attach a conjugate to an oligonucleotide or oligomeric compound.

As used herein, "antisense compound" means a compound comprising or consisting of an oligonucleotide at least a portion of which is complementary to a target nucleic acid to which it is capable of hybridizing, resulting in at least one antisense activity.

As used herein, "antisense activity" means any detectable and/or measurable change attributable to the hybridization of an antisense compound to its target nucleic acid.

As used herein, "detecting" or "measuring" means that a test or assay for detecting or measuring is performed. Such detection and/or measuring may result in a value of zero. Thus, if a test for detection or measuring results in a finding of no activity (activity of zero), the step of detecting or measuring the activity has nevertheless been performed.

As used herein, "detectable and/or measurable activity" means a statistically significant activity that is not zero.

As used herein, "essentially unchanged" means little or no change in a particular parameter, particularly relative to another parameter which changes much more. In certain embodiments, a parameter is essentially unchanged when it changes less than 5%. In certain embodiments, a parameter is essentially unchanged if it changes less than two-fold while another parameter changes at least ten-fold. For example, in certain embodiments, an antisense activity is a change in the amount of a target nucleic acid. In certain such embodiments, the amount of a non-target nucleic acid is essentially unchanged if it changes much less than the target nucleic acid does, but the change need not be zero.

As used herein, "expression" means the process by which a gene ultimately results in a protein. Expression includes, but is not limited to, transcription, post-transcriptional modification (e.g., splicing, polyadenlyation, addition of 5'-cap), and translation.

As used herein, "modulation" means a change of amount, activity, or quality when compared to the amount, activity, or quality prior to modulation. For example, "modulation" of a nucleic acid includes any change in the amount or activity of the nucleic acid. In certain embodiments, modulation of a nucleic acid is assessed by comparing the amount and/or activity of the nucleic acid in a sample before and after an intervention or by comparing the amount and/or activity in one sample to the amount or activity of the same gene in another sample. In certain embodiments, modulation of a nucleic acid includes, but is not limited to, a change in the amount in which expression of a certain gene in one sample is reduced (e.g. down regulated) relative to expression of the same gene in another sample. In certain embodiments, a decrease in the expression (e.g. down regulation) of a gene describes a gene which has been observed to have lower expression (e.g. lower mRNA levels), in one sample compared to another sample (e.g. a control). In certain embodiments, modulation of expression includes, but is not limited to, the amount in which expression of a certain gene in one sample is increased (e.g. up regulated) relative to expression of the same gene in another sample. In certain embodiments, an increase in the expression (up regulation) of a gene describes a gene which has been observed to have higher expression (e.g. higher mRNA levels), in one sample compared to another sample (e.g. a control).

As used herein, "activity" means performance of a function. In certain embodiments, activity of a nucleic acid includes, but is not limited to, expression of an encoded protein, modulation of expression of one or more other nucleic acids, structural functions, and any other biological activity performed by a nucleic acid.

As used herein, "amount" means amount or concentration.

As used herein, "target nucleic acid" means a nucleic acid molecule to which an antisense compound hybridizes, resulting in a desired antisense activity.

As used herein, "off-target nucleic acid" means a nucleic acid molecule other than the target nucleic acid. Because some off-target nucleic acids may share some sequence homology with a target nucleic acid, in certain instances an antisense compound may hybridize to an off-target nucleic acid. In certain embodiments, the amount, activity, or expression of an off-target nucleic acid may be modulated by an antisense compound. Such modulation may have no consequences or may result in one or more antisense activity, including but not limited to toxicity. In certain embodiments, off-target nucleic acids include, but are not limited to, off-target genes.

As used herein, "sentinel gene" means a gene, the modulation of the amount or activity of which in vitro correlates with toxicity in vivo. In certain embodiments, toxicity is hepatotoxicity. In certain embodiments, sentinel genes include, but are not limited to, off-target genes. In certain embodiments, a decrease in expression of a sentinel gene in vitro correlates with an increase in AST levels in vivo. In certain embodiments, a decrease in expression of a sentinel gene in vitro correlates with an increase in ALT levels in vivo. In certain embodiments, an increase in expression of a sentinel gene in vitro correlates with toxicity in vivo. In certain embodiments, modulation of the amount or activity of a sentinel gene in vitro correlates with in vivo toxicity with a coefficient of determination of at least 0.5. In certain embodiments, modulation of the amount or activity of a sentinel gene in vitro correlates with in vivo toxicity with a coefficient of determination of at least 0.6. In certain embodiments, modulation of the amount or activity of a sentinel gene in vitro correlates with in vivo toxicity with a coefficient of determination of at least 0.7. In certain embodiments, modulation of the amount or activity of a sentinel gene in vitro correlates with in vivo toxicity with a coefficient of determination of at least 0.8.

As used herein, "mRNA" means an RNA molecule that encodes a protein.

As used herein, "pre-mRNA" means an RNA transcript that has not been fully processed into mRNA. Pre-RNA includes one or more intron.

As used herein, "object RNA" means an RNA molecule other than a target RNA, the amount, activity, splicing, and/or function of which is modulated, either directly or indirectly, by a target nucleic acid. In certain embodiments, a target nucleic acid modulates splicing of an object RNA. In certain such embodiments, an antisense compound modulates the amount or activity of the target nucleic acid, resulting in a change in the splicing of an object RNA and ultimately resulting in a change in the activity or function of the object RNA.

As used herein, "microRNA" means a naturally occurring, small, non-coding RNA that represses gene expression of at least one mRNA. In certain embodiments, a microRNA represses gene expression by binding to a target site within a 3' untranslated region of an mRNA. In certain embodiments, a microRNA has a nucleobase sequence as set forth in miRBase, a database of published microRNA sequences found at http://microrna.sanger.ac.uk/sequences/. In certain embodiments, a microRNA has a nucleobase sequence as set forth in miRBase version 18 released November 2011, which is herein incorporated by reference in its entirety.

As used herein, "microRNA mimic" means an oligomeric compound having a sequence that is at least partially identical to that of a microRNA. In certain embodiments, a microRNA mimic comprises the microRNA seed region of a microRNA. In certain embodiments, a microRNA mimic modulates translation of more than one target nucleic acids. In certain embodiments, a microRNA mimic is double-stranded.

As used herein, "differentiating nucleobase" means a nucleobase that differs between two nucleic acids. In certain instances, a target region of a target nucleic acid differs by 1-4 nucleobases from a non-target nucleic acid. Each of those differences is referred to as a differentiating nucleobase. In certain instances, a differentiating nucleobase is a single-nucleotide polymorphism.

As used herein, "target-selective nucleoside" means a nucleoside of an antisense compound that corresponds to a differentiating nucleobase of a target nucleic acid.

As used herein, "allele" means one of a pair of copies of a gene existing at a particular locus or marker on a specific chromosome, or one member of a pair of nucleobases existing at a particular locus or marker on a specific chromosome, or one member of a pair of nucleobase sequences existing at a particular locus or marker on a specific chromosome. For a diploid organism or cell or for autosomal chromosomes, each allelic pair will normally occupy corresponding positions (loci) on a pair of homologous chromosomes, one inherited from the mother and one inherited from the father. If these alleles are identical, the organism or cell is said to be "homozygous" for that allele; if they differ, the organism or cell is said to be "heterozygous" for that allele. "Wild-type allele" refers to the genotype typically not associated with disease or dysfunction of the gene product. "Mutant allele" refers to the genotype associated with disease or dysfunction of the gene product.

As used herein, "targeting" or "targeted to" means the association of an antisense compound to a particular target nucleic acid molecule or a particular region of a target nucleic acid molecule. An antisense compound targets a target nucleic acid if it is sufficiently complementary to the target nucleic acid to allow hybridization under physiological conditions.

As used herein, "nucleobase complementarity" or "complementarity" when in reference to nucleobases means a nucleobase that is capable of base pairing with another nucleobase. For example, in DNA, adenine (A) is complementary to thymine (T). For example, in RNA, adenine (A) is complementary to uracil (U). In certain embodiments, complementary nucleobase means a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, "non-complementary" in reference to nucleobases means a pair of nucleobases that do not form hydrogen bonds with one another.

As used herein, "complementary" in reference to oligomeric compounds (e.g., linked nucleosides, oligonucleotides, or nucleic acids) means the capacity of such oligomeric compounds or regions thereof to hybridize to another oligomeric compound or region thereof through nucleobase complementarity under stringent conditions. Complementary oligomeric compounds need not have nucleobase complementarity at each nucleoside. Rather, some mismatches are tolerated. In certain embodiments, complementary oligomeric compounds or regions are complementary at 70% of the nucleobases (70% complementary). In certain embodiments, complementary oligomeric compounds or regions are 80% complementary. In certain embodiments, complementary oligomeric compounds or regions are 90% complementary. In certain embodiments, complementary oligomeric compounds or regions are 95% complementary. In certain embodiments, complementary oligomeric compounds or regions are 100% complementary.

As used herein, "mismatch" means a nucleobase of a first oligomeric compound that is not capable of pairing with a nucleobase at a corresponding position of a second oligomeric compound, when the first and second oligomeric compound are aligned. Either or both of the first and second oligomeric compounds may be oligonucleotides.

As used herein, "hybridization" means the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleobases.

As used herein, "specifically hybridizes" means the ability of an oligomeric compound to hybridize to one nucleic acid site with greater affinity than it hybridizes to another nucleic acid site. In certain embodiments, an antisense oligonucleotide specifically hybridizes to more than one target site.

As used herein, "fully complementary" in reference to an oligonucleotide or portion thereof means that each nucleobase of the oligonucleotide or portion thereof is capable of pairing with a nucleobase of a complementary nucleic acid or contiguous portion thereof. Thus, a fully complementary region comprises no mismatches or unhybridized nucleobases in either strand.

As used herein, "percent complementarity" means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound.

As used herein, "percent identity" means the number of nucleobases in a first nucleic acid that are the same type (independent of chemical modification) as nucleobases at corresponding positions in a second nucleic acid, divided by the total number of nucleobases in the first nucleic acid.

As used herein, "modification motif" means a pattern of chemical modifications in an oligomeric compound or a region thereof. Motifs may be defined by modifications at certain nucleosides and/or at certain linking groups of an oligomeric compound.

As used herein, "nucleoside motif" means a pattern of nucleoside modifications in an oligomeric compound or a region thereof. The linkages of such an oligomeric compound may be modified or unmodified. Unless otherwise indicated, motifs herein describing only nucleosides are intended to be nucleoside motifs. Thus, in such instances, the linkages are not limited.

As used herein, "sugar motif" means a pattern of sugar modifications in an oligomeric compound or a region thereof.

As used herein, "linkage motif" means a pattern of linkage modifications in an oligomeric compound or region thereof. The nucleosides of such an oligomeric compound may be modified or unmodified. Unless otherwise indicated, motifs herein describing only linkages are intended to be linkage motifs. Thus, in such instances, the nucleosides are not limited.

As used herein, "nucleobase modification motif" means a pattern of modifications to nucleobases along an oligonucleotide. Unless otherwise indicated, a nucleobase modification motif is independent of the nucleobase sequence.

As used herein, "sequence motif" means a pattern of nucleobases arranged along an oligonucleotide or portion thereof. Unless otherwise indicated, a sequence motif is independent of chemical modifications and thus may have any combination of chemical modifications, including no chemical modifications.

As used herein, "type of modification" in reference to a nucleoside or a nucleoside of a "type" means the chemical modification of a nucleoside and includes modified and unmodified nucleosides. Accordingly, unless otherwise indicated, a "nucleoside having a modification of a first type" may be an unmodified nucleoside.

As used herein, "differently modified" mean chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

As used herein, "the same type of modifications" refers to modifications that are the same as one another, including absence of modifications. Thus, for example, two unmodified DNA nucleoside have "the same type of modification," even though the DNA nucleoside is unmodified. Such nucleosides having the same type modification may comprise different nucleobases.

As used herein, "pharmaceutically acceptable carrier or diluent" means any substance suitable for use in administering to an animal. In certain embodiments, a pharmaceutically acceptable carrier or diluent is sterile saline. In certain embodiments, such sterile saline is pharmaceutical grade saline.

As used herein, "substituent" and "substituent group," means an atom or group that replaces the atom or group of a named parent compound. For example a substituent of a modified nucleoside is any atom or group that differs from the atom or group found in a naturally occurring nucleoside (e.g., a modified 2'-substituent is any atom or group at the 2'-position of a nucleoside other than H or OH). Substituent groups can be protected or unprotected. In certain embodiments, compounds of the present invention have substituents at one or at more than one position of the parent compound. Substituents may also be further substituted with other substituent groups and may be attached directly or via a linking group such as an alkyl or hydrocarbyl group to a parent compound.

Likewise, as used herein, "substituent" in reference to a chemical functional group means an atom or group of atoms differs from the atom or a group of atoms normally present in the named functional group. In certain embodiments, a substituent replaces a hydrogen atom of the functional group (e.g., in certain embodiments, the substituent of a substituted methyl group is an atom or group other than hydrogen which replaces one of the hydrogen atoms of an unsubstituted methyl group). Unless otherwise indicated, groups amenable for use as substituents include without limitation, halogen, hydroxyl, alkyl, alkenyl, alkynyl, acyl (—C(O)$R_{aa}$), carboxyl (—C(O)O—$R_{aa}$), aliphatic groups, alicyclic groups, alkoxy, substituted oxy (—O—$R_{aa}$), aryl, aralkyl, heterocyclic radical, heteroaryl, heteroarylalkyl, amino (—N($R_{bb}$)($R_{cc}$)), imino(=$NR_{bb}$), amido (—C(O)N($R_{bb}$)($R_{cc}$) or —N($R_{bb}$)C(O)$R_{aa}$), azido (—$N_3$), nitro (—$NO_2$), cyano (—CN), carbamido (—OC(O)N($R_{bb}$)($R_{cc}$) or —N($R_{bb}$)C(O)O$R_{aa}$), ureido (—N($R_{bb}$)C(O)N($R_{bb}$)($R_{cc}$)), thioureido (—N($R_{bb}$)C(S)N($R_{bb}$)—($R_{cc}$)), guanidinyl (—N($R_{bb}$)C(=$NR_{bb}$)N($R_{bb}$)($R_{cc}$)), amidinyl (—C(=$NR_{bb}$)N($R_{bb}$)($R_{cc}$) or —N($R_{bb}$)C(=$NR_{bb}$)($R_{aa}$)), thiol (—$SR_{bb}$), sulfinyl (—S(O)$R_{bb}$), sulfonyl (—S(O)$_2R_{bb}$) and sulfonamidyl (—S(O)$_2$N($R_{bb}$)($R_{cc}$) or —N($R_{bb}$)S—(O)$_2R_{bb}$). Wherein each $R_{aa}$, $R_{bb}$ and $R_{cc}$ is, independently, H, an optionally linked chemical functional group or a further substituent group with a preferred list including without limitation, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

As used herein, "alkyl," as used herein, means a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred.

As used herein, "alkenyl," means a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein, "alkynyl," means a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein, "acyl," means a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein, "alicyclic" means a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein, "aliphatic" means a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines. Aliphatic groups as used herein may optionally include further substituent groups.

As used herein, "alkoxy" means a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein, "aminoalkyl" means an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

As used herein, "aralkyl" and "arylalkyl" mean an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

As used herein, "aryl" and "aromatic" mean a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein, "halo" and "halogen," mean an atom selected from fluorine, chlorine, bromine and iodine.

As used herein, "heteroaryl," and "heteroaromatic," mean a radical comprising a mono- or polycyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

B. Methods of Predicting In Vivo Toxicity

Provided herein are methods for determining the in vitro and in vivo toxicity of oligomeric compounds. In certain embodiments, the methods generally comprise contacting a cell with an oligomeric compound in vitro, measuring the modulation of the activity or amount of one or more off-target genes and predicting the in vivo toxicity of the oligomeric compound based on the in vitro modulation of the activity or amount of one or more of the off-target genes. In certain embodiments, the general methods disclosed herein will enable one having skill in the art to rapidly screen large numbers of new or previously known oligomeric compounds in vitro and predict whether such test oligomeric compounds will be toxic in vivo, based on the in vitro modulation of the amount or activity of certain off-target genes. Thus, the time and expense of administering numerous oligomeric compounds to animals to determine in vivo toxicity may be reduced, and one may more rapidly identify and avoid oligomeric compounds that may have potentially toxic in vivo properties.

In certain embodiments, the method generally comprises identifying one or more off-target genes, the up- or down-regulation of which in vitro correlates with an increase in toxicity in vivo. In certain embodiments, once such off-target genes are identified, the invention provides methods of screening oligomeric compounds in vitro to determine whether they up- or down-regulate such off-target genes. In certain embodiments, the methods disclosed herein enable one having skill in the art to accurately predict the in vivo toxicity of a given oligomeric compound through the in vitro measurement of certain down-regulated off-target genes. In certain embodiments, the methods disclosed herein enable one having skill in the art to accurately predict the in vivo toxicity of a given oligomeric compound through the in vitro measurement of certain up-regulated off-target genes.

a. Toxicity

In vitro or in vivo toxicity may be measured by any method known to those having skill in the art. In some embodiments, toxicity is measured by liver activity. In some embodiments, toxicity is measured by kidney activity. In some embodiments, toxicity is measured by pancreas activity. In some embodiments, toxicity is measured by assessing circulating liver enzymes such as Aspartate transaminase (AST) and/or Alanine transaminase (ALT). In certain such embodiments, AST and/or ALT levels at timepoints after the administration of a test oligomeric compound are compared to baseline values obtained prior to administration, to those of control animals that did not receive test oligomeric compound, or to values known to be associated with normal animals from previous experiments (historical controls) or from literature. In certain embodiments, toxicity is measured by assessing alkaline phosphatase (ALP) levels. In certain such embodiments, ALP levels at timepoints after the administration of a test oligomeric compound are compared to baseline values obtained prior to administration, to those of control animals that did not receive test oligomeric compound, or to values known to be associated with normal animals from previous experiments (historical controls) or from literature. In certain embodiments, toxicity is measured by assessing total bilirubin (TBIL) levels. In certain such embodiments, TBIL levels at timepoints after the administration of a test oligomeric compound are compared to baseline values obtained prior to administration, to those of control animals that did not receive test oligomeric compound, or to values known to be associated with normal animals from previous experiments (historical controls) or from literature. In certain embodiments, toxicity is measured by assessing albumin levels. In certain such embodiments, albumin levels at timepoints after the administration of a test oligomeric compound are compared to baseline values obtained prior to administration, to those of control animals that did not receive test oligomeric compound, or to values known to be associated with normal animals from previous experiments (historical controls) or from literature. In certain embodiments, toxicity is measured by assessing serum glucose levels. In certain such embodiments, serum glucose levels at timepoints after the administration of a test oligomeric compound are compared to baseline values obtained prior to administration, to those of control animals that did not receive test oligomeric compound, or to values known to be associated with normal animals from previous experiments (historical controls) or from literature. In certain embodiments, toxicity is measured by assessing lactate dehydrogenase (LDH) levels. In certain such embodiments, lactate dehydrogenase (LDH) levels at timepoints after the administration of a test oligomeric compound are compared to baseline values obtained prior to administration, to those of control animals that did not receive test oligomeric compound, or to values known to be associated with normal animals from previous experiments (historical controls) or from literature.

b. Modulation of the Amount or Activity of Off-Target Genes In Vivo

In certain embodiments the modulation of the amount or activity of off-target genes in vivo may be determined by microarray analysis. After administration of an oligomeric compound to an animal in vivo or a group of animals in vivo, one or more of the animals may be sacrificed and the tissue analyzed by microarray to determine expression levels of a large number of specific genes, or even the entire genome (genome profiling). In certain embodiments, one or more of the animals may be sacrificed and the tissue analyzed by microarray analysis at various times (e.g., 0, 24 hours, 48 hours, 72 hours, 96 hours) after administration of an oligomeric compound. Such microarray analysis may be compared to similar analyses from untreated animals and/or from animals treated with a different oligomeric compound.

In certain embodiments, toxixity of treated animals is assessed at various times. In certain embodiments, the tissue of the sacrificed animals is analyzed for indications of toxicity by any method known to those having skill in the art. In certain embodiments, any animals not sacrificed for microarray analysis may continue to be observed for indications of acute toxicity at various time points, for example at 24 hours, 48 hours, 72 hours, and 96 hours after administration.

In certain embodiments, the degree of the change in expression of certain off-target genes as determined by microarray analysis may be correlated with some measure of toxicity. In certain embodiments, the degree of the decrease in expression of certain off-target genes may be correlated with increase in AST levels or ALT levels. In certain embodiments, after microarray analysis, the degree of the increase in expression of certain off-target genes may be correlated with the amount of increase in some measure of toxicity, for example, AST levels or ALT levels. After correlation between the in vivo modulation of the amount or activity of an off-target gene and in vivo toxicity is performed, the off-target genes may be sorted by the coefficient of determination from highest to lowest. In this manner off-target genes may be identified where the in vivo modulation of the amount or activity of a gene correlates strongly with some measure of toxicity (sentinel genes), for example AST levels or ALT levels. In certain embodiments, off-target genes having the strongest correlation between a decrease in in vivo expression and toxicity may be identified as sentinel genes. In certain embodiments, off-target genes having the strongest correlation between a decrease in in vivo expression and and increase in AST levels may be identified as sentinel genes. In certain embodiments, off-target genes having the strongest correlation between a decrease in in vivo expression and and increase in ALT levels may be identified sentinel genes. In certain embodiments, off-target genes having the strongest correlation between an increase in expression in vivo and toxicity may be identified sentinel genes. In certain embodiments, off-target genes having the strongest correlation between an increase in in vivo expression and and increase in ALT levels may be identified as sentinel genes. In certain embodiments, off-target genes having the strongest correlation between an increase in in vivo expression and and increase in AST levels may be identified as sentinel genes.

In certain embodiments, the modulation of the amount or activity of off-target genes may be correlated with one or more measure of toxicity. One having skill in the art may correlate the modulation of the amount or activity of off-target genes with one or more measure of toxicity using any statistical method known to those having skill in the art. In certain embodiments, the correlation of the modulation of the amount or activity of off-target genes with one or more measure of toxicity is assessed by calculating the coefficient of determination. In certain embodiments, the correlation of the modulation of the amount or activity of off-target genes may be correlated with one or more measure of toxicity by using the coefficient of determination, $r^2$. In this manner sentinel genes may be identified where the in vivo modulation of the amount or activity of an off-target gene in response to an oligomeric compound correlates strongly with some measure of toxicity.

In certain embodiments the degree of the decrease in expression of an off-target gene may be correlated with an increase in AST levels. In certain embodiments the degree of the decrease in expression of an off-target gene may be correlated with an increase in ALT levels. In certain embodiments the degree of the decrease in expression of an off-target gene may be correlated with an increase in ALP levels. In certain embodiments the degree of the decrease in expression of an off-target gene may be correlated with an increase in TBIL levels. In certain embodiments the degree of the decrease in expression of an off-target gene may be correlated with an increase in albumin levels. In certain embodiments the degree of the decrease in expression of an off-target gene may be correlated with an increase in serum glucose levels. In certain embodiments the degree of the decrease in expression of an off-target gene may be correlated with an increase in LDH levels.

In certain embodiments the degree of the increase in expression of an off-target gene may be correlated with an increase in AST levels. In certain embodiments the degree of the increase in expression of an off-target gene may be correlated with an increase in ALT levels. In certain embodiments the degree of the increase in expression of an off-target gene may be correlated with an increase in ALP levels. In certain embodiments the degree of the increase in expression of an off-target gene may be correlated with an increase in TBIL levels. In certain embodiments the degree of the increase in expression of an off-target gene may be correlated with an increase in albumin levels. In certain embodiments the degree of the increase in expression of an off-target gene may be correlated with an increase in serum glucose levels. In certain embodiments the degree of the increase in expression of an off-target gene may be correlated with an increase in LDH levels.

In certain embodiments the degree of the decrease in expression of a sentinel gene may be correlated with an increase in AST levels. In certain embodiments the degree of the decrease in expression of a sentinel gene may be correlated with an increase in ALT levels. In certain embodiments the degree of the decrease in expression of a sentinel gene may be correlated with an increase in ALP levels. In certain embodiments the degree of the decrease in expression of a sentinel gene may be correlated with an increase in TBIL levels. In certain embodiments the degree of the decrease in expression of a sentinel gene may be correlated with an increase in albumin levels. In certain embodiments the degree of the decrease in expression of a sentinel gene may be correlated with an increase in serum glucose levels. In certain embodiments the degree of the decrease in expression of a sentinel gene may be correlated with an increase in LDH levels.

In certain embodiments the degree of the increase in expression of a sentinel gene may be correlated with an increase in AST levels. In certain embodiments the degree of the increase in expression of a sentinel gene may be correlated with an increase in ALT levels. In certain embodiments the degree of the increase in expression of a sentinel gene may be correlated with an increase in ALP levels. In certain embodiments the degree of the increase in expression of a sentinel gene may be correlated with an increase in TBIL levels. In certain embodiments the degree of the increase in expression of a sentinel gene may be correlated with an increase in albumin levels. In certain embodiments the degree of the increase in expression of a sentinel gene may be correlated with an increase in serum glucose levels. In certain embodiments the degree of the increase in expression of a sentinel gene may be correlated with an increase in LDH levels.

In certain embodiments, any number of off-target genes may be ranked according to coefficient of determination, $r^2$, between toxicity and the degree modulation of the amount or activity of off-target gene expression. In certain embodiments, any number of off-target genes may be ranked according to the strength of correlation between toxicity as measured by ALT levels and the degree of the decrease in off-target expression. In certain embodiments, any number of off-target genes may be ranked according to the strength of correlation between toxicity as measured by AST levels and the degree the decrease in off-target gene expression.

In certain embodiments, any number of sentinel genes may be ranked according to coefficient of determination, $r^2$, between toxicity and the degree modulation of the amount or activity of sentinel gene expression. In certain embodiments, any number of sentinel genes may be ranked according to the strength of correlation between toxicity as measured by ALT levels and the degree of the decrease in sentinel expression. In certain embodiments, any number of sentinel genes may be ranked according to the strength of correlation between toxicity as measured by AST levels and the degree the decrease in sentinel gene expression.

In certain embodiments, the 1 to 150 or more off-target genes having the strongest in vivo correlation between a decrease in expression and toxicity may be identified as sentinel genes. In certain embodiments, the 1 to 100 off-target genes having the strongest in vivo correlation between a decrease in expression and toxicity may be identified as sentinel genes. In certain embodiments, the 1 to 50 off-target genes genes having the strongest in vivo correlation between a decrease in expression and toxicity may be identified as sentinel genes. In certain embodiments, the 1 to 40 off-target genes having the strongest correlation between a decrease in expression and toxicity may be identified as sentinel genes. In certain embodiments, the 1 to 30 off-target genes having the strongest correlation between a decrease in expression and toxicity may be identified as sentinel genes. In certain embodiments, the 1 to 20 off-target genes having the strongest correlation between a decrease in expression and toxicity may be identified as sentinel genes. In certain embodiments, the 1 to 10 off-target genes having the strongest correlation between a decrease in expression and toxicity may be identified as sentinel genes. In certain embodiments, the 1 to 5 off-target genes having the strongest correlation between a decrease in expression and toxicity may be identified as sentinel genes.

In certain embodiments, the 1 to 150 or more off-target genes having the strongest correlation between an increase in expression and toxicity may be identified as sentinel genes. In certain embodiments, the 1 to 100 off-target genes having the strongest correlation between an increase in expression and toxicity may be identified as sentinel genes. In certain embodiments, the 1 to 50 off-target genes having the strongest correlation between an increase in expression and toxicity may be identified as sentinel genes. In certain embodiments, the 1 to 40 off-target genes having the strongest correlation between an increase in expression and toxicity may be identified as sentinel genes. In certain embodiments, the 1 to 30 off-target genes having the strongest correlation between an increase in expression and toxicity may be identified as sentinel genes. In certain embodiments, the 1 to 20 off-target genes having the strongest correlation between an increase in expression and toxicity may be identified as sentinel genes. In certain embodiments, the 1 to 10 off-target genes having the strongest correlation between an increase in expression and toxicity may be identified as sentinel genes. In certain embodiments, the 1 to 5 off-target genes having the strongest correlation between an increase in expression and toxicity may be identified as sentinel genes.

The methods described herein enable one having skill in the art to then identify any number of off-target genes, sentinel genes, or transcripts. The methods described herein enable one having skill in the art to then identify any number of off-target genes, sentinel genes, or transcripts wherein the decrease in expression of the sentinel gene or transcript is correlated to some measure of toxicity. The methods described herein enable one having skill in the art to then identify any number of off-target genes, sentinel genes, or transcripts wherein the increase in expression of the sentinel gene or transcript is correlated to some measure of toxicity. In this manner, one having skill in the art may identify any number of off-target genes, sentinel genes, or transcripts according to the correlation between the modulation of the amount or activity of the off-target genes, sentinel genes, or transcripts in vivo and any measure of toxicity. In certain embodiments, the off-target genes, sentinel genes, or transcripts identified may be used for further in vitro evaluation to develop a sub-set of in vitro off-target genes, sentinel genes, or transcripts that correlate to in vivo toxicity. In certain embodiments, at least one antisense compound that is predicted not to be toxic in vivo is made and then tested in an animal.

In certain embodiments, sentinel genes are identified empirically. For example, in certain embodiments, oligomeric compounds that modulate the amount or activity of a particular off target gene in vitro are found to cause toxicity when administered in vivo. Such observed correlation between modulation of the amount or activity of an off-target gene in vitro and corresponding in vivo toxicity does not necessarily indicate that modulation of the amount or activity of the off target gene is the cause of the observed toxicity. Indeed, an off-target gene might not even be modulated in vivo. The utility of the observation, however, is independent of mechanism. Regardless of causation, oligomeric compounds that modulate the amount or activity of a strongly correlated off-target sentinel gene are predicted to be toxic in vivo. In certain embodiments, homology between an oligomeric compound and a sentinel gene does not result in the modulation of the amount or activity of said sentinel gene. In certain embodiments, homology between an oligomeric compound and an off-target gene does not result in the modulation of the amount or activity of said off target gene. In certain embodiments, an oligomeric compound modulates the amount or activity of an off-target gene without hybridizing to said off-target gene. In certain embodiments, an oligomeric compound modulates the amount or activity of a sentinel gene without hybridizing to said sentinel gene.

c. Modulation of the Amount or Activity of Off-Target Genes In Vivo

In certain embodiments, the modulation of the amount or activity of any number of off-target genes in response to any given oligonucleotide may be measured in vitro. Any suitable cell lines that express genes of interest may be used for the in vitro screen. In certain embodiments hepatocyte cell lines may be used. In certain embodiments, BEND cell lines may be used. In certain embodiments, HeLa cell lines may be used. In certain embodiments HepG2 cell lines may be used. The degree of modulation of the amount or activity of the off-target genes in-vitro may then be compared with off-target genes that have been identified as being modulated in vivo. In this manner, off-target genes that have a high amount of modulation of amount or activity in vivo and which also have a high amount of modulation of amount or activity in vitro may be identified. In certain embodiments, the modulation of the amount or activity of off-target genes identified as having a high correlation between measurements of acute toxicity and a decrease in expression in vivo may be correlated with the degree of a decrease in expression in vitro. In certain embodiments, the modulation of the amount or activity of off-target genes identified as having a high correlation between acute toxicity and an increase in expression in vivo may be correlated with the modulation of amount or activity in vitro. In certain embodiments, certain off-target genes may be identified that have a high correlation between a change in the modulation of amount or activity in vivo and a change in the modulation of amount or activity in vitro. For example, in certain embodiments, certain off-target genes identified as demonstrating a relatively strong decrease in expression in vivo, will also demonstrate a relatively strong decrease in expression in vitro. In certain embodiments, the identification of such in vitro off-target genes, for example, genes that demonstrate a decrease in expression upon transfection with a given oligomeric compound, will then predict a decrease in expression of the same off-target genes in vivo, and therefore will predict toxicity in vivo. Once in vitro off-target genes are identified, then any oligomeric compound maybe screened in vitro by transfecting a cell with the oligomeric compound and measuring the modulation of the amount or activity of one or more identified off-target genes. In some embodiments, this method reduces the need for an acute single-dose in vivo screen for most oligomeric compounds.

Any method known to those having skill in the art may be used to measure the modulation of the amount or activity of the off-target genes in vitro. In certain embodiments, cells may be transfected with oligomeric compounds using electroporation. Other suitable transfection reagents known in the art include, but are not limited to, CYTOFECTIN™, LIPOFECTAMINE™, OLIGOFECTAMINE™, and FUGENE™. In certain embodiments, RT-PCR is used to measure the modulation of the amount or activity of off-target genes in vitro.

d. Certain Off-Target Genes

In certain embodiments, the modulation of the amount or activity of one or more off-target genes in vitro is used to determine the toxicity of an oligomeric compound in vivo. In certain embodiments the decrease in expression of one or more off-target genes in vitro is used to determine the toxicity of an oligomeric compound in vivo. In certain embodiments the increase in expression of one or more off-target genes in vitro is used to determine the toxicity of an oligomeric compound in vivo.

In certain embodiments, the amount of the decrease in expression in vitro of one or more of the off-target genes listed in Table 1 below may be used to determine the toxicity of an oligomeric compound in vivo.

TABLE 1

In Vitro Off-Target Genes

| Symbol | Official Name |
|---|---|
| Adcy9 | adenylate cyclase 9 |
| Ptprk | protein tyrosine phosphatase, receptor type, K |
| Tbc1d22a | TBC1 domain family, member 22a |
| Exoc6b | exocyst complex component 6B |
| Fto | fat mass and obesity associated |
| RAPTOR | regulatory associated protein of MTOR, complex 1 |
| Iqgap2 | IQ motif containing GTPase activating protein 2 |
| Vti1a | vesicle transport through interaction with t-SNAREs homolog 1A |
| BC057079 | cDNA sequence BC057079 |
| Fbxl17 | F-box and leucine-rich repeat protein 17 |
| Bre | brain and reproductive organ-expressed protein |
| Cgnl1 | cingulin-like 1 |
| Msi2 | Musashi homolog 2 (*Drosophila*) |
| Mcph1 | microcephaly, primary autosomal recessive 1 |
| Atxn1 | ataxin 1 |
| Vps13b | vacuolar protein sorting 13B (yeast) |
| Cadps2 | Ca2+-dependent activator protein for secretion 2 |
| Ppp3ca | protein phosphatase 3, catalytic subunit, alpha isoform |
| Ppm1l | protein phosphatase 1 (formerly 2C)-like |
| Ubac2 | ubiquitin associated domain containing 2 |
| Bcas3 | breast carcinoma amplified sequence 3 |
| Gphn | gephyrin |
| Atp9b | ATPase, class II, type 9B |
| Chn2 | chimerin (chimaerin) 2 |
| Fars2 | phenylalanine-tRNA synthetase 2 (mitochondrial) |
| Adk | adenosine kinase |
| Odz3 | odd Oz/ten-m homolog 3 (*Drosophila*) |
| Macrod1 | MACRO domain containing 1 |
| Atg10 | Autophagy-related protein 10 |
| Fggy | carbohydrate kinase domain containing |
| Vps53 | vacuolar protein sorting 53 homolog (*S. cerevisiae*) |
| Itpr2 | inositol 1,4,5-triphosphate receptor, type 2 |
| 0610012H03Rik | Riken cDNA 0610012H03 gene |

In certain embodiments, the degree of the increase in expression in vitro of one or more of the off-target genes listed in Table 2 below may be used to determine the toxicity of an oligomeric compound in vivo.

TABLE 2

In Vitro Off-Target Genes

| Symbol | Gene ID |
|---|---|
| Rassf1 | 56289 |
| Dus4l | 71916 |

TABLE 2-continued

In Vitro Off-Target Genes

| Symbol | Gene ID |
|---|---|
| Mdm2 | 17246 |
| Brp16 | 59053 |
| 0610010K14Rik | 104457 |
| Rce1 | 19671 |
| Ilf2 | 67781 |
| Setd1a | 233904 |
| Gar1 | 68147 |
| FAM203A | 59053 |

In certain embodiments, the amount of the decrease in expression in vitro of one or more of the off-target genes listed in Table 3 below may be used to determine the toxicity of an oligomeric compound in vivo.

TABLE 3

In Vitro Off-Target Genes

| Symbol | Gene ID |
|---|---|
| Rsrc1 | 66880 |
| Cadps2 | 320405 |
| Aprin | 100710 |
| Faf1 | 14084 |
| Sntg2 | 268534 |
| Odz3 | 23965 |
| St3gal3 | 20441 |
| Sox5 | 20678 |
| BC033915 | 70661 |
| A530050D06Rik | 104816 |
| Fbxl17 | 50758 |
| Msi2 | 76626 |
| Pard3 | 93742 |
| 4933407C03Rik | 74440 |
| Itpr1 | 16438 |
| Zdhhc14 | 224454 |
| Rrbp1 | 81910 |
| Mtmr14 | 97287 |
| Dpyd | 99586 |
| Ptprd | 19266 |
| Pcca | 110821 |
| Lmf1 | 76483 |
| Iqgap2 | 544963 |
| Centg2 | 347722 |
| Btbd9 | 224671 |
| Ubac2 | 68889 |
| Ptprk | 19272 |
| R3hdm2 | 71750 |
| Psme4 | 103554 |
| Ppp3ca | 19055 |
| Vps53 | 68299 |
| Vps13b | 666173 |
| Mgll | 23945 |
| Chn2 | 69993 |
| Atxn1 | 20238 |
| Acot7 | 70025 |
| Lpp | 210126 |
| Itpr2 | 16439 |
| Mapkap1 | 227743 |
| Stx8 | 55943 |
| Ghr | 14600 |
| Bcas3 | 192197 |
| Exoc6b///Sec15l2 | 75914 |
| 9030420J04Rik | 71544 |
| Pck1 | 18534 |
| Ube2e2 | 218793 |
| Pik3c2g | 18705 |
| 1300010F03Rik | 219189 |
| Apbb2 | 11787 |
| Mcph1 | 244329 |
| Sergef | 27414 |
| Adcy9 | 11515 |
| Pkp4 | 227937 |

TABLE 3-continued

In Vitro Off-Target Genes

| Symbol | Gene ID |
|---|---|
| Ascc3 | 77987 |
| Enpp2 | 18606 |
| Sel1l | 20338 |
| Macrod1 | 107227 |
| Vti1a | 53611 |
| Wdr7 | 104082 |
| 4932417H02Rik | 74370 |
| Bach2 | 12014 |
| 0610012H03Rik | 74088 |
| Adk | 11534 |
| Dym | 69190 |
| Pitpnm2 | 19679 |
| Slc41a2 | 338365 |
| Fgfr2 | 14183 |
| Bre | 107976 |
| Gphn | 268566 |
| Mical3 | 194401 |
| Fars2 | 69955 |
| Ap3b1 | 11774 |
| Vps13a | 271564 |
| Skap2 | 54353 |
| Sds | 231691 |
| Cova1///Enox2 | 209224 |
| Pitpnc1 | 71795 |
| Large | 16795 |
| Lrba | 80877 |
| Atg10 | 66795 |
| Atp9b | 50771 |
| Cask | 12361 |
| Ppm1l | 242083 |
| Alcam | 11658 |
| Atg7 | 74244 |
| Nfia | 18027 |
| Supt3h | 109115 |
| Med27 | 68975 |
| Cgnl1 | 68178 |
| Dennd1a | 227801 |
| Smoc1 | 64075 |
| Prkca | 18750 |
| 2210408F21Rik | 73652 |
| Map2k5 | 23938 |
| Dock4 | 238130 |
| LOC100036521 | 100036521 |
| Sil1 | 81500 |
| Tbc1d22a | 223754 |
| 2310009E04Rik | 75578 |
| BC057079 | 230393 |
| Fhit | 14198 |
| Uvrag | 78610 |
| Dtnb | 13528 |
| Fto | 26383 |
| Immp2l | 93757 |

In certain embodiments, the measurement of the modulation of the amount or activity of more than one off-target gene in vitro may increase the probability of predicting toxicity in vivo. For example, in certain embodiments, a cell is transfected with an oligomeric compound of interest and then the modulation of the amount or activity of two or more off-target genes is measured. In such embodiments, if both off-target genes are modulated then there is a higher probability that the oligomeric compound of interest is toxic than if only one of the two off-target genes were modulated. In certain embodiments, a cell is transfected with an oligomeric compound of interest and then the modulation of the amount or activity of three or more off-target genes is measured. In such embodiments, if all three off-target genes are modulated then there is a higher probability that the oligomeric compound of interest is toxic than if only one of the three off-target genes were modulated. In certain embodiments, a cell is transfected with an oligomeric compound of interest and then the modulation of the amount or activity of four or more off-target genes is measured. In such embodiments, if all four off-target genes are modulated or if two of the four off-target genes are modulated or if three of the four off-target genes are modulated then there is a higher probability that the oligomeric compound of interest is toxic than if only one of the four off-target genes were modulated. Likewise, in certain embodiments, if three of the four off-target genes were modulated then there is a higher probability that the oligomeric compound of interest is toxic than if only one of the four off-target genes were modulated or if two of the four off-target genes were modulated. In certain embodiments, a cell is transfected with an oligomeric compound of interest and then the modulation of the amount or activity of five or more off-target genes is measured. In such embodiments, if all five off-target genes are modulated or if two of the five off-target genes are modulated or if three of the five or four of the five off-target genes are modulated then there is a higher probability that the oligomeric compound of interest is toxic than if only one of the four off-target genes were modulated. In certain embodiments, a cell is transfected with an oligomeric compound of interest and then the modulation of the amount or activity of at least six off-target genes is measured. In such embodiments, if all six off-target genes are modulated or if two of the six off-target genes are modulated or if three of the six or four of the six or five of the six off-target genes are modulated then there is a higher probability that the oligomeric compound of interest is toxic than if only one of the four off-target genes were modulated.

In certain embodiments the off-target gene is Adcy9. In certain embodiments the off-target gene is Ptprk. In certain embodiments the off-target gene is Tbc1d22a. In certain embodiments the off-target gene is Exoc6b. In certain embodiments the off-target gene is Fto. In certain embodiments the off-target gene is RAPTOR. In certain embodiments the off-target gene is Iqgap2. In certain embodiments the off-target gene is Vti1a. In certain embodiments the off-target gene is BC057079. In certain embodiments the off-target gene is Fbxl17. In certain embodiments the off-target gene is Bre. In certain embodiments the off-target gene is Cgnl1. In certain embodiments the off-target gene is Msi2. In certain embodiments the off-target gene is Mcph1. In certain embodiments the off-target gene is Atxn1. In certain embodiments the off-target gene is Vps13b. In certain embodiments the off-target gene is Cadps2. In certain embodiments the off-target gene is Ppp3ca. In certain embodiments the off-target gene is Ppm1l. In certain embodiments the off-target gene is Ubac2. In certain embodiments the off-target gene is Bcas3. In certain embodiments the off-target gene is Gphn. In certain embodiments the off-target gene is Atp9b. In certain embodiments the off-target gene is Chn2. In certain embodiments the off-target gene is Fars2. In certain embodiments the off-target gene is Adk. In certain embodiments the off-target gene is Odz3. In certain embodiments the off-target gene is Macrod1. In certain embodiments the off-target gene is Atg10. In certain embodiments the off-target gene is Fggy. In certain embodiments the off-target gene is Vps53. In certain embodiments the off-target gene is Itpr2. In certain embodiments the off-target gene is 0610012H03Rik.

In certain embodiments the off-target gene is Rassf1. In certain embodiments the off-target gene is Dus41. In certain embodiments the off-target gene is Mdm2. In certain embodiments the off-target gene is Brp16. In certain embodiments the off-target gene is 0610010K14Rik. In certain embodiments the off-target gene is Rce1. In certain embodiments the off-target gene is Ilf2. In certain embodiments the off-target gene is Setd1a. In certain embodiments the off-target gene is Gar1. In certain embodiments the off-target gene is FAM203A.

In certain embodiments the off-target gene is Rsrc1. In certain embodiments the off-target gene is Cadps2. In certain embodiments the off-target gene is Aprin. In certain embodiments the off-target gene is Faf1. In certain embodiments the off-target gene is Sntg2. In certain embodiments the off-target gene is Odz3. In certain embodiments the off-target gene is St3gal3. In certain embodiments the off-target gene is Sox5. In certain embodiments the off-target gene is BC033915. In certain embodiments the off-target gene is A530050D06Rik. In certain embodiments the off-target gene is Fbxl17. In certain embodiments the off-target gene is Msi2. In certain embodiments the off-target gene is Pard3. In certain embodiments the off-target gene is 4933407C03Rik. In certain embodiments the off-target gene is Itpr1. In certain embodiments the off-target gene is Zdhhc14. In certain embodiments the off-target gene is Rrbp1. In certain embodiments the off-target gene is Mtmr14. In certain embodiments the off-target gene is Dpyd. In certain embodiments the off-target gene is Ptprd. In certain embodiments the off-target gene is Pcca. In certain embodiments the off-target gene is Lmf1. In certain embodiments the off-target gene is Iqgap2. In certain embodiments the off-target gene is Centg2. In certain embodiments the off-target gene is Btbd9. In certain embodiments the off-target gene is Ubac2. In certain embodiments the off-target gene is Ptprk. In certain embodiments the off-target gene is R3hdm2. In certain embodiments the off-target gene is Psme4. In certain embodiments the off-target gene is Ppp3ca. In certain embodiments the off-target gene is Vps53. In certain embodiments the off-target gene is Vps13b. In certain embodiments the off-target gene is Mgll. In certain embodiments the off-target gene is Chn2. In certain embodiments the off-target gene is Atxn1. In certain embodiments the off-target gene is Acot7. In certain embodiments the off-target gene is Lpp. In certain embodiments the off-target gene is Itpr2. In certain embodiments the off-target gene is Mapkap1. In certain embodiments the off-target gene is Stx8. In certain embodiments the off-target gene is Ghr. In certain embodiments the off-target gene is Bcas3. In certain embodiments the off-target gene is Exoc6b///Sec1512. In certain embodiments the off-target gene is 9030420J04Rik.

In certain embodiments the off-target gene is Pck1. In certain embodiments the off-target gene is Ube2e2. In certain embodiments the off-target gene is Pik3c2g. In certain embodiments the off-target gene is 1300010F03Rik. In certain embodiments the off-target gene is Apbb2. In certain embodiments the off-target gene is Mcph1. In certain embodiments the off-target gene is Sergef. In certain embodiments the off-target gene is Adcy9. In certain embodiments the off-target gene is Pkp4. In certain embodiments the off-target gene is Ascc3. In certain embodiments the off-target gene is Enpp2. In certain embodiments the off-target gene is Sel1l. In certain embodiments the off-target gene is Macrod1. In certain embodiments the off-target gene is Vti1a. In certain embodiments the off-target gene is Wdr7. In certain embodiments the off-target gene is 4932417H02Rik. In certain embodiments the off-target gene is Bach2. In certain embodiments the off-target gene is 0610012H03Rik. In certain embodiments the off-target gene is Adk. In certain embodiments the off-target gene is Dym. In certain embodiments the off-target gene is Pitpnm2. In certain embodiments the off-target gene is Slc41a2. In certain embodiments the off-target gene is Fgfr2. In certain embodiments the off-target gene is Bre. In certain embodiments the off-target gene is Gphn. In certain embodiments the off-target gene is Mical3. In certain embodiments the off-target gene is Fars2. In certain embodiments the off-target gene is Ap3b1. In certain embodiments the off-target gene is Vps13a. In certain embodiments the off-target gene is Skap2. In certain embodiments the off-target gene is Sds. In certain embodiments the off-target gene is Coval/// Enox2. In certain embodiments the off-target gene is Pitpnc1. In certain embodiments the off-target gene is Large. In certain embodiments the off-target gene is Lrba.

In certain embodiments the off-target gene is Atg10. In certain embodiments the off-target gene is Atp9b. In certain embodiments the off-target gene is Cask. In certain embodiments the off-target gene is Ppm1l. In certain embodiments the off-target gene is Alcam. In certain embodiments the off-target gene is Atg7. In certain embodiments the off-target gene is Nfia. In certain embodiments the off-target gene is Supt3h. In certain embodiments the off-target gene is Med27. In certain embodiments the off-target gene is Cgnl1. In certain embodiments the off-target gene is Dennd1a. In certain embodiments the off-target gene is Smoc1. In certain embodiments the off-target gene is Prkca. In certain embodiments the off-target gene is 2210408F21Rik. In certain embodiments the off-target gene is Map2k5. In certain embodiments the off-target gene is Dock4. In certain embodiments the off-target gene is LOC100036521. In certain embodiments the off-target gene is Sil1. In certain embodiments the off-target gene is Tbc1d22a. In certain embodiments the off-target gene is 2310009E04Rik. In certain embodiments the off-target gene is BC057079. In certain embodiments the off-target gene is Fhit. In certain embodiments the off-target gene is Uvrag. In certain embodiments the off-target gene is Dtnb. In certain embodiments the off-target gene is Fto. In certain embodiments the off-target gene is Immp2l.

In certain embodiments the off-target gene is 4932417H02Rik. In certain embodiments the off-target gene is mKIAA0919///Sec1512///Exoc6b. In certain embodiments the off-target gene is Fbxl17. In certain embodiments the off-target gene is Chn2. In certain embodiments the off-target gene is Fto. In certain embodiments the off-target gene is AK053274///mKIAA0532///Vps13b///AK049111. In certain embodiments the off-target gene is Lrba///Lba. In certain embodiments the off-target gene is Fars2. In certain embodiments the off-target gene is Pomt2. In certain embodiments the off-target gene is Wwc1. In certain embodiments the off-target gene is Atg10. In certain embodiments the off-target gene is Gng12. In certain embodiments the off-target gene is Smg6. In certain embodiments the off-target gene is 2310008H04Rik. In certain embodiments the off-target gene is Ptprk. In certain embodiments the off-target gene is Cadps2. In certain embodiments the off-target gene is Supt3h. In certain embodiments the off-target gene is St3gal3. In certain embodiments the off-target gene is Atg7. In certain embodiments the off-target gene is Fggy. In certain embodiments the off-target gene is Ube2e2. In certain embodiments the off-target gene is Immp2l. In certain embodiments the off-target gene is Bcas3. In certain embodiments the off-target gene is Mnat1. In certain embodiments the off-target gene is Itpr2. In certain embodiments the off-target gene is Adcy9. In certain embodiments the off-target gene is Slc17a2. In certain embodiments the off-target gene is Sergef. In certain embodiments the off-target gene is Smoc1. In certain embodiments the off-target gene is Dym. In certain embodiments the off-target gene is Nfia. In certain embodiments the off-target gene is Odz3. In certain embodiments the off-target gene is Enox2. In certain embodiments the off-target gene is Tbc1d5. In certain embodiments the off-target gene is BC057079. In certain embodiments the off-target gene is Cob1. In certain embodiments the off-target gene is Msi2. In certain embodiments the off-target gene is Esr1. In certain embodiments the off-target gene is Dexi. In certain embodiments the off-target gene is AA536749. In certain embodiments the off-target gene is Efna5. In certain embodiments the off-target gene is Med27. In certain embodiments the off-target gene is Cdka11. In certain embodiments the off-target gene is Atp9b. In certain embodiments the off-target gene is Igfbp4. In certain embodiments the off-target gene is Saa4. In certain embodiments the off-target gene is Fryl. In certain embodiments the off-target gene is Mical3///Kiaa0819.

In certain embodiments the off-target gene is Itpr1. In certain embodiments the off-target gene is AK031097///Ppm11. In certain embodiments the off-target gene is Pard3. In certain embodiments the off-target gene is Mgmt. In certain embodiments the off-target gene is Mtmr14. In certain embodiments the off-target gene is Pik3c2g. In certain embodiments the off-target gene is Fndc3b. In certain embodiments the off-target gene is Cask. In certain embodiments the off-target gene is Galnt10. In certain embodiments the off-target gene is Tbc1d22a. In certain embodiments the off-target gene is Macrod1. In certain embodiments the off-target gene is Clec16a. In certain embodiments the off-target gene is Dis3l2. In certain embodiments the off-target gene is Cyp2j9. In certain embodiments the off-target gene is Sntg2. In certain embodiments the off-target gene is Sil1. In certain embodiments the off-target gene is 1300010F03Rik. In certain embodiments the off-target gene is Cux1. In certain embodiments the off-target gene is 1110012L19Rik. In certain embodiments the off-target gene is Prnpip1. In certain embodiments the off-target gene is Atxn1. In certain embodiments the off-target gene is Gpr39. In certain embodiments the off-target gene is Ghr. In certain embodiments the off-target gene is Ptprd. In certain embodiments the off-target gene is Errfi1. In certain embodiments the off-target gene is AK137808///Gtdc1. In certain embodiments the off-target gene is Atp11c. In certain embodiments the off-target gene is Prkag2. In certain embodiments the off-target gene is Lrit1. In certain embodiments the off-target gene is Tnrc6b. In certain embodiments the off-target gene is Cgn11. In certain embodiments the off-target gene is Large. In certain embodiments the off-target gene is Gphn. In certain embodiments the off-target gene is Bbs9. In certain embodiments the off-target gene is Pcx. In certain embodiments the off-target gene is mKIAA1188///Clmn. In certain embodiments the off-target gene is Pet1121. In certain embodiments the off-target gene is Stxbp5. In certain embodiments the off-target gene is Ext2. In certain embodiments the off-target gene is Dtnbp1. In certain embodiments the off-target gene is Arsb. In certain embodiments the off-target gene is Zdhhc14. In certain embodiments the off-target gene is Mbnl2. In certain embodiments the off-target gene is Dtnb. In certain embodiments the off-target gene is Pitpnm2.

In certain embodiments the off-target gene is Herc2. In certain embodiments the off-target gene is Enpp2. In certain embodiments the off-target gene is Vti1a. In certain embodiments the off-target gene is Dock4///mKIAA0716. In certain embodiments the off-target gene is Dpyd. In certain embodiments the off-target gene is Arsg. In certain embodiments the off-target gene is Pcca. In certain embodiments the off-target gene is Snd1. In certain embodiments the off-target gene is Ccdc91. In certain embodiments the off-target gene is Acsm5. In certain embodiments the off-target gene is Gtf2i. In certain embodiments the off-target gene is Slc39a11. In certain embodiments the off-target gene is Adarb1. In certain embodiments the off-target gene is Pcnx. In certain embodiments the off-target gene is Zcchc7. In certain embodiments the off-target gene is Bbs4. In certain embodiments the off-target gene is Uroc1. In certain embodiments the off-target gene is Cdh2. In certain embodiments the off-target gene is Map2k2. In certain embodiments the off-target gene is BC038349. In certain embodiments the off-target gene is 5033414K04Rik. In certain embodiments the off-target gene is Epb4.1. In certain embodiments the off-target gene is Dock1. In certain embodiments the off-target gene is Pank1. In certain embodiments the off-target gene is Slc4a4. In certain embodiments the off-target gene is Tmtc2. In certain embodiments the off-target gene is Ncrna00153. In certain embodiments the off-target gene is BC099512. In certain embodiments the off-target gene is Farp1. In certain embodiments the off-target gene is Nfib. In certain embodiments the off-target gene is Arhgef11. In certain embodiments the off-target gene is Got1. In certain embodiments the off-target gene is Cables1. In certain embodiments the off-target gene is Elov15. In certain embodiments the off-target gene is Usp20. In certain embodiments the off-target gene is Myo9b. In certain embodiments the off-target gene is Nedd4l///mKIAA0439. In certain embodiments the off-target gene is 0610012H03Rik. In certain embodiments the off-target gene is D430042O09Rik. In certain embodiments the off-target gene is Ehbp1. In certain embodiments the off-target gene is Ttc7b. In certain embodiments the off-target gene is Sel11. In certain embodiments the off-target gene is Vps13a///CHAC.

In certain embodiments the off-target gene is Ddb2. In certain embodiments the off-target gene is Rnf213. In certain embodiments the off-target gene is Myo1e. In certain embodiments the off-target gene is Masp2. In certain embodiments the off-target gene is Gfra1. In certain embodiments the off-target gene is Hsd17b2. In certain embodiments the off-target gene is Rapgef6///mKIAA4052. In certain embodiments the off-target gene is Ascc3///AK144867. In certain embodiments the off-target gene is Prkca. In certain embodiments the off-target gene is Parva. In certain embodiments the off-target gene is Fert2. In certain embodiments the off-target gene is Stau2. In certain embodiments the off-target gene is Mapkap1. In certain embodiments the off-target gene is AK140547///Ralgps1. In certain embodiments the off-target gene is Sox5. In certain embodiments the off-target gene is Chdh. In certain embodiments the off-target gene is Smad3. In certain embodiments the off-target gene is Skap2. In certain embodiments the off-target gene is Mad1///Mad111. In certain embodiments the off-target gene is Pdzrn3. In certain embodiments the off-target gene is Arid1b. In certain embodiments the off-target gene is Aspg. In certain embodiments the off-target gene is Anxa6. In certain embodiments the off-target gene is Arfgef1. In certain embodiments the off-target gene is Hs6st1. In certain embodiments the off-target gene is Arhgap26///mKIAA0621. In certain embodiments the off-target gene is Wdr7.

In certain embodiments the off-target gene is B230342M21Rik///N4bp2l1. In certain embodiments the off-target gene is Asph. In certain embodiments the off-target gene is Iqgap2. In certain embodiments the off-target gene is Ugcg11. In certain embodiments the off-target gene is BC033915. In certain embodiments the off-target gene is mKIAA0665///Rab11fip3. In certain embodiments the off-target gene is Sox6. In certain embodiments the off-target gene is Fbxo31. In certain embodiments the off-target gene is Ubac2. In certain embodiments the off-target gene is Hmgn3. In certain embodiments the off-target gene is 4930402H24Rik. In certain embodiments the off-target gene is Foxp11. In certain embodiments the off-target gene is Cd9912. In certain embodiments the off-target gene is C530044N13Rik///Cpped1. In certain embodiments the off-target gene is Trappc9///1810044A24Rik. In certain embodiments the off-target gene is Rabgap11. In certain embodiments the off-target gene is Tbl1x. In certain embodiments the off-target gene is Hs2st1. In certain embodiments the off-target gene is Tmem16k///Ano10. In certain embodiments the off-target gene is Agap1. In certain embodiments the off-target gene is Map2k5. In certain embodiments the off-target gene is Susd4. In certain embodiments the off-target gene is Rbms1///AK011205. In certain embodiments the off-target gene is Gig18. In certain embodiments the off-target gene is 4933407C03Rik///mKIAA1694. In certain embodiments the off-target gene is Oaf. In certain embodiments the off-target gene is Cadm1. In certain embodiments the off-target gene is Tsc2. In certain embodiments the off-target gene is Zbtb20. In certain embodiments the off-target gene is Aig1. In certain embodiments the off-target gene is Zfp277///AK172713.

In certain embodiments the off-target gene is Nsmaf. In certain embodiments the off-target gene is Ppp1ca. In certain embodiments the off-target gene is Vav2. In certain embodiments the off-target gene is Mg11. In certain embodiments the off-target gene is Ppnr. In certain embodiments the off-target gene is 2310007H09Rik. In certain embodiments the off-target gene is Mll3. In certain embodiments the off-target gene is Peli2. In certain embodiments the off-target gene is Spag9///JSAP2. In certain embodiments the off-target gene is Ctnna1. In certain embodiments the off-target gene is Ostf1. In certain embodiments the off-target gene is 11-Sep. In certain embodiments the off-target gene is Man2a1. In certain embodiments the off-target gene is Nlk. In certain embodiments the off-target gene is AU040829. In certain embodiments the off-target gene is Apbb2. In certain embodiments the off-target gene is Nsmce2. In certain embodiments the off-target gene is Btbd9. In certain embodiments the off-target gene is Rap1gds1. In certain embodiments the off-target gene is Cryl1. In certain embodiments the off-target gene is Slco2a1. In certain embodiments the off-target gene is Ubr1. In certain embodiments the off-target gene is Lrrc16a///Lrrc16. In certain embodiments the off-target gene is Mon2. In certain embodiments the off-target gene is Fbxw7. In certain embodiments the off-target gene is Ppp3ca.

In certain embodiments the off-target gene is AK040794///Acaca. In certain embodiments the off-target gene is Man1a. In certain embodiments the off-target gene is Rbms3. In certain embodiments the off-target gene is Adipor2. In certain embodiments the off-target gene is Ryr3. In certain embodiments the off-target gene is Tpk1. In certain embodiments the off-target gene is Pepd. In certain embodiments the off-target gene is C2cd21. In certain embodiments the off-target gene is Akap7. In certain embodiments the off-target gene is BC030307. In certain embodiments the off-target gene is Fam149b. In certain embodiments the off-target gene is Spop. In certain embodiments the off-target gene is Xrcc4. In certain embodiments the off-target gene is Dip2c. In certain embodiments the off-target gene is 1700009P17Rik. In certain embodiments the off-target gene is Pdia5. In certain embodiments the off-target gene is Pck1. In certain embodiments the off-target gene is Vps53. In certain embodiments the off-target gene is Eefsec. In certain embodiments the off-target gene is Pbld. In certain embodiments the off-target gene is Dennd1a. In certain embodiments the off-target gene is Ncoa1. In certain embodiments the off-target gene is Fign.

In certain embodiments the off-target gene is 4933421E11Rik. In certain embodiments the off-target gene is Rpusd4. In certain embodiments the off-target gene is AK019895///Chchd8. In certain embodiments the off-target gene is Angel2. In certain embodiments the off-target gene is Thumpd3. In certain embodiments the off-target gene is Polr2d. In certain embodiments the off-target gene is Gadd45a. In certain embodiments the off-target gene is Ece2. In certain embodiments the off-target gene is 2310009B15Rik. In certain embodiments the off-target gene is 1110002N22Rik. In certain embodiments the off-target gene is Setd1a. In certain embodiments the off-target gene is 2810432D09Rik. In certain embodiments the off-target gene is Serbp1. In certain embodiments the off-target gene is 2310039H08Rik. In certain embodiments the off-target gene is Mtap1s. In certain embodiments the off-target gene is Plek2. In certain embodiments the off-target gene is Bola1. In certain embodiments the off-target gene is AK172713///9430016H08Rik. In certain embodiments the off-target gene is 1700052N19Rik. In certain embodiments the off-target gene is Rnf6. In certain embodiments the off-target gene is Thtpa. In certain embodiments the off-target gene is Ormdl1. In certain embodiments the off-target gene is 2900026A02Rik. In certain embodiments the off-target gene is Polr2a. In certain embodiments the off-target gene is Ywhah. In certain embodiments the off-target gene is Krt18. In certain embodiments the off-target gene is Zfp518b. In certain embodiments the off-target gene is Spryd4. In certain embodiments the off-target gene is 0610010K14Rik. In certain embodiments the off-target gene is AU021838///Mipol1. In certain embodiments the off-target gene is Adam32. In certain embodiments the off-target gene is 2810422O20Rik. In certain embodiments the off-target gene is Lgals3 bp. In certain embodiments the off-target gene is Ltv1. In certain embodiments the off-target gene is Fahd1. In certain embodiments the off-target gene is 0610007P22Rik. In certain embodiments the off-target gene is Sf3b4. In certain embodiments the off-target gene is Fermt2. In certain embodiments the off-target gene is Znhit3. In certain embodiments the off-target gene is Znf746. In certain embodiments the off-target gene is Trnau1ap. In certain embodiments the off-target gene is Rpl13. In certain embodiments the off-target gene is Rpl24. In certain embodiments the off-target gene is Pdgfa. In certain embodiments the off-target gene is Tmem41a. In certain embodiments the off-target gene is Cep78. In certain embodiments the off-target gene is Ilf2. In certain embodiments the off-target gene is 2510049J12Rik. In certain embodiments the off-target gene is Ap4b1. In certain embodiments the off-target gene is Ppp1r11. In certain embodiments the off-target gene is Arfgap2. In certain embodiments the off-target gene is Aldoc.

In certain embodiments the off-target gene is Hus1. In certain embodiments the off-target gene is Ppp2r1a. In certain embodiments the off-target gene is Setd6. In certain embodiments the off-target gene is AK036897///Trex1. In certain embodiments the off-target gene is Rpp38. In certain embodiments the off-target gene is Nars. In certain embodiments the off-target gene is Mrpl50. In certain embodiments the off-target gene is Mthfd2. In certain embodiments the off-target gene is 2010321M09Rik. In certain embodiments the off-target gene is Lrrc57. In certain embodiments the off-target gene is Cox18. In certain embodiments the off-target gene is Umps. In certain embodiments the off-target gene is Prdx3. In certain embodiments the off-target gene is Usp18. In certain embodiments the off-target gene is Isgf3g. In certain embodiments the off-target gene is Nol11. In certain embodiments the off-target gene is Brf2. In certain embodiments the off-target gene is Ppid. In certain embodiments the off-target gene is Myadm. In certain embodiments the off-target gene is Krt8. In certain embodiments the off-target gene is Avpi1. In certain embodiments the off-target gene is Rab3d. In certain embodiments the off-target gene is Hn1. In certain embodiments the off-target gene is Ino80b. In certain embodiments the off-target gene is 2310016C08Rik. In certain embodiments the off-target gene is Gtf3a. In certain embodiments the off-target gene is Srrt. In certain embodiments the off-target gene is Nsbp1. In certain embodiments the off-target gene is Polr2h. In certain embodiments the off-target gene is Tomm5. In certain embodiments the off-target gene is Slc1a4. In certain embodiments the off-target gene is Bxdc2. In certain embodiments the off-target gene is Gemin4. In certain embodiments the off-target gene is Gbl. In certain embodiments the off-target gene is C87414///AA792892. In certain embodiments the off-target gene is AK052711. In certain embodiments the off-target gene is Ddx52. In certain embodiments the off-target gene is Commd3. In certain embodiments the off-target gene is Shmt2. In certain embodiments the off-target gene is Tmem97. In certain embodiments the off-target gene is Sp5. In certain embodiments the off-target gene is Gar1. In certain embodiments the off-target gene is Esco2. In certain embodiments the off-target gene is 2310047B19Rik. In certain embodiments the off-target gene is Pop7.

In certain embodiments the off-target gene is Plrg1. In certain embodiments the off-target gene is Cct4. In certain embodiments the off-target gene is Cc19. In certain embodiments the off-target gene is Pnp1. In certain embodiments the off-target gene is Etaa1. In certain embodiments the off-target gene is Prss8. In certain embodiments the off-target gene is Rce1. In certain embodiments the off-target gene is Usp22. In certain embodiments the off-target gene is Ruvbl2. In certain embodiments the off-target gene is Impdh2. In certain embodiments the off-target gene is Npb. In certain embodiments the off-target gene is Exosc2. In certain embodiments the off-target gene is Dus41. In certain embodiments the off-target gene is 1700029J07Rik. In certain embodiments the off-target gene is 1700123O20Rik. In certain embodiments the off-target gene is Nudt2. In certain embodiments the off-target gene is Gltpd1. In certain embodiments the off-target gene is Dbr1. In certain embodiments the off-target gene is Ins16. In certain embodiments the off-target gene is Rps4x. In certain embodiments the off-target gene is Ccdc51. In certain embodiments the off-target gene is Mrto4. In certain embodiments the off-target gene is Gde1. In certain embodiments the off-target gene is Hexim2. In certain embodiments the off-target gene is Atmin. In certain embodiments the off-target gene is Msl1. In certain embodiments the off-target gene is Qars. In certain embodiments the off-target gene is Dak. In certain embodiments the off-target gene is Ccrk. In certain embodiments the off-target gene is Armc6. In certain embodiments the off-target gene is 2810008M24Rik. In certain embodiments the off-target gene is Kdelc1///1700029F09Rik. In certain embodiments the off-target gene is Srd5a3. In certain embodiments the off-target gene is Hirip3. In certain embodiments the off-target gene is A430005L14Rik. In certain embodiments the off-target gene is BC026590. In certain embodiments the off-target gene is Cldn3///Wbscr25.

In certain embodiments the off-target gene is Zfp637. In certain embodiments the off-target gene is Fen1. In certain embodiments the off-target gene is Alg5. In certain embodiments the off-target gene is Als2cr2///Stradb.

In certain embodiments the off-target gene is Rpl29. In certain embodiments the off-target gene is Tmub1. In certain embodiments the off-target gene is Rpl8. In certain embodiments the off-target gene is Zfp161. In certain embodiments the off-target gene is D4Wsu114e. In certain embodiments the off-target gene is Ddx28. In certain embodiments the off-target gene is Npm1. In certain embodiments the off-target gene is Nkrf. In certain embodiments the off-target gene is 1110058L19Rik. In certain embodiments the off-target gene is Snapc4. In certain embodiments the off-target gene is Nme3. In certain embodiments the off-target gene is Peo1. In certain embodiments the off-target gene is Rpl19. In certain embodiments the off-target gene is Pbx2. In certain embodiments the off-target gene is 2210411K11Rik. In certain embodiments the off-target gene is Rps10. In certain embodiments the off-target gene is Rps8. In certain embodiments the off-target gene is No16. In certain embodiments the off-target gene is Rps21. In certain embodiments the off-target gene is Hsd3b4. In certain embodiments the off-target gene is Parp16. In certain embodiments the off-target gene is Palm. In certain embodiments the off-target gene is Trip6. In certain embodiments the off-target gene is Acot6. In certain embodiments the off-target gene is Abhd14a. In certain embodiments the off-target gene is Mrpl40. In certain embodiments the off-target gene is Rps12. In certain embodiments the off-target gene is Ptrh2. In certain embodiments the off-target gene is Trim21. In certain embodiments the off-target gene is Necap1. In certain embodiments the off-target gene is Ythdc1. In certain embodiments the off-target gene is Gpn3. In certain embodiments the off-target gene is Sfrs6. In certain embodiments the off-target gene is ENSMUSG00000059775///Rps26. In certain embodiments the off-target gene is Nup43. In certain embodiments the off-target gene is Rnps1. In certain embodiments the off-target gene is Psip1. In certain embodiments the off-target gene is Btbd6. In certain embodiments the off-target gene is Cdkn2aipnl. In certain embodiments the off-target gene is Rpl7. In certain embodiments the off-target gene is Eif2b4. In certain embodiments the off-target gene is Psma4. In certain embodiments the off-target gene is Zscan12. In certain embodiments the off-target gene is Rpl31. In certain embodiments the off-target gene is Kbtbd7. In certain embodiments the off-target gene is Dtwd1. In certain embodiments the off-target gene is 4930473A06Rik///AK029637. In certain embodiments the off-target gene is Mfap3. In certain embodiments the off-target gene is Ccdc130. In certain embodiments the off-target gene is Cdc34. In certain embodiments the off-target gene is Ifi30. In certain embodiments the off-target gene is Chac2. In certain embodiments the off-target gene is Ufsp1.

In certain embodiments the off-target gene is Gemin6. In certain embodiments the off-target gene is Igtp. In certain embodiments the off-target gene is Ankrd49. In certain embodiments the off-target gene is AK206957///AK050697. In certain embodiments the off-target gene is Ccdc32. In certain embodiments the off-target gene is ENSMUSG00000053178. In certain embodiments the off-target gene is Rccd1. In certain embodiments the off-target gene is Med11. In certain embodiments the off-target gene is 2810416G20Rik. In certain embodiments the off-target gene is F8a. In certain embodiments the off-target gene is Adat2. In certain embodiments the off-target gene is Sat1. In certain embodiments the off-target gene is Zcchc8. In certain embodiments the off-target gene is Pnrc2. In certain embodiments the off-target gene is Tmem129. In certain embodiments the off-target gene is Mrps22. In certain embodiments the off-target gene is 4930572J05Rik. In certain embodiments the off-target gene is Rpl12. In certain embodiments the off-target gene is Ino80c. In certain embodiments the off-target gene is Cdca7. In certain embodiments the off-target gene is Usp11. In certain embodiments the off-target gene is BC031781. In certain embodiments the off-target gene is 2200002D01Rik. In certain embodiments the off-target gene is Hexim1. In certain embodiments the off-target gene is Thns11.

In certain embodiments the off-target gene is AK009724. In certain embodiments the off-target gene is Thyn1///mThy28. In certain embodiments the off-target gene is Prpf6. In certain embodiments the off-target gene is Med21. In certain embodiments the off-target gene is Wbp5. In certain embodiments the off-target gene is Iars. In certain embodiments the off-target gene is Mfsd10. In certain embodiments the off-target gene is Nt5dc2. In certain embodiments the off-target gene is 2010003K11Rik. In certain embodiments the off-target gene is Rpp21. In certain embodiments the off-target gene is Gimap1. In certain embodiments the off-target gene is Rassf7. In certain embodiments the off-target gene is Scrn2. In certain embodiments the off-target gene is Cd3eap. In certain embodiments the off-target gene is Ccdc85b. In certain embodiments the off-target gene is AK087382. In certain embodiments the off-target gene is Psmg1. In certain embodiments the off-target gene is Atic. In certain embodiments the off-target gene is Tmem179b. In certain embodiments the off-target gene is Kbtbd4. In certain embodiments the off-target gene is Tmem60. In certain embodiments the off-target gene is 2810026P18Rik. In certain embodiments the off-target gene is Zfp213. In certain embodiments the off-target gene is Psmg2. In certain embodiments the off-target gene is AA881470. In certain embodiments the off-target gene is Eef1d. In certain embodiments the off-target gene is Chchd5. In certain embodiments the off-target gene is Ube2l6. In certain embodiments the off-target gene is Gstm4. In certain embodiments the off-target gene is Taf1a. In certain embodiments the off-target gene is Slc26a1. In certain embodiments the off-target gene is Eral1. In certain embodiments the off-target gene is Mrpl15///AK017820. In certain embodiments the off-target gene is Ccdc23. In certain embodiments the off-target gene is Fbl. In certain embodiments the off-target gene is C130022K22Rik. In certain embodiments the off-target gene is LOC554292. In certain embodiments the off-target gene is Mrps18b. In certain embodiments the off-target gene is Tmem177. In certain embodiments the off-target gene is Brp16. In certain embodiments the off-target gene is Tlcd2. In certain embodiments the off-target gene is Rdh14. In certain embodiments the off-target gene is Tmem185b. In certain embodiments the off-target gene is Rpl35. In certain embodiments the off-target gene is Mrpl11. In certain embodiments the off-target gene is Ythdf2. In certain embodiments the off-target gene is Pdcd2. In certain embodiments the off-target gene is Eif2s3x. In certain embodiments the off-target gene is Aldoa.

In certain embodiments the off-target gene is Kat2a. In certain embodiments the off-target gene is Rdm1. In certain embodiments the off-target gene is Rplp2. In certain embodiments the off-target gene is 2610301G19Rik. In certain embodiments the off-target gene is Rpl13. In certain embodiments the off-target gene is Tnnc1. In certain embodiments the off-target gene is Pgam1. In certain embodiments the off-target gene is Smug1. In certain embodiments the off-target gene is 2310004I24Rik. In certain embodiments the off-target gene is Sap30. In certain embodiments the off-target gene is 1500012F01Rik. In certain embodiments the off-target gene is Sf3b3. In certain embodiments the off-target gene is Tagap///Tagap1. In certain embodiments the off-target gene is Ripk4. In certain embodiments the off-target gene is BC160215///Ids. In certain embodiments the off-target gene is Cbr4. In certain embodiments the off-target gene is Usp42. In certain embodiments the off-target gene is Trp53. In certain embodiments the off-target gene is Psmb6. In certain embodiments the off-target gene is Tapbp1. In certain embodiments the off-target gene is Jtv1. In certain embodiments the off-target gene is Khsrp. In certain embodiments the off-target gene is Oasl1. In certain embodiments the off-target gene is Hgs. In certain embodiments the off-target gene is Rps20. In certain embodiments the off-target gene is H2afx. In certain embodiments the off-target gene is Psmb4. In certain embodiments the off-target gene is Tgm1. In certain embodiments the off-target gene is Daxx. In certain embodiments the off-target gene is Clk2///Scamp3. In certain embodiments the off-target gene is Sfrs7. In certain embodiments the off-target gene is Slc35a4. In certain embodiments the off-target gene is Chtf8. In certain embodiments the off-target gene is Fiz1. In certain embodiments the off-target gene is Snrnp25. In certain embodiments the off-target gene is Tax1bp1. In certain embodiments the off-target gene is Rcan3. In certain embodiments the off-target gene is Scnm1. In certain embodiments the off-target gene is Coi1. In certain embodiments the off-target gene is Cog8. In certain embodiments the off-target gene is Cdk4. In certain embodiments the off-target gene is Lsm2. In certain embodiments the off-target gene is Klf6. In certain embodiments the off-target gene is Cct8. In certain embodiments the off-target gene is Tmem107. In certain embodiments the off-target gene is Noc2l. In certain embodiments the off-target gene is Armc10. In certain embodiments the off-target gene is C430004E15Rik. In certain embodiments the off-target gene is Rangrf. In certain embodiments the off-target gene is Kbtbd2. In certain embodiments the off-target gene is Impact. In certain embodiments the off-target gene is Rnmtl1. In certain embodiments the off-target gene is Fnta. In certain embodiments the off-target gene is Srxn1. In certain embodiments the off-target gene is Rpp14. In certain embodiments the off-target gene is AK003073. In certain embodiments the off-target gene is Rpl15.

In certain embodiments the off-target gene is ENSMUSG00000074747. In certain embodiments the off-target gene is Casp2. In certain embodiments the off-target gene is 6330503K22Rik. In certain embodiments the off-target gene is Xaf1. In certain embodiments the off-target gene is Pus1. In certain embodiments the off-target gene is Rnf187. In certain embodiments the off-target gene is 2610024G14Rik. In certain embodiments the off-target gene is Mrps23. In certain embodiments the off-target gene is Mat2a. In certain embodiments the off-target gene is Eif5. In certain embodiments the off-target gene is Fem1b. In certain embodiments the off-target gene is Rpl18. In certain embodiments the off-target gene is Mrps30. In certain embodiments the off-target gene is Rpl28. In certain embodiments the off-target gene is Otub1. In certain embodiments the off-target gene is Mapk6. In certain embodiments the off-target gene is Tlr6. In certain embodiments the off-target gene is Rps24. In certain embodiments the off-target gene is Eif4a1. In certain embodiments the off-target gene is Pigp. In certain embodiments the off-target gene is Rars. In certain embodiments the off-target gene is Pyroxd1. In certain embodiments the off-target gene is Pabpc4. In certain embodiments the off-target gene is Rps19. In certain embodiments the off-target gene is Mrps16. In certain embodiments the off-target gene is Abcf2. In certain embodiments the off-target gene is Rilp12. In certain embodiments the off-target gene is Thoc1. In certain embodiments the off-target gene is Gpatch4. In certain embodiments the off-target gene is AK009175. In certain embodiments the off-target gene is Eif2b2.

C. Methods of Predicting In Vitro or In Vivo Toxicity

In certain embodiments, a computer or any other means may be used to determine the amount of sequence complementarity between the nucleobase sequence of any oligomeric compound and the nucleobase sequence of any off-target gene. In certain embodiments, a computer or any other means may be used to determine the amount of sequence complementarity between the nucleobase sequence of any oligomeric compound and the nucleobase sequence of any sentinel gene. In certain embodiments, oligomeric compounds having high amounts of complementarity between their nucleobase sequence and any number of off-target genes and/or sentinel genes may indicate toxicity. In certain embodiments, one having skill in the art may select a minimum amount of complementarity between the nucleobase sequence of the oligomeric compound and the nucleobase sequence of any given off-target gene and/or sentinel gene. In certain embodiments, the nucleobase sequence of an oligomeric compound may have 90% complementarity with the nucleobase sequence of an off-target gene and/or sentinel gene. In certain embodiments, the nucleobase sequence of an oligomeric compound may have 100% complementarity with the nucleobase sequence of an off-target gene and/or sentinel gene.

In certain embodiments, the nucleobase sequence of an oligomeric compound may have 1 to 2 mismatches relative to the nucleobase sequence of an off-target gene and/or sentinel gene. In certain embodiments, the nucleobase sequence of an oligomeric compound may have 1 mismatch relative to the nucleobase sequence of an off-target gene and/or sentinel gene. In certain embodiments, the nucleobase sequence of an oligomeric compound may have 2 mismatches relative to the nucleobase sequence of an off-target gene and/or sentinel gene.

In certain embodiments, after one having skill in the art has selected a minimum amount of complementarity between the nucleobase sequence of the oligomeric compound and the nucleobase sequence of any given off-target gene and/or sentinel gene, the number of off-target genes and/or sentinel genes in a genome having an equal to or greater amount of complementarity with the oligomeric compound may be identified. In certain embodiments, before one having skill in the art has selected a minimum amount of complementarity between the nucleobase sequence of the oligomeric compound and the nucleobase sequence of any given off-target gene and/or sentinel gene, the total number of off-target genes and/or sentinel genes in a genome having an equal to or greater amount of complementarity with the oligomeric compound may be identified. In some embodiments, a computer is used to identify the number of off-target genes and/or sentinel gene in a genome that have an equal to or greater amount of complementarity with the oligomeric compound.

In certain embodiments, the total number of off-target genes and/or sentinel genes having an equal to or greater amount of complementarity with the oligomeric compound may be identified. In certain embodiments, the greater the number of off-target genes and/or sentinel genes having an equal to or greater amount of complementarity with the oligomeric compound indicates greater probability of in vitro and in vivo toxicity.

D. Oligomeric Compounds

Certain methods disclosed herein provide for the identification of oligomeric compounds. In certain embodiments, the methods disclosed herein may be used to discover novel non-toxic oligomeric compounds. In certain embodiments, the methods disclosed herein may be used to discover novel non-toxic oligomer modifications or oligomer motifs. In certain embodiments, at least one oligomeric compounds that is predicted not to be toxic in vivo is made and then tested in an animal.

In certain embodiments, the present invention provides oligomeric compounds. In certain embodiments, such oligomeric compounds comprise oligonucleotides optionally comprising one or more conjugate and/or terminal groups. In certain embodiments, an oligomeric compound consists of an oligonucleotide. In certain embodiments, oligonucleotides comprise one or more chemical modifications. Such chemical modifications include modifications of one or more nucleoside (including modifications to the sugar moiety and/or the nucleobase) and/or modifications to one or more internucleoside linkage.

a. Certain Modified Nucleosides

In certain embodiments, provided herein are oligomeric compounds comprising or consisting of oligonuleotides comprising at least one modified nucleoside. Such modified nucleosides comprise a modified sugar moeity, a modified nucleobase, or both a modified sugar moiety and a modified nucleobase.

i. Certain Modified Sugar Moieties

In certain embodiments, compounds of the invention comprise one or more modified nucleosides comprising a modified sugar moiety. Such compounds comprising one or more sugar-modified nucleosides may have desirable properties, such as enhanced nuclease stability or increased binding affinity with a target nucleic acid relative to an oligonucleotide comprising only nucleosides comprising naturally occurring sugar moieties. In certain embodiments, modified sugar moieties are substituted sugar moieties. In certain embodiments, modified sugar moieties are sugar surrogates. Such sugar surrogates may comprise one or more substitutions corresponding to those of substituted sugar moieties.

In certain embodiments, modified sugar moieties are substituted sugar moieties comprising one or more non-bridging sugar substituent, including but not limited to substituents at the 2' and/or 5' positions. Examples of sugar substituents suitable for the 2'-position, include, but are not limited to: 2'-F, 2'-OCH$_3$ ("OMe" or "O-methyl"), and 2'-O(CH$_2$)$_2$OCH$_3$ ("MOE"). In certain embodiments, sugar substituents at the 2' position is selected from allyl, amino, azido, thio, O-allyl, O—C$_1$-C$_{10}$ alkyl, O—C$_1$-C$_{10}$ substituted alkyl; OCF$_3$, O(CH$_2$)$_2$SCH$_3$, O(CH$_2$)$_2$—O—N(Rm)(Rn), and O—CH$_2$—C(=O)—N(Rm)(Rn), where each Rm and Rn is, independently, H or substituted or unsubstituted C$_1$-C$_{10}$ alkyl. Examples of sugar substituents at the 5'-position, include, but are not limited to: 5'-methyl (R or S); 5'-vinyl, and 5'-methoxy. In certain embodiments, substituted sugars comprise more than one non-bridging sugar substituent, for example, 2'-F-5'-methyl sugar moieties (see, e.g., PCT International Application WO 2008/101157, for additional 5',2'-bis substituted sugar moieties and nucleosides).

Nucleosides comprising 2'-substituted sugar moieties are referred to as 2'-substituted nucleosides. In certain embodiments, a 2'-substituted nucleoside comprises a 2'-substituent group selected from halo, allyl, amino, azido, SH, CN, OCN, $CF_3$, $OCF_3$, O, S, or $N(R_m)$-alkyl; O, S, or $N(R_m)$-alkenyl; O, S or $N(R_m)$-alkynyl; O-alkylenyl-O-alkyl, alkynyl, alkaryl, aralkyl, O-alkaryl, O-aralkyl, $O(CH_2)_2SCH_3$, $O—(CH_2)_2—O—N(R_m)(R_n)$ or $O—CH_2—C(=O)—N(R_m)(R_n)$, where each $R_m$ and $R_n$ is, independently, H, an amino protecting group or substituted or unsubstituted $C_1$-$C_{10}$ alkyl. These 2'-substituent groups can be further substituted with one or more substituent groups independently selected from hydroxyl, amino, alkoxy, carboxy, benzyl, phenyl, nitro ($NO_2$), thiol, thioalkoxy (S-alkyl), halogen, alkyl, aryl, alkenyl and alkynyl.

In certain embodiments, a 2'-substituted nucleoside comprises a 2'-substituent group selected from F, $NH_2$, $N_3$, $OCF_3$, $O—CH_3$, $O(CH_2)_3NH_2$, $CH_2—CH=CH_2$, $O—CH_2—CH=CH_2$, $OCH_2CH_2OCH_3$, $O(CH_2)_2SCH_3$, $O—(CH_2)_2—O—N(R_m)(R_n)$, $O(CH_2)_2O(CH_2)_2N(CH_3)_2$, and N-substituted acetamide ($O—CH_2—C(=O)—N(R_m)(R_n)$) where each $R_m$ and $R_n$ is, independently, H, an amino protecting group or substituted or unsubstituted $C_1$-$C_{10}$ alkyl.

In certain embodiments, a 2'-substituted nucleoside comprises a sugar moiety comprising a 2'-substituent group selected from F, $OCF_3$, $O—CH_3$, $OCH_2CH_2OCH_3$, $O(CH_2)_2SCH_3$, $O—(CH_2)_2—O—N(CH_3)_2$, $—O(CH_2)_2O(CH_2)_2N(CH_3)_2$, and $O—CH_2—C(=O)—N(H)CH_3$.

In certain embodiments, a 2'-substituted nucleoside comprises a sugar moiety comprising a 2'-substituent group selected from F, $O—CH_3$, and $OCH_2CH_2OCH_3$.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' sugar substituents, include, but are not limited to: $—[C(R_a)(R_b)]_n—$, $—[C(R_a)(R_b)]_n—O—$, $—C(R_aR_b)—N(R)—O—$ or, $—C(R_aR_b)—O—N(R)—$; 4'-$CH_2$-2', 4'-$(CH_2)_2$-2', 4'-$(CH_2)_3$-2', 4'-$(CH_2)—O-2'$ (LNA); 4'-$(CH_2)—S-2'$; 4'-$(CH_2)_2—O-2'$ (ENA); 4'-$CH(CH_3)—O-2'$ (cEt) and 4'-$CH(CH_2OCH_3)—O-2'$, and analogs thereof (see, e.g., U.S. Pat. No. 7,399,845, issued on Jul. 15, 2008); 4'-$C(CH_3)(CH_3)—O-2'$ and analogs thereof, (see, e.g., WO2009/006478, published Jan. 8, 2009); 4'-$CH_2—N(OCH_3)-2'$ and analogs thereof (see, e.g., WO2008/150729, published Dec. 11, 2008); 4'-$CH_2—O—N(CH_3)-2'$ (see, e.g., US2004/0171570, published Sep. 2, 2004); 4'-$CH_2—O—N(R)-2'$, and 4'-$CH_2—N(R)-0-2'$-, wherein each R is, independently, H, a protecting group, or $C_1$-$C_{12}$ alkyl; 4'-$CH_2—N(R)—O-2'$, wherein R is H, $C_1$-$C_{12}$ alkyl, or a protecting group (see, U.S. Pat. No. 7,427,672, issued on Sep. 23, 2008); 4'-$CH_2—C(H)(CH_3)-2'$ (see, e.g., Chattopadhyaya, et al., *J. Org. Chem.*, 2009, 74, 118-134); and 4'-$CH_2—C(=CH_2)-2'$ and analogs thereof (see, published PCT International Application WO 2008/154401, published on Dec. 8, 2008).

In certain embodiments, such 4' to 2' bridges independently comprise from 1 to 4 linked groups independently selected from $—[C(R_a)(R_b)]_n—$, $—C(R_a)=C(R_b)—$, $—C(R_a)=N—$, $—C(=NR_a)—$, $—C(=O)—$, $—C(=S)—$, $—O—$, $—Si(R_a)_2—$, $—S(=O)_x—$, and $—N(R_a)—$;

wherein:
x is 0, 1, or 2;
n is 1, 2, 3, or 4;
each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl ($S(=O)_2$-$J_1$), or sulfoxyl ($S(=O)$-$J_1$); and
each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl, or a protecting group.

Nucleosides comprising bicyclic sugar moieties are referred to as bicyclic nucleosides or BNAs. Bicyclic nucleosides include, but are not limited to, (A) α-L-Methyleneoxy (4'-$CH_2$—O-2') BNA, (B) β-D-Methyleneoxy (4'-$CH_2$—O-2') BNA (also referred to as locked nucleic acid or LNA), (C) Ethyleneoxy (4'-$(CH_2)_2$—O-2') BNA, (D) Aminooxy (4'-$CH_2$—O—N(R)-2') BNA, (E) Oxyamino (4'-$CH_2$—N(R)—O-2') BNA, (F) Methyl(methyleneoxy) (4'-$CH(CH_3)$—O-2') BNA (also referred to as constrained ethyl or cEt), (G) methylene-thio (4'-$CH_2$—S-2') BNA, (H) methylene-amino (4'-$CH_2$—N(R)-2') BNA, (I) methyl carbocyclic (4'-$CH_2$—CH($CH_3$)-2') BNA, (J) propylene carbocyclic (4'-$(CH_2)_3$-2') BNA, and (K) Ethylene(methoxy) (4'-(CH($CH_2$OMe)-O-2') BNA (also referred to as constrained MOE or cMOE) as depicted below.

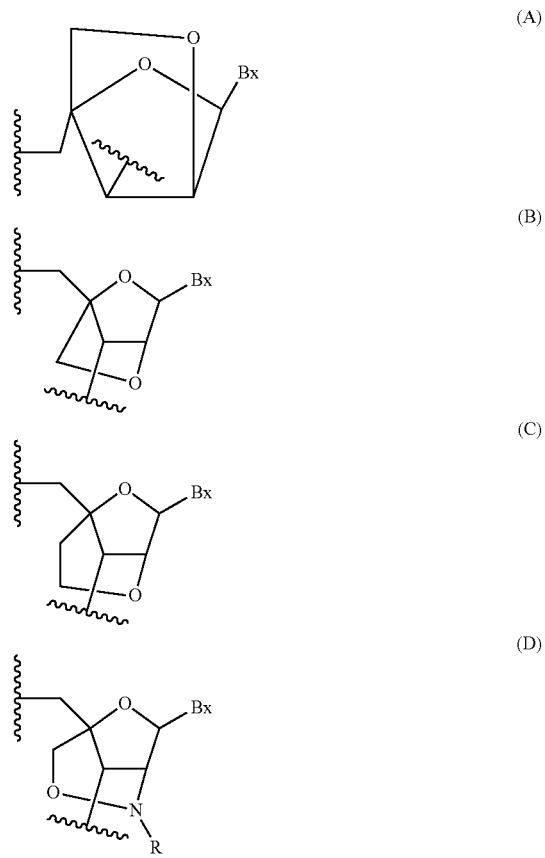

(A)

(B)

(C)

(D)

-continued

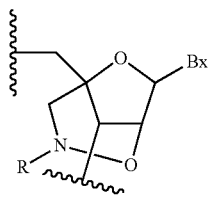 (E)

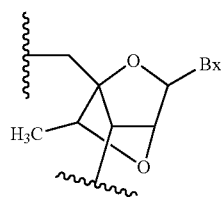 (F)

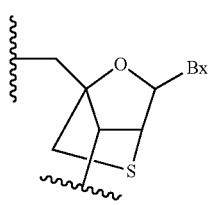 (G)

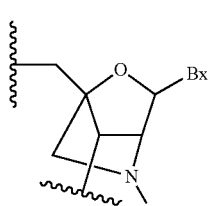 (H)

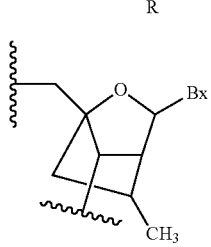 (I)

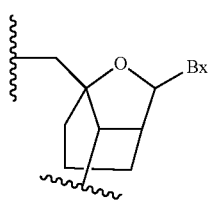 (J)

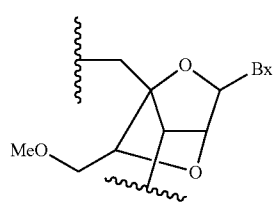 (K)

wherein Bx is a nucleobase moiety and R is, independently, H, a protecting group, or $C_1$-$C_{12}$ alkyl.

Additional bicyclic sugar moieties are known in the art, for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A.*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 129(26) 8362-8379 (Jul. 4, 2007); Elayadi et al., *Curr. Opinion Invens. Drugs*, 2001, 2, 558-561; Braasch et al., *Chem. Biol.*, 2001, 8, 1-7; Orum et al., *Curr. Opinion Mol. Ther.*, 2001, 3, 239-243; U.S. Pat. Nos. 7,053,207, 6,268,490, 6,770,748, 6,794,499, 7,034,133, 6,525,191, 6,670,461, and 7,399,845; WO 2004/106356, WO 1994/14226, WO 2005/021570, and WO 2007/134181; U.S. Patent Publication Nos. US2004/0171570, US2007/0287831, and US2008/0039618; U.S. patent Ser. Nos. 12/129,154, 60/989,574, 61/026,995, 61/026,998, 61/056,564, 61/086,231, 61/097,787, and 61/099,844; and PCT International Applications Nos. PCT/US2008/064591, PCT/US2008/066154, and PCT/US2008/068922.

In certain embodiments, bicyclic sugar moieties and nucleosides incorporating such bicyclic sugar moieties are further defined by isomeric configuration. For example, a nucleoside comprising a 4'-2' methylene-oxy bridge, may be in the α-L configuration or in the β-D configuration. Previously, α-L-methyleneoxy (4'-$CH_2$—O-2') bicyclic nucleosides have been incorporated into antisense oligonucleotides that showed antisense activity (Frieden et al., *Nucleic Acids Research*, 2003, 21, 6365-6372).

In certain embodiments, substituted sugar moieties comprise one or more non-bridging sugar substituent and one or more bridging sugar substituent (e.g., 5'-substituted and 4'-2' bridged sugars). (see, PCT International Application WO 2007/134181, published on Nov. 22, 2007, wherein LNA is substituted with, for example, a 5'-methyl or a 5'-vinyl group).

In certain embodiments, modified sugar moieties are sugar surrogates. In certain such embodiments, the oxygen atom of the naturally occurring sugar is substituted, e.g., with a sulfur, carbon or nitrogen atom. In certain such embodiments, such modified sugar moiety also comprises bridging and/or non-bridging substituents as described above. For example, certain sugar surrogates comprise a 4'-sulfur atom and a substitution at the 2'-position (see, e.g., published U.S. Patent Application US2005/0130923, published on Jun. 16, 2005) and/or the 5' position. By way of additional example, carbocyclic bicyclic nucleosides having a 4'-2' bridge have been described (see, e.g., Freier et al., *Nucleic Acids Research*, 1997, 25(22), 4429-4443 and Albaek et al., *J. Org. Chem.*, 2006, 71, 7731-7740).

In certain embodiments, sugar surrogates comprise rings having other than 5-atoms. For example, in certain embodiments, a sugar surrogate comprises a six-membered tetrahydropyran. Such tetrahydropyrans may be further modified or substituted. Nucleosides comprising such modified tetrahydropyrans include, but are not limited to, hexitol nucleic acid (HNA), anitol nucleic acid (ANA), manitol nucleic acid (MNA) (see Leumann, C J. *Bioorg. & Med. Chem.* (2002) 10:841-854), fluoro HNA (F-HNA), and those compounds having Formula VII:

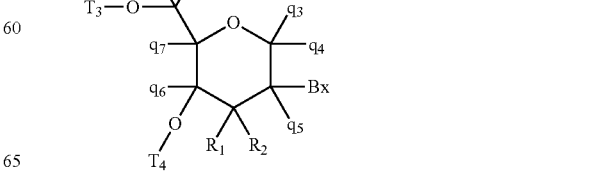

VII wherein independently for each of said at least one tetrahydropyran nucleoside analog of Formula VII:

Bx is a nucleobase moiety;

$T_3$ and $T_4$ are each, independently, an internucleoside linking group linking the tetrahydropyran nucleoside analog to the antisense compound or one of $T_3$ and $T_4$ is an internucleoside linking group linking the tetrahydropyran nucleoside analog to the antisense compound and the other of $T_3$ and $T_4$ is H, a hydroxyl protecting group, a linked conjugate group, or a 5' or 3'-terminal group;

$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H.

Many other bicyclo and tricyclo sugar surrogate ring systems are also known in the art that can be used to modify nucleosides for incorporation into antisense compounds (see, e.g., review article: Leumann, J. C, *Bioorganic & Medicinal Chemistry*, 2002, 10, 841-854).

Combinations of modifications are also provided without limitation, such as 2'-F-5'-methyl substituted nucleosides (see PCT International Application WO 2008/101157 Published on Aug. 21, 2008 for other disclosed 5',2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-$CH_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

In certain embodiments, the present invention provides oligonucleotides comprising modified nucleosides. Those modified nucleotides may include modified sugars, modified nucleobases, and/or modified linkages. The specific modifications are selected such that the resulting oligonucleotides possess desirable characteristics. In certain embodiments, oligonucleotides comprise one or more RNA-like nucleosides. In certain embodiments, oligonucleotides comprise one or more DNA-like nucleotides.

b. Certain Modified Nucleobases

In certain embodiments, nucleosides of the present invention comprise one or more unmodified nucleobases. In certain embodiments, nucleosides of the present invention comprise one or more modified nucleobases.

In certain embodiments, modified nucleobases are selected from: universal bases, hydrophobic bases, promiscuous bases, size-expanded bases, and fluorinated bases as defined herein. 5-substituted pyrimidines, 6-azapyrimidines and N-2, N-6 and O-6 substituted purines, including 2-aminopropyladenine, 5-propynyluracil; 5-propynylcytosine; 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine([5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, Kroschwitz, J. I., Ed., John Wiley & Sons, 1990, 858-859; those disclosed by Englisch et al., *Angewandte Chemie*, International Edition, 1991, 30, 613; and those disclosed by Sanghvi, Y. S., Chapter 15, *Antisense Research and Applications*, Crooke, S. T. and Lebleu, B., Eds., CRC Press, 1993, 273-288.

Representative United States patents that teach the preparation of certain of the above noted modified nucleobases as well as other modified nucleobases include without limitation, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096, certain of which are commonly owned with the instant application, and each of which is herein incorporated by reference in its entirety.

c. Certain Internucleoside Linkages

In certain embodiments, nucleosides may be linked together using any internucleoside linkage to form oligonucleotides. The two main classes of internucleoside linking groups are defined by the presence or absence of a phosphorus atom. Representative phosphorus containing internucleoside linkages include, but are not limited to, phosphodiesters (P=O), phosphotriesters, methylphosphonates, phosphoramidate, and phosphorothioates (P=S). Representative non-phosphorus containing internucleoside linking groups include, but are not limited to, methylenemethylimino (—$CH_2$—N($CH_3$)—O—$CH_2$—), thiodiester (—O—C(O)—S—), thionocarbamate (—O—C(O)(NH)—S—); siloxane (—O—Si(H)$_2$—O—); and N,N'-dimethylhydrazine (—$CH_2$—N($CH_3$)—N($CH_3$)—). Modified linkages, compared to natural phosphodiester linkages, can be used to alter, typically increase, nuclease resistance of the oligonucleotide. In certain embodiments, internucleoside linkages having a chiral atom can be prepared as a racemic mixture, or as separate enantiomers. Representative chiral linkages include, but are not limited to, alkylphosphonates and phosphorothioates. Methods of preparation of phosphorous-containing and non-phosphorous-containing internucleoside linkages are well known to those skilled in the art.

The oligonucleotides described herein contain one or more asymmetric centers and thus give rise to enantiomers, diastereomers, and other stereoisomeric configurations that may be defined, in terms of absolute stereochemistry, as (R) or (S), α or β such as for sugar anomers, or as (D) or (L) such as for amino acids etc. Included in the antisense compounds provided herein are all such possible isomers, as well as their racemic and optically pure forms.

Neutral internucleoside linkages include without limitation, phosphotriesters, methylphosphonates, MMI (3'-$CH_2$—N($CH_3$)—O-5'), amide-3 (3'-$CH_2$—C(=O)—N(H)-5'), amide-4 (3'-$CH_2$—N(H)—C(=O)-5'), formacetal (3'-O—$CH_2$—O-5'), and thioformacetal (3'-S—$CH_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

d. Certain Motifs

In certain embodiments, oligomeric compounds comprise or consist of oligonucleotides. In certain embodiments, such oligonucleotides comprise one or more chemical modification. In certain embodiments, chemically modified oligonucleotides comprise one or more modified sugars. In certain embodiments, chemically modified oligonucleotides comprise one or more modified nucleobases. In certain embodiments, chemically modified oligonucleotides comprise one or more modified internucleoside linkages. In certain embodiments, the chemical modifications (sugar modifications, nucleobase modifications, and/or linkage modifications) define a pattern or motif. In certain embodiments, the patterns of chemical modifications of sugar moieties, internucleoside linkages, and nucleobases are each independent of one another. Thus, an oligonucleotide may be described by its sugar modification motif, internucleoside linkage motif and/or nucleobase modification motif (as used herein, nucleobase modification motif describes the chemical modifications to the nucleobases independent of the sequence of nucleobases).

e. Certain Sugar Motifs

In certain embodiments, oligonucleotides comprise one or more type of modified sugar moieties and/or naturally occurring sugar moieties arranged along an oligonucleotide or region thereof in a defined pattern or sugar motif. Such sugar motifs include but are not limited to any of the sugar modifications discussed herein.

In certain embodiments, the oligonucleotides comprise or consist of a region having a gapmer sugar motif, which comprises two external regions or "wings" and a central or internal region or "gap." The three regions of a gapmer sugar motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap. In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric sugar gapmer). In certain embodiments, the sugar motifs of the 5'-wing differs from the sugar motif of the 3'-wing (asymmetric sugar gapmer).

i. Certain Nucleobase Modification Motifs

In certain embodiments, oligonucleotides comprise chemical modifications to nucleobases arranged along the oligonucleotide or region thereof in a defined pattern or nucleobases modification motif. In certain embodiments, each nucleobase is modified. In certain embodiments, none of the nucleobases is chemically modified.

In certain embodiments, oligonucleotides comprise a block of modified nucleobases. In certain such embodiments, the block is at the 3'-end of the oligonucleotide. In certain embodiments the block is within 3 nucleotides of the 3'-end of the oligonucleotide. In certain such embodiments, the block is at the 5'-end of the oligonucleotide. In certain embodiments the block is within 3 nucleotides of the 5'-end of the oligonucleotide.

In certain embodiments, nucleobase modifications are a function of the natural base at a particular position of an oligonucleotide. For example, in certain embodiments each purine or each pyrimidine in an oligonucleotide is modified. In certain embodiments, each adenine is modified. In certain embodiments, each guanine is modified. In certain embodiments, each thymine is modified. In certain embodiments, each cytosine is modified. In certain embodiments, each uracil is modified.

In certain embodiments, oligonucleotides comprise one or more nucleosides comprising a modified nucleobase. In certain embodiments, oligonucleotides having a gapmer sugar motif comprise a nucleoside comprising a modified nucleobase. In certain such embodiments, one nucleoside comprising a modified nucleobases is in the central gap of an oligonucleotide having a gapmer sugar motif. In certain embodiments, the sugar is an unmodified 2'deoxynucleoside. In certain embodiments, the modified nucleobase is selected from: a 2-thio pyrimidine and a 5-propyne pyrimidine In certain embodiments, some, all, or none of the cytosine moieties in an oligonucleotide are 5-methyl cytosine moieties. Herein, 5-methyl cytosine is not a "modified nucleobase." Accordingly, unless otherwise indicated, unmodified nucleobases include both cytosine residues having a 5-methyl and those lacking a 5 methyl. In certain embodiments, the methylation state of all or some cytosine nucleobases is specified.

ii. Certain Nucleoside Motifs

In certain embodiments, oligonucleotides comprise nucleosides comprising modified sugar moieties and/or nucleosides comprising modified nucleobases. Such motifs can be described by their sugar motif and their nucleobase motif separately or by their nucleoside motif, which provides positions or patterns of modified nucleosides (whether modified sugar, nucleobase, or both sugar and nucleobase) in an oligonucleotide.

In certain embodiments, the oligonucleotides comprise or consist of a region having a gapmer nucleoside motif, which comprises two external regions or "wings" and a central or internal region or "gap." The three regions of a gapmer nucleoside motif (the 5'-wing, the gap, and the 3'-wing) form a contiguous sequence of nucleosides wherein at least some of the sugar moieties and/or nucleobases of the nucleosides of each of the wings differ from at least some of the sugar moieties and/or nucleobase of the nucleosides of the gap. Specifically, at least the nucleosides of each wing that are closest to the gap (the 3'-most nucleoside of the 5'-wing and the 5'-most nucleoside of the 3'-wing) differ from the neighboring gap nucleosides, thus defining the boundary between the wings and the gap. In certain embodiments, the nucleosides within the gap are the same as one another. In certain embodiments, the gap includes one or more nucleoside that differs from one or more other nucleosides of the gap. In certain embodiments, the nucleoside motifs of the two wings are the same as one another (symmetric gapmer). In certain embodiments, the nucleoside motifs of the 5'-wing differs from the nucleoside motif of the 3'-wing (asymmetric gapmer).

1. Certain 5'-Wings

In certain embodiments, the 5'-wing of a gapmer consists of 1 to 5 linked nucleosides. In certain embodiments, the 5'-wing of a gapmer consists of 2 to 5 linked nucleosides. In certain embodiments, the 5'-wing of a gapmer consists of 3 to 5 linked nucleosides. In certain embodiments, the 5'-wing of a gapmer consists of 4 or 5 linked nucleosides. In certain embodiments, the 5'-wing of a gapmer consists of 1 to 4 linked nucleosides. In certain embodiments, the 5'-wing of a gapmer consists of 1 to 3 linked nucleosides. In certain embodiments, the 5'-wing of a gapmer consists of 1 or 2 linked nucleosides. In certain embodiments, the 5'-wing of a gapmer consists of 2 to 4 linked nucleosides. In certain embodiments, the 5'-wing of a gapmer consists of 2 or 3 linked nucleosides. In certain embodiments, the 5'-wing of a gapmer consists of 3 or 4 linked nucleosides. In certain embodiments, the 5'-wing of a gapmer consists of 1 nucleoside. In certain embodiments, the 5'-wing of a gapmer consists of 2 linked nucleosides. In certain embodiments, the 5'-wing of a gapmer consists of 3 linked nucleosides. In certain embodiments, the 5'-wing of a gapmer consists of 4 linked nucleosides. In certain embodiments, the 5'-wing of a gapmer consists of 5 linked nucleosides.

In certain embodiments, the 5'-wing of a gapmer comprises at least one bicyclic nucleoside. In certain embodiments, the 5'-wing of a gapmer comprises at least two bicyclic nucleosides. In certain embodiments, the 5'-wing of a gapmer comprises at least three bicyclic nucleosides. In certain embodiments, the 5'-wing of a gapmer comprises at least four bicyclic nucleosides. In certain embodiments, the 5'-wing of a gapmer comprises at least one constrained ethyl nucleoside. In certain embodiments, the 5'-wing of a gapmer comprises at least one LNA nucleoside. In certain embodiments, each nucleoside of the 5'-wing of a gapmer is a bicyclic nucleoside. In certain embodiments, each nucleoside of the 5'-wing of a gapmer is a constrained ethyl nucleoside. In certain embodiments, each nucleoside of the 5'-wing of a gapmer is a LNA nucleoside.

In certain embodiments, the 5'-wing of a gapmer comprises at least one non-bicyclic modified nucleoside. In certain embodiments, the 5'-wing of a gapmer comprises at least one 2'-substituted nucleoside. In certain embodiments, the 5'-wing of a gapmer comprises at least one 2'-MOE nucleoside. In certain embodiments, the 5'-wing of a gapmer comprises at least one 2'-OMe nucleoside. In certain embodiments, each nucleoside of the 5'-wing of a gapmer is a non-bicyclic modified nucleoside. In certain embodiments, each nucleoside of the 5'-wing of a gapmer is a 2'-substituted nucleoside. In certain embodiments, each nucleoside of the 5'-wing of a gapmer is a 2'-MOE nucleoside. In certain embodiments, each nucleoside of the 5'-wing of a gapmer is a 2'-OMe nucleoside.

In certain embodiments, the 5'-wing of a gapmer comprises at least one 2'-deoxynucleoside. In certain embodiments, each nucleoside of the 5'-wing of a gapmer is a 2'-deoxynucleoside. In a certain embodiments, the 5'-wing of a gapmer comprises at least one ribonucleoside. In certain embodiments, each nucleoside of the 5'-wing of a gapmer is a ribonucleoside. In certain embodiments, one, more than one, or each of the nucleosides of the 5'-wing is an RNA-like nucleoside.

In certain embodiments, the 5'-wing of a gapmer comprises at least one bicyclic nucleoside and at least one non-bicyclic modified nucleoside. In certain embodiments, the 5'-wing of a gapmer comprises at least one bicyclic nucleoside and at least one 2'-substituted nucleoside. In certain embodiments, the 5'-wing of a gapmer comprises at least one bicyclic nucleoside and at least one 2'-MOE nucleoside. In certain embodiments, the 5'-wing of a gapmer comprises at least one bicyclic nucleoside and at least one 2'-OMe nucleoside. In certain embodiments, the 5'-wing of a gapmer comprises at least one bicyclic nucleoside and at least one 2'-deoxynucleoside.

In certain embodiments, the 5'-wing of a gapmer comprises at least one constrained ethyl nucleoside and at least one non-bicyclic modified nucleoside. In certain embodiments, the 5'-wing of a gapmer comprises at least one constrained ethyl nucleoside and at least one 2'-substituted nucleoside. In certain embodiments, the 5'-wing of a gapmer comprises at least one constrained ethyl nucleoside and at least one 2'-MOE nucleoside. In certain embodiments, the 5'-wing of a gapmer comprises at least one constrained ethyl nucleoside and at least one 2'-OMe nucleoside. In certain embodiments, the 5'-wing of a gapmer comprises at least one constrained ethyl nucleoside and at least one 2'-deoxynucleoside.

In certain embodiments, the 5'-wing of a gapmer has a nucleoside motif selected from among the following: ADDA; ABDAA; ABBA; ABB; ABAA; AABAA; AAABAA; AAAABAA; AAAAABAA; AAABAA; AABAA; ABAB; ABADB; ABADDB; AAABB; AAAAA; ABBDC; ABDDC; ABBDCC; ABBDDC; ABBDCC; ABBC; AA; AAA; AAAA; AAAAB; AAAAAAA; AAAAAAAA; ABBB; AB; ABAB; AAAAB; AABBB; AAAAB; and AABBB, wherein each A is a modified nucleoside of a first type, each B is a modified nucleoside of a second type, each C is a modified nucleoside of a third type, and each D is an unmodified deoxynucleoside.

In certain embodiments, an oligonucleotide comprises any 5'-wing motif provided herein. In certain such embodiments, the oligonucleotide is a 5'-hemimer (does not comprise a 3'-wing). In certain embodiments, such an oligonucleotide is a gapmer. In certain such embodiments, the 3'-wing of the gapmer may comprise any nucleoside motif.

2. Certain 3'-Wings

In certain embodiments, the 3'-wing of a gapmer consists of 1 to 5 linked nucleosides. In certain embodiments, the 3'-wing of a gapmer consists of 2 to 5 linked nucleosides. In certain embodiments, the 3'-wing of a gapmer consists of 3 to 5 linked nucleosides. In certain embodiments, the 3'-wing of a gapmer consists of 4 or 5 linked nucleosides. In certain embodiments, the 3'-wing of a gapmer consists of 1 to 4 linked nucleosides. In certain embodiments, the 3'-wing of a gapmer consists of 1 to 3 linked nucleosides. In certain embodiments, the 3'-wing of a gapmer consists of 1 or 2 linked nucleosides. In certain embodiments, the 3'-wing of a gapmer consists of 2 to 4 linked nucleosides. In certain embodiments, the 3'-wing of a gapmer consists of 2 or 3 linked nucleosides. In certain embodiments, the 3'-wing of a gapmer consists of 3 or 4 linked nucleosides. In certain embodiments, the 3'-wing of a gapmer consists of 1 nucleoside. In certain embodiments, the 3'-wing of a gapmer consists of 2 linked nucleosides. In certain embodiments, the 3'-wing of a gapmer consists of 3 linked nucleosides. In certain embodiments, the 3'-wing of a gapmer consists of 4 linked nucleosides. In certain embodiments, the 3'-wing of a gapmer consists of 5 linked nucleosides.

In certain embodiments, the 3'-wing of a gapmer comprises at least one bicyclic nucleoside. In certain embodiments, the 3'-wing of a gapmer comprises at least one constrained ethyl nucleoside. In certain embodiments, the 3'-wing of a gapmer comprises at least one LNA nucleoside. In certain embodiments, each nucleoside of the 3'-wing of a gapmer is a bicyclic nucleoside. In certain embodiments, each nucleoside of the 3'-wing of a gapmer is a constrained ethyl nucleoside. In certain embodiments, each nucleoside of the 3'-wing of a gapmer is a LNA nucleoside.

In certain embodiments, the 3'-wing of a gapmer comprises at least one non-bicyclic modified nucleoside. In certain embodiments, the 3'-wing of a gapmer comprises at least two non-bicyclic modified nucleosides. In certain embodiments, the 3'-wing of a gapmer comprises at least three non-bicyclic modified nucleosides. In certain embodiments, the 3'-wing of a gapmer comprises at least four non-bicyclic modified nucleosides. In certain embodiments, the 3'-wing of a gapmer comprises at least one 2'-substituted nucleoside. In certain embodiments, the 3'-wing of a gapmer comprises at least one 2'-MOE nucleoside. In certain embodiments, the 3'-wing of a gapmer comprises at least one 2'-OMe nucleoside. In certain embodiments, each nucleoside of the 3'-wing of a gapmer is a non-bicyclic modified nucleoside. In certain embodiments, each nucleoside of the 3'-wing of a gapmer is a 2'-substituted nucleoside. In certain embodiments, each nucleoside of the 3'-wing of a gapmer is a 2'-MOE nucleoside. In certain embodiments, each nucleoside of the 3'-wing of a gapmer is a 2'-OMe nucleoside.

In certain embodiments, the 3'-wing of a gapmer comprises at least one 2'-deoxynucleoside. In certain embodiments, each nucleoside of the 3'-wing of a gapmer is a 2'-deoxynucleoside. In a certain embodiments, the 3'-wing of a gapmer comprises at least one ribonucleoside. In certain embodiments, each nucleoside of the 3'-wing of a gapmer is a ribonucleoside. In certain embodiments, one, more than one, or each of the nucleosides of the 5'-wing is an RNA-like nucleoside.

In certain embodiments, the 3'-wing of a gapmer comprises at least one bicyclic nucleoside and at least one non-bicyclic modified nucleoside. In certain embodiments, the 3'-wing of a gapmer comprises at least one bicyclic nucleoside and at least one 2'-substituted nucleoside. In certain embodiments, the 3'-wing of a gapmer comprises at least one bicyclic nucleoside and at least one 2'-MOE nucleoside. In certain embodiments, the 3'-wing of a gapmer comprises at least one bicyclic nucleoside and at least one 2'-OMe nucleoside. In certain embodiments, the 3'-wing of a gapmer comprises at least one bicyclic nucleoside and at least one 2'-deoxynucleoside.

In certain embodiments, the 3'-wing of a gapmer comprises at least one constrained ethyl nucleoside and at least one non-bicyclic modified nucleoside. In certain embodiments, the 3'-wing of a gapmer comprises at least one constrained ethyl nucleoside and at least one 2'-substituted nucleoside. In certain embodiments, the 3'-wing of a gapmer comprises at least one constrained ethyl nucleoside and at least one 2'-MOE nucleoside. In certain embodiments, the 3'-wing of a gapmer comprises at least one constrained ethyl nucleoside and at least one 2'-OMe nucleoside. In certain embodiments, the 3'-wing of a gapmer comprises at least one constrained ethyl nucleoside and at least one 2'-deoxynucleoside.

In certain embodiments, the 3'-wing of a gapmer comprises at least one LNA nucleoside and at least one non-bicyclic modified nucleoside. In certain embodiments, the 3'-wing of a gapmer comprises at least one LNA nucleoside and at least one 2'-substituted nucleoside. In certain embodiments, the 3'-wing of a gapmer comprises at least one LNA nucleoside and at least one 2'-MOE nucleoside. In certain embodiments, the 3'-wing of a gapmer comprises at least one LNA nucleoside and at least one 2'-OMe nucleoside. In certain embodiments, the 3'-wing of a gapmer comprises at least one LNA nucleoside and at least one 2'-deoxynucleoside.

In certain embodiments, the 3'-wing of a gapmer comprises at least one bicyclic nucleoside, at least one non-bicyclic modified nucleoside, and at least one 2'-deoxynucleoside. In certain embodiments, the 3'-wing of a gapmer comprises at least one constrained ethyl nucleoside, at least one non-bicyclic modified nucleoside, and at least one 2'-deoxynucleoside. In certain embodiments, the 3'-wing of a gapmer comprises at least one LNA nucleoside, at least one non-bicyclic modified nucleoside, and at least one 2'-deoxynucleoside.

In certain embodiments, the 3'-wing of a gapmer comprises at least one bicyclic nucleoside, at least one 2'-substituted nucleoside, and at least one 2'-deoxynucleoside. In certain embodiments, the 3'-wing of a gapmer comprises at least one constrained ethyl nucleoside, at least one 2'-substituted nucleoside, and at least one 2'-deoxynucleoside. In certain embodiments, the 3'-wing of a gapmer comprises at least one LNA nucleoside, at least one 2'-substituted nucleoside, and at least one 2'-deoxynucleoside.

In certain embodiments, the 3'-wing of a gapmer comprises at least one bicyclic nucleoside, at least one 2'-MOE nucleoside, and at least one 2'-deoxynucleoside. In certain embodiments, the 3'-wing of a gapmer comprises at least one constrained ethyl nucleoside, at least one 2'-MOE nucleoside, and at least one 2'-deoxynucleoside. In certain embodiments, the 3'-wing of a gapmer comprises at least one LNA nucleoside, at least one 2'-MOE nucleoside, and at least one 2'-deoxynucleoside.

In certain embodiments, the 3'-wing of a gapmer comprises at least one bicyclic nucleoside, at least one 2'-OMe nucleoside, and at least one 2'-deoxynucleoside. In certain embodiments, the 3'-wing of a gapmer comprises at least one constrained ethyl nucleoside, at least one 2'-OMe nucleoside, and at least one 2'-deoxynucleoside. In certain embodiments, the 3'-wing of a gapmer comprises at least one LNA nucleoside, at least one 2'-OMe nucleoside, and at least one 2'-deoxynucleoside.

In certain embodiments, the 3'-wing of a gapmer has a nucleoside motif selected from among the following: ABB; ABAA; AAABAA, AAAAABAA; AABAA; AAAABAA; AAAABAA; ABAB; AAAAA; AAABB; AAAAAAAA; AAAAAAA; AAAAAA; AAAAB; AAAA; AAA; AA; AB; ABBB; ABAB; AABBB; wherein each A is a modified nucleoside of a first type, each B is a modified nucleoside of a second type. In certain embodiments, an oligonucleotide comprises any 3'-wing motif provided herein. In certain such embodiments, the oligonucleotide is a 3'-hemimer (does not comprise a 5'-wing). In certain embodiments, such an oligonucleotide is a gapmer. In certain such embodiments, the 5'-wing of the gapmer may comprise any nucleoside motif.

3. Certain Central Regions (Gaps)

In certain embodiments, the gap of a gapmer consists of 6 to 20 linked nucleosides. In certain embodiments, the gap of a gapmer consists of 6 to 15 linked nucleosides. In certain embodiments, the gap of a gapmer consists of 6 to 12 linked nucleosides. In certain embodiments, the gap of a gapmer consists of 6 to 10 linked nucleosides. In certain embodiments, the gap of a gapmer consists of 6 to 9 linked nucleosides. In certain embodiments, the gap of a gapmer consists of 6 to 8 linked nucleosides. In certain embodiments, the gap of a gapmer consists of 6 or 7 linked nucleosides. In certain embodiments, the gap of a gapmer consists of 7 to 10 linked nucleosides. In certain embodiments, the gap of a gapmer consists of 7 to 9 linked nucleosides. In certain embodiments, the gap of a gapmer consists of 7 or 8 linked nucleosides. In certain embodiments, the gap of a gapmer consists of 8 to 10 linked nucleosides. In certain embodiments, the gap of a gapmer consists of 8 or 9 linked nucleosides. In certain embodiments, the gap of a gapmer consists of 6 linked nucleosides. In certain embodiments, the gap of a gapmer consists of 7 linked nucleosides. In certain embodiments, the gap of a gapmer consists of 8 linked nucleosides. In certain embodiments, the gap of a gapmer consists of 9 linked nucleosides. In certain embodiments, the gap of a gapmer consists of 10 linked nucleosides. In certain embodiments, the gap of a gapmer consists of 11 linked nucleosides. In certain embodiments, the gap of a gapmer consists of 12 linked nucleosides.

In certain embodiments, each nucleoside of the gap of a gapmer is a 2'-deoxynucleoside. In certain embodiments, the gap comprises one or more modified nucleosides. In certain embodiments, each nucleoside of the gap of a gapmer is a 2'-deoxynucleoside or is a modified nucleoside that is "DNA-like." In such embodiments, "DNA-like" means that the nucleoside has similar characteristics to DNA, such that a duplex comprising the gapmer and an RNA molecule is capable of activating RNase H. For example, under certain conditions, 2'-(ara)-F have been shown to support RNase H activation, and thus is DNA-like. In certain embodiments, one or more nucleosides of the gap of a gapmer is not a 2'-deoxynucleoside and is not DNA-like. In certain such embodiments, the gapmer nonetheless supports RNase H activation (e.g., by virtue of the number or placement of the non-DNA nucleosides).

In certain embodiments, gaps comprise a stretch of unmodified 2'-deoxynucleoside interrupted by one or more modified nucleosides, thus resulting in three sub-regions (two stretches of one or more 2'-deoxynucleosides and a stretch of one or more interrupting modified nucleosides). In certain embodiments, no stretch of unmodified 2'-deoxynucleosides is longer than 5, 6, or 7 nucleosides. In certain embodiments, such short stretches is achieved by using short gap regions. In certain embodiments, short stretches are achieved by interrupting a longer gap region.

4. Certain Gapmer Motifs

In certain embodiments, a gapmer comprises a 5'-wing, a gap, and a 3' wing, wherein the 5'-wing, gap, and 3' wing are independently selected from among those discussed above. For example, in certain embodiments, a gapmer has a 5'-wing, a gap, and a 3'-wing having features selected from among those listed in the following non-limiting table:

TABLE 4

Certain Gapmer Nucleoside Motifs

| 5'-wing region | Central gap region | 3'-wing region |
|---|---|---|
| ADDA | DDDDDD | ABB |
| ABBA | DDDADDDD | ABAA |
| AAAAAAA | DDDDDDDDDD | AAA |
| AAAAABB | DDDDDDDD | BBAAAAA |
| ABB | DDDDADDDD | ABB |
| ABB | DDDDBDDDD | BBA |
| ABB | DDDDDDDDD | BBA |
| AABAA | DDDDDDDDD | AABAA |
| ABB | DDDDDD | AABAA |
| AAABAA | DDDDDDDDD | AAABAA |
| AAABAA | DDDDDDDDD | AAB |
| ABAB | DDDDDDDDD | ABAB |
| AAABB | DDDDDD | BBA |
| ABADB | DDDDDDD | BBA |
| ABA | DBDDDDDDD | BBA |
| ABA | DADDDDDDD | BBA |
| ABAB | DDDDDDD | BBA |
| AA | DDDDDDDD | BBBBBBBB |
| ABB | DDDDDD | ABADB |
| AAAAB | DDDDDDD | BAAAA |
| ABBB | DDDDDDDDD | AB |
| AB | DDDDDDDDD | BBBA |
| ABBB | DDDDDDDDD | BBBA |
| AB | DDDDDDDD | ABA |
| ABB | DDDDWDDDD | BBA |
| AAABB | DDDWDDD | BBAAA |
| ABB | DDDDWWDDD | BBA |
| ABADB | DDDDDDD | BBA |
| ABBDC | DDDDDDD | BBA |
| ABBDDC | DDDDDD | BBA |
| ABBDCC | DDDDDD | BBA |
| ABB | DWWDWWDWW | BBA |
| ABB | DWDDDDDDD | BBA |
| ABB | DDWDDDDDD | BBA |
| ABB | DWWDDDDDD | BBA |
| AAABB | DDWDDDDDD | AA |
| BB | DDWDWDDDD | BBABBBB |
| ABB | DDDD($^N$D)DDDD | BBA |
| AAABB | DDD($^N$D)DDD | BBAAA |
| ABB | DDDD($^N$D)($^N$D)DDD | BBA |
| ABB | D($^N$D)($^N$D)D($^N$D)($^N$D)D($^N$D)($^N$D) | BBA |
| ABB | D($^N$D)DDDDDDD | BBA |
| ABB | DD($^N$D)DDDDDD | BBA |
| ABB | D($^N$D)($^N$D)DDDDDD | BBA |
| AAABB | DD($^N$D)DDDDDD | AA |
| BB | DD($^N$D)D($^N$D)DDDD | BBABBBB | wherein each A is a modified nucleoside of a first type, each B is a modified nucleoside of a second type and each W is a modified nucleoside of either the first type, the second type or a third type, each D is a nucleoside comprising an unmodified 2'deoxy sugar moiety and unmodified nucleobase, and $^N$D is modified nucleoside comprising a modified nucleobase and an unmodified 2'deoxy sugar moiety.

In certain embodiments, each A comprises a modified sugar moiety. In certain embodiments, each A comprises a 2'-substituted sugar moiety. In certain embodiments, each A comprises a 2'-substituted sugar moiety selected from among F, ara-F, OCH$_3$ and O(CH$_2$)$_2$—OCH$_3$. In certain embodiments, each A comprises a bicyclic sugar moiety. In certain embodiments, each A comprises a bicyclic sugar moiety selected from among cEt, cMOE, LNA, α-L-LNA, ENA and 2'-thio LNA. In certain embodiments, each A comprises a modified nucleobase. In certain embodiments, each A comprises a modified nucleobase selected from among 2-thio-thymidine nucleoside and 5-propyne uridine nucleoside.

In certain embodiments, each B comprises a modified sugar moiety. In certain embodiments, each B comprises a 2'-substituted sugar moiety. In certain embodiments, each B comprises a 2'-substituted sugar moiety selected from among F, (ara)-F, OCH$_3$ and O(CH$_2$)$_2$—OCH$_3$. In certain embodiments, each B comprises a bicyclic sugar moiety. In certain embodiments, each B comprises a bicyclic sugar moiety selected from among cEt, cMOE, LNA, α-L-LNA, ENA and 2'-thio LNA. In certain embodiments, each B comprises a modified nucleobase. In certain embodiments, each B comprises a modified nucleobase selected from among 2-thio-thymidine nucleoside and 5-propyne uridine nucleoside.

In certain embodiments, each C comprises a modified sugar moiety. In certain embodiments, each C comprises a 2'-substituted sugar moiety. In certain embodiments, each C comprises a 2'-substituted sugar moiety selected from among F, (ara)-F, OCH$_3$ and O(CH$_2$)$_2$—OCH$_3$. In certain embodiments, each C comprises a 5'-substituted sugar moiety. In certain embodiments, each C comprises a 5'-substituted sugar moiety selected from among 5'-Me, and 5'-(R)-Me. In certain embodiments, each C comprises a bicyclic sugar moiety. In certain embodiments, each C comprises a bicyclic sugar moiety selected from among cEt, cMOE, LNA, α-L-LNA, ENA and 2'-thio LNA. In certain embodiments, each C comprises a modified nucleobase. In certain embodiments, each C comprises a modified nucleobase selected from among 2-thio-thymidine and 5-propyne uridine.

In certain embodiments, each W comprises a modified sugar moiety. In certain embodiments, each W comprises a 2'-substituted sugar moiety. In certain embodiments, each W comprises a 2'-substituted sugar moiety selected from among F, (ara)-F, OCH$_3$ and O(CH$_2$)$_2$—OCH$_3$. In certain embodiments, each W comprises a 5'-substituted sugar moiety. In certain embodiments, each W comprises a 5'-substituted sugar moiety selected from among 5'-Me, and 5'-(R)-Me. In certain embodiments, each W comprises a bicyclic sugar moiety. In certain embodiments, each W comprises a bicyclic sugar moiety selected from among cEt, cMOE, LNA, α-L-LNA, ENA and 2'-thio LNA. In certain embodiments, each W comprises a sugar surrogate. In certain embodiments, each W comprises a sugar surrogate selected from among HNA and F-HNA.

In certain embodiments, at least one of A or B comprises a bicyclic sugar moiety, and the other comprises a 2'-substituted sugar moiety. In certain embodiments, one of A or B is an LNA nucleoside and the other of A or B comprises a 2'-substituted sugar moiety. In certain embodiments, one of A or B is a cEt nucleoside and the other of A or B comprises a 2'-substituted sugar moiety. In certain embodiments, one of A or B is an α-L-LNA nucleoside and the other of A or B comprises a 2'-substituted sugar moiety. In certain embodiments, one of A or B is an LNA nucleoside and the other of A or B comprises a 2'-MOE sugar moiety. In certain embodiments, one of A or B is a cEt nucleoside and the other of A or B comprises a 2'-MOE sugar moiety. In certain embodiments, one of A or B is an α-L-LNA nucleoside and the other of A or B comprises a 2'-MOE sugar moiety. In certain embodiments, one of A or B is an LNA nucleoside and the other of A or B comprises a 2'-F sugar moiety. In certain embodiments, one of A or B is a cEt nucleoside and the other of A or B comprises a 2'-F sugar moiety. In certain embodiments, one of A or B is an α-L-LNA nucleoside and the other of A or B comprises a 2'-F sugar moiety. In certain embodiments, one of A or B is an LNA nucleoside and the other of A or B comprises a 2'-(ara)-F sugar moiety. In certain embodiments, one of A or B is a cEt nucleoside and the other of A or B comprises a 2'-(ara)-F sugar moiety. In certain embodiments, one of A or B is an α-L-LNA nucleoside and the other of A or B comprises a 2'-(ara)-F sugar moiety.

In certain embodiments, A comprises a bicyclic sugar moiety, and B comprises a 2'-substituted sugar moiety. In certain embodiments, A is an LNA nucleoside and B comprises a 2'-substituted sugar moiety. In certain embodiments, A is a cEt nucleoside and B comprises a 2'-substituted sugar moiety. In certain embodiments, A is an α-L-LNA nucleoside and B comprises a 2'-substituted sugar moiety.

In certain embodiments, A comprises a bicyclic sugar moiety, and B comprises a 2'-MOE sugar moiety. In certain embodiments, A is an LNA nucleoside and B comprises a 2'-MOE sugar moiety. In certain embodiments, A is a cEt nucleoside and B comprises a 2'-MOE sugar moiety. In certain embodiments, A is an α-L-LNA nucleoside and B comprises a 2'-MOE sugar moiety.

In certain embodiments, A comprises a bicyclic sugar moiety, and B comprises a 2'-F sugar moiety. In certain embodiments, A is an LNA nucleoside and B comprises a 2'-F sugar moiety. In certain embodiments, A is a cEt nucleoside and B comprises a 2'-F sugar moiety. In certain embodiments, A is an α-L-LNA nucleoside and B comprises a 2'-F sugar moiety.

In certain embodiments, A comprises a bicyclic sugar moiety, and B comprises a 2'-(ara)-F sugar moiety. In certain embodiments, A is an LNA nucleoside and B comprises a 2'-(ara)-F sugar moiety. In certain embodiments, A is a cEt nucleoside and B comprises a 2'-(ara)-F sugar moiety. In certain embodiments, A is an α-L-LNA nucleoside and B comprises a 2'-(ara)-F sugar moiety.

In certain embodiments, B comprises a bicyclic sugar moiety, and A comprises a 2'-MOE sugar moiety. In certain embodiments, B is an LNA nucleoside and A comprises a 2'-MOE sugar moiety. In certain embodiments, B is a cEt nucleoside and A comprises a 2'-MOE sugar moiety. In certain embodiments, B is an α-L-LNA nucleoside and A comprises a 2'-MOE sugar moiety.

In certain embodiments, B comprises a bicyclic sugar moiety, and A comprises a 2'-F sugar moiety. In certain embodiments, B is an LNA nucleoside and A comprises a 2'-F sugar moiety. In certain embodiments, B is a cEt nucleoside and A comprises a 2'-F sugar moiety. In certain embodiments, B is an α-L-LNA nucleoside and A comprises a 2'-F sugar moiety.

In certain embodiments, B comprises a bicyclic sugar moiety, and A comprises a 2'-(ara)-F sugar moiety. In certain embodiments, B is an LNA nucleoside and A comprises a 2'-(ara)-F sugar moiety. In certain embodiments, B is a cEt nucleoside and A comprises a 2'-(ara)-F sugar moiety. In certain embodiments, B is an α-L-LNA nucleoside and A comprises a 2'-(ara)-F sugar moiety.

In certain embodiments, at least one of A or B comprises a bicyclic sugar moiety, another of A or B comprises a 2'-substituted sugar moiety and W comprises a modified nucleobase. In certain embodiments, one of A or B is an LNA nucleoside, another of A or B comprises a 2'-substituted sugar moiety, and W comprises a modified nucleobase. In certain embodiments, one of A or B is a cEt nucleoside, another of A or B comprises a 2'-substituted sugar moiety, and C comprises a modified nucleobase. In certain embodiments, one of A or B is an α-L-LNA nucleoside, another of A or B comprises a 2'-substituted sugar moiety, and W comprises a modified nucleobase.

In certain embodiments, one of A or B comprises a bicyclic sugar moiety, another of A or B comprises a 2'-MOE sugar moiety, and W comprises a modified nucleobase. In certain embodiments, one of A or B is an LNA nucleoside, another of A or B comprises a 2'-MOE sugar moiety, and W comprises a modified nucleobase. In certain embodiments, one of A or B is a cEt nucleoside, another of A or B comprises a 2'-MOE sugar moiety, and W comprises a modified nucleobase. In certain embodiments, one of A or B is an α-L-LNA nucleoside, another of A or B comprises a 2'-MOE sugar moiety, and W comprises a modified nucleobase.

In certain embodiments, one of A or B comprises a bicyclic sugar moiety, another of A or B comprises a 2'-F sugar moiety, and W comprises a modified nucleobase. In certain embodiments, one of A or B is an LNA nucleoside, another of A or B comprises a 2'-F sugar moiety, and W comprises a modified nucleobase. In certain embodiments, one of A or B is a cEt nucleoside, another of A or B comprises a 2'-F sugar moiety, and W comprises a modified nucleobase. In certain embodiments, one of A or B is an α-L-LNA nucleoside, another of A or B comprises a 2'-F sugar moiety, and W comprises a modified nucleobase.

In certain embodiments, one of A or B comprises a bicyclic sugar moiety, another of A or B comprises a 2'-(ara)-F sugar moiety, and W comprises a modified nucleobase. In certain embodiments, one of A or B is an LNA nucleoside, another of A or B comprises a 2'-(ara)-F sugar moiety, and W comprises a modified nucleobase. In certain embodiments, one of A or B is a cEt nucleoside, another of A or B comprises a 2'-(ara)-F sugar moiety, and W comprises a modified nucleobase. In certain embodiments, one of A or B is an α-L-LNA nucleoside, another of A or B comprises a 2'-(ara)-F sugar moiety, and W comprises a modified nucleobase.

In certain embodiments, one of A or B comprises a bicyclic sugar moiety, another of A or B comprises a 2'-substituted sugar moiety, and W comprises a 2-thio-thymidine nucleobase. In certain embodiments, one of A or B is an LNA nucleoside, another of A or B comprises a 2'-substituted sugar moiety, and W comprises a 2-thio-thymidine nucleobase. In certain embodiments, one of A or B is a cEt nucleoside, another of A or B comprises a 2'-substituted sugar moiety, and W comprises a 2-thio-thymidine nucleobase. In certain embodiments, one of A or B is an α-L-LNA nucleoside, another of A or B comprises a 2'-substituted sugar moiety, and W comprises a 2-thio-thymidine nucleobase.

In certain embodiments, one of A or B comprises a bicyclic sugar moiety, another of A or B comprises a 2'-MOE sugar moiety, and W comprises a 2-thio-thymidine nucleobase. In certain embodiments, one of A or B is an LNA nucleoside, another of A or B comprises a 2'-MOE sugar moiety, and W comprises a 2-thio-thymidine nucleobase. In certain embodiments, one of A or B is a cEt nucleoside, another of A or B comprises a 2'-MOE sugar moiety, and W comprises a 2-thio-thymidine nucleobase. In certain embodiments, one of A or B is an α-L-LNA nucleoside, another of A or B comprises a 2'-MOE sugar moiety, and W comprises a 2-thio-thymidine nucleobase.

In certain embodiments, one of A or B comprises a bicyclic sugar moiety, another of A or B comprises a 2'-F sugar moiety, and W comprises a 2-thio-thymidine nucleobase. In certain embodiments, one of A or B is an LNA nucleoside, another of A or B comprises a 2'-F sugar moiety, and W comprises a 2-thio-thymidine nucleobase. In certain embodiments, one of A or B is a cEt nucleoside, another of A or B comprises a 2'-F sugar moiety, and W comprises a 2-thio-thymidine nucleobase. In certain embodiments, one of A or B is an α-L-LNA nucleoside, another of A or B comprises a 2'-F sugar moiety, and W comprises a 2-thio-thymidine nucleobase.

In certain embodiments, one of A or B comprises a bicyclic sugar moiety, another of A or B comprises a 2'-(ara)-F sugar moiety, and W comprises a 2-thio-thymidine nucleobase. In certain embodiments, one of A or B is an LNA nucleoside, another of A or B comprises a 2'-(ara)-F sugar moiety, and W comprises a 2-thio-thymidine nucleobase. In certain embodiments, one of A or B is a cEt nucleoside, another of A or B comprises a 2'-(ara)-F sugar moiety, and W comprises a 2-thio-thymidine nucleobase. In certain embodiments, one of A or B is an α-L-LNA nucleoside, another of A or B comprises a 2'-(ara)-F sugar moiety, and W comprises 2-thio-thymidine nucleobase.

In certain embodiments, one of A or B comprises a bicyclic sugar moiety, another of A or B comprises a 2'-MOE sugar moiety, and W comprises a 5-propyne uridine nucleobase. In certain embodiments, one of A or B is an LNA nucleoside, another of A or B comprises a 2'-MOE sugar moiety, and C comprises a 5-propyne uridine nucleobase. In certain embodiments, one of A or B is a cEt nucleoside, another of A or B comprises a 2'-MOE sugar moiety, and W comprises a 5-propyne uridine nucleobase. In certain embodiments, one of A or B is an α-L-LNA nucleoside, another of A or B comprises a 2'-MOE sugar moiety, and C comprises a 5-propyne uridine nucleobase.

In certain embodiments, one of A or B comprises a bicyclic sugar moiety, another of A or B comprises a 2'-F sugar moiety, and W comprises a 5-propyne uridine nucleobase. In certain embodiments, one of A or B is an LNA nucleoside, another of A or B comprises a 2'-F sugar moiety, and C comprises a 5-propyne uridine nucleobase. In certain embodiments, one of A or B is a cEt nucleoside, another of A or B comprises a 2'-F sugar moiety, and W comprises a 5-propyne uridine nucleobase. In certain embodiments, one of A or B is an α-L-LNA nucleoside, another of A or B comprises a 2'-F sugar moiety, and W comprises a 5-propyne uridine nucleobase.

In certain embodiments, one of A or B comprises a bicyclic sugar moiety, another of A or B comprises a 2'-(ara)-F sugar moiety, and W comprises a 5-propyne uridine nucleobase. In certain embodiments, one of A or B is an LNA nucleoside, another of A or B comprises a 2'-(ara)-F sugar moiety, and W comprises a 5-propyne uridine nucleobase. In certain embodiments, one of A or B is a cEt nucleoside, another of A or B comprises a 2'-(ara)-F sugar moiety, and W comprises a 5-propyne uridine nucleobase. In certain embodiments, one of A or B is an α-L-LNA nucleoside, another of A or B comprises a 2'-(ara)-F sugar moiety, and W comprises a 5-propyne uridine nucleobase.

In certain embodiments, one of A or B comprises a bicyclic sugar moiety, another of A or B comprises a 2'-MOE sugar moiety, and W comprises a sugar surrogate. In certain embodiments, one of A or B is an LNA nucleoside, another of A or B comprises a 2'-MOE sugar moiety, and W comprises a sugar surrogate. In certain embodiments, one of A or B is a cEt nucleoside, another of A or B comprises a 2'-MOE sugar moiety, and W comprises a sugar surrogate. In certain embodiments, one of A or B is an α-L-LNA nucleoside, another of A or B comprises a 2'-MOE sugar moiety, and W comprises a sugar surrogate.

In certain embodiments, one of A or B comprises a bicyclic sugar moiety, another of A or B comprises a 2'-F sugar moiety, and W comprises a sugar surrogate. In certain embodiments, one of A or B is an LNA nucleoside, another of A or B comprises a 2'-F sugar moiety, and W comprises a sugar surrogate. In certain embodiments, one of A or B is a cEt nucleoside, another of A or B comprises a 2'-F sugar moiety, and W comprises a sugar surrogate. In certain embodiments, one of A or B is an α-L-LNA nucleoside, another of A or B comprises a 2'-F sugar moiety, and W comprises a sugar surrogate.

In certain embodiments, one of A or B comprises a bicyclic sugar moiety, another of A or B comprises a 2'-(ara)-F sugar moiety, and W comprises a sugar surrogate. In certain embodiments, one of A or B is an LNA nucleoside, another of A or B comprises a 2'-(ara)-F sugar moiety, and W comprises a sugar surrogate. In certain embodiments, one of A or B is a cEt nucleoside, another of A or B comprises a 2'-(ara)-F sugar moiety, and W comprises a sugar surrogate. In certain embodiments, one of A or B is an α-L-LNA nucleoside, another of A or B comprises a 2'-(ara)-F sugar moiety, and W comprises sugar surrogate.

In certain embodiments, one of A or B comprises a bicyclic sugar moiety, another of A or B comprises a 2'-MOE sugar moiety, and W comprises a HNA sugar surrogate. In certain embodiments, one of A or B is an LNA nucleoside, another of A or B comprises a 2'-MOE sugar moiety, and W comprises a HNA sugar surrogate. In certain embodiments, one of A or B is a cEt nucleoside, another of A or B comprises a 2'-MOE sugar moiety, and W comprises a HNA sugar surrogate. In certain embodiments, one of A or B is an α-L-LNA nucleoside, another of A or B comprises a 2'-MOE sugar moiety, and W comprises a HNA sugar surrogate.

In certain embodiments, one of A or B comprises a bicyclic sugar moiety, another of A or B comprises a 2'-F sugar moiety, and W comprises a HNA sugar surrogate. In certain embodiments, one of A or B is an LNA nucleoside, another of A or B comprises a 2'-F sugar moiety, and W comprises a HNA sugar surrogate. In certain embodiments, one of A or B is a cEt nucleoside, another of A or B comprises a 2'-F sugar moiety, and W comprises a HNA sugar surrogate. In certain embodiments, one of A or B is an α-L-LNA nucleoside, another of A or B comprises a 2'-F sugar moiety, and W comprises a sugar HNA surrogate.

In certain embodiments, one of A or B comprises a bicyclic sugar moiety, another of A or B comprises a 2'-(ara)-F sugar moiety, and W comprises a HNA sugar surrogate. In certain embodiments, one of A or B is an LNA nucleoside, another of A or B comprises a 2'-(ara)-F sugar moiety, and W comprises a HNA sugar surrogate. In certain embodiments, one of A or B is a cEt nucleoside, another of A or B comprises a 2'-(ara)-F sugar moiety, and W comprises a HNA sugar surrogate. In certain embodiments, one of A or B is an α-L-LNA nucleoside, another of A or B comprises a 2'-(ara)-F sugar moiety, and W comprises a HNA sugar surrogate.

In certain embodiments, one of A or B comprises a bicyclic sugar moiety, another of A or B comprises a 2'-MOE sugar moiety, and W comprises a F-HNA sugar surrogate. In certain embodiments, one of A or B is an LNA nucleoside, another of A or B comprises a 2'-MOE sugar moiety, and W comprises a F-HNA sugar surrogate. In certain embodiments, one of A or B is a cEt nucleoside, another of A or B comprises a 2'-MOE sugar moiety, and W comprises a F-HNA sugar surrogate. In certain embodiments, one of A or B is an α-L-LNA nucleoside, another of A or B comprises a 2'-MOE sugar moiety, and W comprises a F-HNA sugar surrogate.

In certain embodiments, one of A or B comprises a bicyclic sugar moiety, another of A or B comprises a 2'-F sugar moiety, and W comprises a F-HNA sugar surrogate. In certain embodiments, one of A or B is an LNA nucleoside, another of A or B comprises a 2'-F sugar moiety, and W comprises a F-HNA sugar surrogate. In certain embodiments, one of A or B is a cEt nucleoside, another of A or B comprises a 2'-F sugar moiety, and W comprises a F-HNA sugar surrogate. In certain embodiments, one of A or B is an α-L-LNA nucleoside, another of A or B comprises a 2'-F sugar moiety, and W comprises a F-HNA sugar surrogate.

In certain embodiments, one of A or B comprises a bicyclic sugar moiety, another of A or B comprises a 2'-(ara)-F sugar moiety, and W comprises a F-HNA sugar surrogate. In certain embodiments, one of A or B is an LNA nucleoside, another of A or B comprises a 2'-(ara)-F sugar moiety, and W comprises a F-HNA sugar surrogate. In certain embodiments, one of A or B is a cEt nucleoside, another of A or B comprises a 2'-(ara)-F sugar moiety, and W comprises a F-HNA sugar surrogate. In certain embodiments, one of A or B is an α-L-LNA nucleoside, another of A or B comprises a 2'-(ara)-F sugar moiety, and W comprises a F-HNA sugar surrogate.

In certain embodiments, one of A or B comprises a bicyclic sugar moiety, another of A or B comprises a 2'-MOE sugar moiety, and W comprises a 5'-Me DNA sugar moiety. In certain embodiments, one of A or B is an LNA nucleoside, another of A or B comprises a 2'-MOE sugar moiety, and W comprises a 5'-Me DNA sugar moiety. In certain embodiments, one of A or B is a cEt nucleoside, another of A or B comprises a 2'-MOE sugar moiety, and W comprises a 5'-Me DNA sugar moiety. In certain embodiments, one of A or B is an α-L-LNA nucleoside, another of A or B comprises a 2'-MOE sugar moiety, and W comprises a 5'-Me DNA sugar moiety.

In certain embodiments, one of A or B comprises a bicyclic sugar moiety, another of A or B comprises a 2'-F sugar moiety, and W comprises a 5'-Me DNA sugar moiety. In certain embodiments, one of A or B is an LNA nucleoside, another of A or B comprises a 2'-F sugar moiety, and W comprises a 5'-Me DNA sugar moiety. In certain embodiments, one of A or B is a cEt nucleoside, another of A or B comprises a 2'-F sugar moiety, and W comprises a 5'-Me DNA sugar moiety. In certain embodiments, one of A or B is an α-L-LNA nucleoside, another of A or B comprises a 2'-F sugar moiety, and W comprises a 5'-Me DNA sugar moiety.

In certain embodiments, one of A or B comprises a bicyclic sugar moiety, another of A or B comprises a 2'-(ara)-F sugar moiety, and W comprises a 5'-Me DNA sugar moiety. In certain embodiments, one of A or B is an LNA nucleoside, another of A or B comprises a 2'-(ara)-F sugar moiety, and W comprises a 5'-Me DNA sugar moiety. In certain embodiments, one of A or B is a cEt nucleoside, another of A or B comprises a 2'-(ara)-F sugar moiety, and W comprises a 5'-Me DNA sugar moiety. In certain embodiments, one of A or B is an α-L-LNA nucleoside, another of A or B comprises a 2'-(ara)-F sugar moiety, and W comprises a 5'-Me DNA sugar moiety.

In certain embodiments, one of A or B comprises a bicyclic sugar moiety, another of A or B comprises a 2'-MOE sugar moiety, and W comprises a 5'-(R)-Me DNA sugar moiety. In certain embodiments, one of A or B is an LNA nucleoside, another of A or B comprises a 2'-MOE sugar moiety, and W comprises a 5'-(R)-Me DNA sugar moiety. In certain embodiments, one of A or B is a cEt nucleoside, another of A or B comprises a 2'-MOE sugar moiety, and W comprises a 5'-(R)-Me DNA sugar moiety. In certain embodiments, one of A or B is an α-L-LNA nucleoside, another of A or B comprises a 2'-MOE sugar moiety, and W comprises a 5'-(R)-Me DNA sugar moiety.

In certain embodiments, one of A or B comprises a bicyclic sugar moiety, another of A or B comprises a 2'-F sugar moiety, and W comprises a 5'-(R)-Me DNA sugar moiety. In certain embodiments, one of A or B is an LNA nucleoside, another of A or B comprises a 2'-F sugar moiety, and W comprises a 5'-(R)-Me DNA sugar moiety. In certain embodiments, one of A or B is a cEt nucleoside, another of A or B comprises a 2'-F sugar moiety, and W comprises a 5'-(R)-Me DNA sugar moiety. In certain embodiments, one of A or B is an α-L-LNA nucleoside, another of A or B comprises a 2'-F sugar moiety, and W comprises a 5'-(R)-Me DNA sugar moiety.

In certain embodiments, one of A or B comprises a bicyclic sugar moiety, another of A or B comprises a 2'-(ara)-F sugar moiety, and W comprises a 5'-(R)-Me DNA sugar moiety. In certain embodiments, one of A or B is an LNA nucleoside, another of A or B comprises a 2'-(ara)-F sugar moiety, and W comprises a 5'-(R)-Me DNA sugar moiety. In certain embodiments, one of A or B is a cEt nucleoside, another of A or B comprises a 2'-(ara)-F sugar moiety, and W comprises a 5'-(R)-Me DNA sugar moiety. In certain embodiments, one of A or B is an α-L-LNA nucleoside, another of A or B comprises a 2'-(ara)-F sugar moiety, and W comprises a 5'-(R)-Me DNA sugar moiety.

In certain embodiments, at least two of A, B or W comprises a 2'-substituted sugar moiety, and the other comprises a bicyclic sugar moiety. In certain embodiments, at least two of A, B or W comprises a bicyclic sugar moiety, and the other comprises a 2'-substituted sugar moiety. In certain embodiments, a gapmer has a sugar motif other than: E-K-K-(D)$_9$-K-K-E; E-E-E-E-K-(D)$_9$-E-E-E-E-E; E-K-K-K-(D)$_9$-K-K-K-E; K-E-E-E-K-(D)$_9$-K-E-E-E-K; K-D-D-K-(D)$_9$-K-D-D-K; K-E-K-E-K-(D)$_9$-K-E-K-E-K; K-D-K-D-K-(D)$_9$-K-D-K-D-K; E-K-E-K-(D)$_9$-K-E-K-E; E-E-E-E-E-K-(D)$_8$-E-E-E-E-E; or E-K-E-K-E-(D)$_9$-E-K-E-K-E, wherein K is a nucleoside comprising a cEt sugar moiety and E is a nucleoside comprising a 2'-MOE sugar moiety.

iii. Certain Internucleoside Linkage Motifs

In certain embodiments, oligonucleotides comprise modified internucleoside linkages arranged along the oligonucleotide or region thereof in a defined pattern or modified internucleoside linkage motif. In certain embodiments, internucleoside linkages are arranged in a gapped motif, as described above for nucleoside motif. In such embodiments, the internucleoside linkages in each of two wing regions are different from the internucleoside linkages in the gap region. In certain embodiments the internucleoside linkages in the wings are phosphodiester and the internucleoside linkages in the gap are phosphorothioate. The nucleoside motif is independently selected, so such oligonucleotides having a gapped internucleoside linkage motif may or may not have a gapped nucleoside motif and if it does have a gapped nucleoside motif, the wing and gap lengths may or may not be the same.

In certain embodiments, oligonucleotides comprise a region having an alternating internucleoside linkage motif. In certain embodiments, oligonucleotides of the present invention comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

In certain embodiments, oligonucleotides comprise one or more methylphosphonate linkages. In certain embodiments, oligonucleotides having a gapmer nucleoside motif comprise a linkage motif comprising all phosphorothioate linkages except for one or two methylphosphonate linkages. In certain embodiments, one methylphosphonate linkage is in the central gap of an oligonucleotide having a gapmer nucleoside motif.

iv. Certain Modification Motifs

Modification motifs define oligonucleotides by nucleoside motif (sugar motif and nucleobase motif) and linkage motif. For example, certain oligonucleotides have the following modification motif:

$A_sA_sA_sD_sD_sD_sD_s(^ND)_sD_sD_sD_sD_sB_sB_sB$;

wherein each A is a modified nucleoside comprising a 2'-substituted sugar moiety; each D is an unmodified 2'-deoxynucleoside; each B is a modified nucleoside comprising a bicyclic sugar moiety; $^ND$ is a modified nucleoside comprising a modified nucleobase; and s is a phosphorothioate internucleoside linkage. Thus, the sugar motif is a gapmer motif. The nucleobase modification motif is a single modified nucleobase at $8^{th}$ nucleoside from the 5'-end. Combining the sugar motif and the nucleobase modification motif, the nucleoside motif is an interrupted gapmer where the gap of the sugar modified gapmer is interrupted by a nucleoside comprising a modified nucleobase. The linkage motif is uniform phosphorothioate. The following non-limiting Table further illustrates certain modification motifs:

TABLE 5

| Certain Modification Motifs | | |
| --- | --- | --- |
| 5'-wing region | Central gap region | 3'-wing region |
| B$_s$B$_s$ | $_sD_sD_sD_sD_sD_sD_sD_sD_s$ | A$_s$A$_s$A$_s$A$_s$A$_s$A$_s$A$_s$A |
| AsBsBs | DsDsDsDsDsDsDsDs | BsBsA |

TABLE 5-continued

Certain Modification Motifs

| 5'-wing region | Central gap region | 3'-wing region |
|---|---|---|
| AsBsBs | DsDsDsDs($^N$D)sDsDsDsDs | BsBsA |
| AsBsBs | DsDsDsDsAsDsDsDsDs | BsBsA |
| AsBsBs | DsDsDsDsBsDsDsDsDs | BsBsA |
| AsBsBs | DsDsDsDsWsDsDsDsDs | BsBsA |
| AsBsBsBs | DsDsDsDsDsDsDsDs | BsBsAsBsB |
| AsBsBs | DsDsDsDsDsDsDsDs | BsBsAsBsB |
| BsBsAsBsBs | DsDsDsDsDsDsDsDs | BsBsA |
| AsBsBs | DsDsDsDsDsDsDsDs | BsBsAsBsBsBsB |
| AsAsBsAsAs | DsDsDsDsDsDsDsDs | BsBsA |
| AsAsAsBsAsAs | DsDsDsDsDsDsDsDs | BsBsA |
| AsAsBsAsAs | DsDsDsDsDsDsDsDs | AsAsBsAsA |
| AsAsAsBsAsAs | DsDsDsDsDsDsDsDs | AsAsBsAsAsA |
| AsAsAsAsBsAsAs | DsDsDsDsDsDsDsDs | BsBsA |
| AsBsAsBs | DsDsDsDsDsDsDsDs | BsAsBsA |
| AsBsAsBs | DsDsDsDsDsDsDsDs | AsAsBsAsAs |
| AsBsBs | DsDsDsDsDsDsDsDs | BsAsBsA |
| BsBsAsBsBsB | DsDsDsDsDsDsDsDs | BsAsBsA |
| AsAsAsAs | DsDsDsDsDsDsDsDs | AsAsAsAsA |
| AsAsAsAs | DsDsDsDsDsDs | AsAsAsAsA |
| AsAsAsAs | DsDsDsDsDsDsDsDs | BsBsAsBsBsBsB |
| AsAsAsBsBs | DsDsDsDsDsDs | BsBsA |
| AsBsAsBs | DsDsDsDsDsDsDs | BsBsA |
| AsBsAsBs | DsDsDsDsDsDs | AsAsAsBsBs |
| AsAsAsAsBs | DsDsDsDsDsDs | BsAsAsAsA |
| BsBs | DsDsDsDsDsDs | AsA |
| AsAs | DsDsDsDsDsDs | AsAsAsAsAsAsA |
| AsAsAs | DsDsDsDsDsDs | AsAsAsAsAsA |
| AsAsAs | DsDsDsDsDsDs | AsAsAsAsAsA |
| AsBs | DsDsDsDsDsDs | BsBsBsA |
| AsBsBsBs | DsDsDsDsDsDsDsDs | BsA |
| AsBs | DsDsDsDsDsDsDsDs | BsBsBsA |
| AsAsAsBsBs | DsDsDs($^N$D)sDsDsDs | BsBsAsAsA |
| AsAsAsBsBs | DsDsAsDsDsDsDs | BsBsAsAsA |
| AsAsAsBsBs | DsDsBsDsDsDsDs | BsBsAsAsA |
| AsAsAsAsBs | DsDsDsDsDsDsDs | BsAsAsAsA |
| AsBsBsBs | DsDsDsDsDsDsDs | BsBsBsAsA |
| AsAsAsBs | DsDsDsDsDsDs | AsAsAsAsAs |
| AsBsBsBs | DsDsDsDsDsDs | AsAsAsAsAs |
| AsBsBsBs | DsDsDsDsDsDs | AsAsAsAsAs |
| AsAsAsAs | DsDsDsDsDsDs | BsAsAsAsA |
| AsAsAsAs | DsDsDsDsDsDs | BsBsAsAsAs |
| AsAsAsAs | DsDsDsDsDsDs | BsBsBsAsAs |
| AsBsBs | DsDsDsDs($^N$D)s($^N$D)sDsDsDs | BsBsA |
| AsBsBs | Ds($^N$D)s($^N$D)sDs($^N$D)s($^N$D)sDs($^N$D)s($^N$D)s | BsBsA |
| AsBsBs | Ds($^N$D)sDsDsDsDsDsDs | BsBsA |
| AsBsBs | Ds($^N$D)sDsDsDsDs | BsBsA |
| AsBsBs | Ds($^N$D)s($^N$D)sDsDsDsDsDs | BsBsA |
| AsBsBs | DsDs(D)zDsDsDsDsDs | BsBsA |
| AsBsBs | Ds(D)zDsDsDsDsDsDs | BsBsA |
| AsBsBs | (D)zDsDsDsDsDsDs | BsBsA |
| AsBsBs | DsDsAsDsDsDsDsDs | BsBsA |
| AsBsBs | DsDsBsDsDsDsDsDs | BsBsA |
| AsBsBs | AsDsDsDsDsDsDsDs | BsBsA |
| AsBsBs | BsDsDsDsDsDsDsDs | BsBsA |
| AsBsAsBs | DsDs(D)zDsDsDsDsDs | BsBsBsAsAs |
| AsAsAsBsBs | DsDs($^N$D)sDsDsDsDsDs | AsA |
| AsBsBsBs | Ds(D)zDsDsDsDsDsDs | AsAsAsBsBs |
| AsBsBs | DsDsDsDsDsDsDs(D)z | BsBsA |
| AsAsBsBsBs | DsDsDsAsDsDsDs | BsBsBsAsA |
| AsBsAsBsBs | DsDsDsBsDsDsDs | BsBsBsAsA |
| AsBsAsBs | DsDsDsAsDsDs | BsBsAsBsBsBsB |
| AsBsBsBs | DsDsDs(D)zDsDsDs | BsA |
| AsAsBsBsBs | DsDsAsDsDsDs | BsBsA |
| AsBsBs | DsDsDs(D)zDsDsDs | BsBsBsA |
| BsBs | DsDs($^N$D)sDs($^N$D)sDsDsDsDs | BsBsAsBsBsBsB | wherein each A and B are nucleosides comprising differently modified sugar moieties, each D is a nucleoside comprising an unmodified 2'deoxy sugar moiety, each W is a modified nucleoside of either the first type, the second type or a third type, each $^N$D is a modified nucleoside comprising a modified nucleobase, s is a phosphorothioate internucleoside linkage, and z is a non-phosphorothioate internucleoside linkage.

In certain embodiments, each A comprises a modified sugar moiety. In certain embodiments, each A comprises a 2'-substituted sugar moiety. In certain embodiments, each A comprises a 2'-substituted sugar moiety selected from among F, (ara)-F, OCH$_3$ and O(CH$_2$)$_2$—OCH$_3$. In certain embodiments, each A comprises a bicyclic sugar moiety. In certain embodiments, each A comprises a bicyclic sugar moiety selected from among cEt, cMOE, LNA, α-L-LNA, ENA and 2'-thio LNA. In certain embodiments, each A comprises a modified nucleobase. In certain embodiments, each A comprises a modified nucleobase selected from among 2-thio-thymidine nucleoside and 5-propyne uridine nucleoside. In certain embodiments, each B comprises a modified sugar moiety. In certain embodiments, each B comprises a 2'-substituted sugar moiety. In certain embodiments, each B comprises a 2'-substituted sugar moiety selected from among F, (ara)-F, OCH$_3$ and O(CH$_2$)$_2$—OCH$_3$. In certain embodiments, each B comprises a bicyclic sugar moiety. In certain embodiments, each B comprises a bicyclic sugar moiety selected from among cEt, cMOE, LNA, α-L-LNA, ENA and 2'-thio LNA. In certain embodiments, each B comprises a modified nucleobase. In certain embodiments, each B comprises a modified nucleobase selected from among 2-thio-thymidine nucleoside and 5-propyne urindine nucleoside.

In certain embodiments, each W comprises a modified sugar moiety. In certain embodiments, each W comprises a 2'-substituted sugar moiety. In certain embodiments, each W comprises a 2'-substituted sugar moiety selected from among F, (ara)-F, OCH$_3$ and O(CH$_2$)$_2$—OCH$_3$. In certain embodiments, each W comprises a 5'-substituted sugar moiety. In certain embodiments, each W comprises a 5'-substituted sugar moiety selected from among 5'-Me, and 5'-(R)-Me. In certain embodiments, each W comprises a bicyclic sugar moiety. In certain embodiments, each W comprises a bicyclic sugar moiety selected from among cEt, cMOE, LNA, α-L-LNA, ENA and 2'-thio LNA. In certain embodiments, each W comprises a sugar surrogate. In certain embodiments, each W comprises a sugar surrogate selected from among HNA and F-HNA.

In certain embodiments, at least one of A or B comprises a bicyclic sugar moiety, and the other comprises a 2'-substituted sugar moiety. In certain embodiments, one of A or B is an LNA nucleoside and the other of A or B comprises a 2'-substituted sugar moiety. In certain embodiments, one of A or B is a cEt nucleoside and the other of A or B comprises a 2'-substituted sugar moiety. In certain embodiments, one of A or B is an α-L-LNA nucleoside and the other of A or B comprises a 2'-substituted sugar moiety. In certain embodiments, one of A or B is an LNA nucleoside and the other of A or B comprises a 2'-MOE sugar moiety. In certain embodiments, one of A or B is a cEt nucleoside and the other of A or B comprises a 2'-MOE sugar moiety. In certain embodiments, one of A or B is an α-L-LNA nucleoside and the other of A or B comprises a 2'-MOE sugar moiety. In certain embodiments, one of A or B is an LNA nucleoside and the other of A or B comprises a 2'-F sugar moiety. In certain embodiments, one of A or B is a cEt nucleoside and the other of A or B comprises a 2'-F sugar moiety. In certain embodiments, one of A or B is an α-L-LNA nucleoside and the other of A or B comprises a 2'-F sugar moiety. In certain embodiments, one of A or B is an LNA nucleoside and the other of A or B comprises a 2'-(ara)-F sugar moiety. In certain embodiments, one of A or B is a cEt nucleoside and the other of A or B comprises a 2'-(ara)-F sugar moiety. In certain embodiments, one of A or B is an α-L-LNA nucleoside and the other of A or B comprises a 2'-(ara)-F sugar moiety.

In certain embodiments, A comprises a bicyclic sugar moiety, and B comprises a 2'-substituted sugar moiety. In certain embodiments, A is an LNA nucleoside and B comprises a 2'-substituted sugar moiety. In certain embodiments, A is a cEt nucleoside and B comprises a 2'-substituted sugar moiety. In certain embodiments, A is an α-L-LNA nucleoside and B comprises a 2'-substituted sugar moiety.

In certain embodiments, A comprises a bicyclic sugar moiety, and B comprises a 2'-MOE sugar moiety. In certain embodiments, A is an LNA nucleoside and B comprises a 2'-MOE sugar moiety. In certain embodiments, A is a cEt nucleoside and B comprises a 2'-MOE sugar moiety. In certain embodiments, A is an α-L-LNA nucleoside and B comprises a 2'-MOE sugar moiety.

In certain embodiments, A comprises a bicyclic sugar moiety, and B comprises a 2'-F sugar moiety. In certain embodiments, A is an LNA nucleoside and B comprises a 2'-F sugar moiety. In certain embodiments, A is a cEt nucleoside and B comprises a 2'-F sugar moiety. In certain embodiments, A is an α-L-LNA nucleoside and B comprises a 2'-F sugar moiety.

In certain embodiments, A comprises a bicyclic sugar moiety, and B comprises a 2'-(ara)-F sugar moiety. In certain embodiments, A is an LNA nucleoside and B comprises a 2'-(ara)-F sugar moiety. In certain embodiments, A is a cEt nucleoside and B comprises a 2'-(ara)-F sugar moiety. In certain embodiments, A is an α-L-LNA nucleoside and B comprises a 2'-(ara)-F sugar moiety.

In certain embodiments, B comprises a bicyclic sugar moiety, and A comprises a 2'-MOE sugar moiety. In certain embodiments, B is an LNA nucleoside and A comprises a 2'-MOE sugar moiety. In certain embodiments, B is a cEt nucleoside and A comprises a 2'-MOE sugar moiety. In certain embodiments, B is an α-L-LNA nucleoside and A comprises a 2'-MOE sugar moiety.

In certain embodiments, B comprises a bicyclic sugar moiety, and A comprises a 2'-F sugar moiety. In certain embodiments, B is an LNA nucleoside and A comprises a 2'-F sugar moiety. In certain embodiments, B is a cEt nucleoside and A comprises a 2'-F sugar moiety. In certain embodiments, B is an α-L-LNA nucleoside and A comprises a 2'-F sugar moiety.

In certain embodiments, B comprises a bicyclic sugar moiety, and A comprises a 2'-(ara)-F sugar moiety. In certain embodiments, B is an LNA nucleoside and A comprises a 2'-(ara)-F sugar moiety. In certain embodiments, B is a cEt nucleoside and A comprises a 2'-(ara)-F sugar moiety. In certain embodiments, B is an α-L-LNA nucleoside and A comprises a 2'-(ara)-F sugar moiety.

In certain embodiments, at least one of A or B comprises a bicyclic sugar moiety, another of A or B comprises a 2'-substituted sugar moiety and W comprises a modified nucleobase. In certain embodiments, one of A or B is an LNA nucleoside, another of A or B comprises a 2'-substituted sugar moiety, and W comprises a modified nucleobase. In certain embodiments, one of A or B is a cEt nucleoside, another of A or B comprises a 2'-substituted sugar moiety, and C comprises a modified nucleobase. In certain embodiments, one of A or B is an α-L-LNA nucleoside, another of A or B comprises a 2'-substituted sugar moiety, and W comprises a modified nucleobase.

In certain embodiments, one of A or B comprises a bicyclic sugar moiety, another of A or B comprises a 2'-MOE sugar moiety, and W comprises a modified nucleobase. In certain embodiments, one of A or B is an LNA nucleoside, another of A or B comprises a 2'-MOE sugar moiety, and W comprises a modified nucleobase. In certain embodiments, one of A or B is a cEt nucleoside, another of A or B comprises a 2'-MOE sugar moiety, and W comprises a modified nucleobase. In certain embodiments, one of A or B is an α-L-LNA nucleoside, another of A or B comprises a 2'-MOE sugar moiety, and W comprises a modified nucleobase.

In certain embodiments, one of A or B comprises a bicyclic sugar moiety, another of A or B comprises a 2'-F sugar moiety, and W comprises a modified nucleobase. In certain embodiments, one of A or B is an LNA nucleoside, another of A or B comprises a 2'-F sugar moiety, and W comprises a modified nucleobase. In certain embodiments, one of A or B is a cEt nucleoside, another of A or B comprises a 2'-F sugar moiety, and W comprises a modified nucleobase. In certain embodiments, one of A or B is an α-L-LNA nucleoside, another of A or B comprises a 2'-F sugar moiety, and W comprises a modified nucleobase.

In certain embodiments, one of A or B comprises a bicyclic sugar moiety, another of A or B comprises a 2'-(ara)-F sugar moiety, and W comprises a modified nucleobase. In certain embodiments, one of A or B is an LNA nucleoside, another of A or B comprises a 2'-(ara)-F sugar moiety, and W comprises a modified nucleobase. In certain embodiments, one of A or B is a cEt nucleoside, another of A or B comprises a 2'-(ara)-F sugar moiety, and W comprises a modified nucleobase. In certain embodiments, one of A or B is an α-L-LNA nucleoside, another of A or B comprises a 2'-(ara)-F sugar moiety, and W comprises a modified nucleobase.

In certain embodiments, one of A or B comprises a bicyclic sugar moiety, another of A or B comprises a 2'-substituted sugar moiety, and W comprises a 2-thio-thymidine nucleobase. In certain embodiments, one of A or B is an LNA nucleoside, another of A or B comprises a 2'-substituted sugar moiety, and W comprises a 2-thio-thymidine nucleobase. In certain embodiments, one of A or B is a cEt nucleoside, another of A or B comprises a 2'-substituted sugar moiety, and W comprises a 2-thio-thymidine nucleobase. In certain embodiments, one of A or B is an α-L-LNA nucleoside, another of A or B comprises a 2'-substituted sugar moiety, and W comprises a 2-thio-thymidine nucleobase.

In certain embodiments, one of A or B comprises a bicyclic sugar moiety, another of A or B comprises a 2'-MOE sugar moiety, and W comprises a 2-thio-thymidine nucleobase. In certain embodiments, one of A or B is an LNA nucleoside, another of A or B comprises a 2'-MOE sugar moiety, and W comprises a 2-thio-thymidine nucleobase. In certain embodiments, one of A or B is a cEt nucleoside, another of A or B comprises a 2'-MOE sugar moiety, and W comprises a 2-thio-thymidine nucleobase. In certain embodiments, one of A or B is an α-L-LNA nucleoside, another of A or B comprises a 2'-MOE sugar moiety, and W comprises a 2-thio-thymidine nucleobase.

In certain embodiments, one of A or B comprises a bicyclic sugar moiety, another of A or B comprises a 2'-F sugar moiety, and W comprises a 2-thio-thymidine nucleobase. In certain embodiments, one of A or B is an LNA nucleoside, another of A or B comprises a 2'-F sugar moiety, and W comprises a 2-thio-thymidine nucleobase. In certain embodiments, one of A or B is a cEt nucleoside, another of A or B comprises a 2'-F sugar moiety, and W comprises a 2-thio-thymidine nucleobase. In certain embodiments, one of A or B is an α-L-LNA nucleoside, another of A or B comprises a 2'-F sugar moiety, and W comprises a 2-thio-thymidine nucleobase.

In certain embodiments, one of A or B comprises a bicyclic sugar moiety, another of A or B comprises a 2'-(ara)-F sugar moiety, and W comprises a 2-thio-thymidine nucleobase. In certain embodiments, one of A or B is an LNA nucleoside, another of A or B comprises a 2'-(ara)-F sugar moiety, and W comprises a 2-thio-thymidine nucleobase. In certain embodiments, one of A or B is a cEt nucleoside, another of A or B comprises a 2'-(ara)-F sugar moiety, and W comprises a 2-thio-thymidine nucleobase. In certain embodiments, one of A or B is an α-L-LNA nucleoside, another of A or B comprises a 2'-(ara)-F sugar moiety, and W comprises 2-thio-thymidine nucleobase.

In certain embodiments, one of A or B comprises a bicyclic sugar moiety, another of A or B comprises a 2'-MOE sugar moiety, and W comprises a 5-propyne uridine nucleobase. In certain embodiments, one of A or B is an LNA nucleoside, another of A or B comprises a 2'-MOE sugar moiety, and C comprises a 5-propyne uridine nucleobase. In certain embodiments, one of A or B is a cEt nucleoside, another of A or B comprises a 2'-MOE sugar moiety, and W comprises a 5-propyne uridine nucleobase. In certain embodiments, one of A or B is an α-L-LNA nucleoside, another of A or B comprises a 2'-MOE sugar moiety, and C comprises a 5-propyne uridine nucleobase.

In certain embodiments, one of A or B comprises a bicyclic sugar moiety, another of A or B comprises a 2'-F sugar moiety, and W comprises a 5-propyne uridine nucleobase. In certain embodiments, one of A or B is an LNA nucleoside, another of A or B comprises a 2'-F sugar moiety, and C comprises a 5-propyne uridine nucleobase. In certain embodiments, one of A or B is a cEt nucleoside, another of A or B comprises a 2'-F sugar moiety, and W comprises a 5-propyne uridine nucleobase. In certain embodiments, one of A or B is an α-L-LNA nucleoside, another of A or B comprises a 2'-F sugar moiety, and W comprises a 5-propyne uridine nucleobase.

In certain embodiments, one of A or B comprises a bicyclic sugar moiety, another of A or B comprises a 2'-(ara)-F sugar moiety, and W comprises a 5-propyne uridine nucleobase. In certain embodiments, one of A or B is an LNA nucleoside, another of A or B comprises a 2'-(ara)-F sugar moiety, and W comprises a 5-propyne uridine nucleobase. In certain embodiments, one of A or B is a cEt nucleoside, another of A or B comprises a 2'-(ara)-F sugar moiety, and W comprises a 5-propyne uridine nucleobase. In certain embodiments, one of A or B is an α-L-LNA nucleoside, another of A or B comprises a 2'-(ara)-F sugar moiety, and W comprises a 5-propyne uridine nucleobase.

In certain embodiments, one of A or B comprises a bicyclic sugar moiety, another of A or B comprises a 2'-MOE sugar moiety, and W comprises a sugar surrogate. In certain embodiments, one of A or B is an LNA nucleoside, another of A or B comprises a 2'-MOE sugar moiety, and W comprises a sugar surrogate. In certain embodiments, one of A or B is a cEt nucleoside, another of A or B comprises a 2'-MOE sugar moiety, and W comprises a sugar surrogate. In certain embodiments, one of A or B is an α-L-LNA nucleoside, another of A or B comprises a 2'-MOE sugar moiety, and W comprises a sugar surrogate.

In certain embodiments, one of A or B comprises a bicyclic sugar moiety, another of A or B comprises a 2'-F sugar moiety, and W comprises a sugar surrogate. In certain embodiments, one of A or B is an LNA nucleoside, another of A or B comprises a 2'-F sugar moiety, and W comprises a sugar surrogate. In certain embodiments, one of A or B is a cEt nucleoside, another of A or B comprises a 2'-F sugar moiety, and W comprises a sugar surrogate. In certain embodiments, one of A or B is an α-L-LNA nucleoside, another of A or B comprises a 2'-F sugar moiety, and W comprises a sugar surrogate.

In certain embodiments, one of A or B comprises a bicyclic sugar moiety, another of A or B comprises a 2'-(ara)-F sugar moiety, and W comprises a sugar surrogate. In certain embodiments, one of A or B is an LNA nucleoside, another of A or B comprises a 2'-(ara)-F sugar moiety, and W comprises a sugar surrogate. In certain embodiments, one of A or B is a cEt nucleoside, another of A or B comprises a 2'-(ara)-F sugar moiety, and W comprises a sugar surrogate. In certain embodiments, one of A or B is an α-L-LNA nucleoside, another of A or B comprises a 2'-(ara)-F sugar moiety, and W comprises sugar surrogate.

In certain embodiments, one of A or B comprises a bicyclic sugar moiety, another of A or B comprises a 2'-MOE sugar moiety, and W comprises a HNA sugar surrogate. In certain embodiments, one of A or B is an LNA nucleoside, another of A or B comprises a 2'-MOE sugar moiety, and W comprises a HNA sugar surrogate. In certain embodiments, one of A or B is a cEt nucleoside, another of A or B comprises a 2'-MOE sugar moiety, and W comprises a HNA sugar surrogate. In certain embodiments, one of A or B is an α-L-LNA nucleoside, another of A or B comprises a 2'-MOE sugar moiety, and W comprises a HNA sugar surrogate.

In certain embodiments, one of A or B comprises a bicyclic sugar moiety, another of A or B comprises a 2'-F sugar moiety, and W comprises a HNA sugar surrogate. In certain embodiments, one of A or B is an LNA nucleoside, another of A or B comprises a 2'-F sugar moiety, and W comprises a HNA sugar surrogate. In certain embodiments, one of A or B is a cEt nucleoside, another of A or B comprises a 2'-F sugar moiety, and W comprises a HNA sugar surrogate. In certain embodiments, one of A or B is an α-L-LNA nucleoside, another of A or B comprises a 2'-F sugar moiety, and W comprises a sugar HNA surrogate.

In certain embodiments, one of A or B comprises a bicyclic sugar moiety, another of A or B comprises a 2'-(ara)-F sugar moiety, and W comprises a HNA sugar surrogate. In certain embodiments, one of A or B is an LNA nucleoside, another of A or B comprises a 2'-(ara)-F sugar moiety, and W comprises a HNA sugar surrogate. In certain embodiments, one of A or B is a cEt nucleoside, another of A or B comprises a 2'-(ara)-F sugar moiety, and W comprises a HNA sugar surrogate. In certain embodiments, one of A or B is an α-L-LNA nucleoside, another of A or B comprises a 2'-(ara)-F sugar moiety, and W comprises a HNA sugar surrogate.

In certain embodiments, one of A or B comprises a bicyclic sugar moiety, another of A or B comprises a 2'-MOE sugar moiety, and W comprises a F-HNA sugar surrogate. In certain embodiments, one of A or B is an LNA nucleoside, another of A or B comprises a 2'-MOE sugar moiety, and W comprises a F-HNA sugar surrogate. In certain embodiments, one of A or B is a cEt nucleoside, another of A or B comprises a 2'-MOE sugar moiety, and W comprises a F-HNA sugar surrogate. In certain embodiments, one of A or B is an α-L-LNA nucleoside, another of A or B comprises a 2'-MOE sugar moiety, and W comprises a F-HNA sugar surrogate.

In certain embodiments, one of A or B comprises a bicyclic sugar moiety, another of A or B comprises a 2'-F sugar moiety, and W comprises a F-HNA sugar surrogate. In certain embodiments, one of A or B is an LNA nucleoside, another of A or B comprises a 2'-F sugar moiety, and W comprises a F-HNA sugar surrogate. In certain embodiments, one of A or B is a cEt nucleoside, another of A or B comprises a 2'-F sugar moiety, and W comprises a F-HNA sugar surrogate. In certain embodiments, one of A or B is an α-L-LNA nucleoside, another of A or B comprises a 2'-F sugar moiety, and W comprises a F-HNA sugar surrogate.

In certain embodiments, one of A or B comprises a bicyclic sugar moiety, another of A or B comprises a 2'-(ara)-F sugar moiety, and W comprises a F-HNA sugar surrogate. In certain embodiments, one of A or B is an LNA nucleoside, another of A or B comprises a 2'-(ara)-F sugar moiety, and W comprises a F-HNA sugar surrogate. In certain embodiments, one of A or B is a cEt nucleoside, another of A or B comprises a 2'-(ara)-F sugar moiety, and W comprises a F-HNA sugar surrogate. In certain embodiments, one of A or B is an α-L-LNA nucleoside, another of A or B comprises a 2'-(ara)-F sugar moiety, and W comprises a F-HNA sugar surrogate.

In certain embodiments, one of A or B comprises a bicyclic sugar moiety, another of A or B comprises a 2'-MOE sugar moiety, and W comprises a 5'-Me DNA sugar moiety. In certain embodiments, one of A or B is an LNA nucleoside, another of A or B comprises a 2'-MOE sugar moiety, and W comprises a 5'-Me DNA sugar moiety. In certain embodiments, one of A or B is a cEt nucleoside, another of A or B comprises a 2'-MOE sugar moiety, and W comprises a 5'-Me DNA sugar moiety. In certain embodiments, one of A or B is an α-L-LNA nucleoside, another of A or B comprises a 2'-MOE sugar moiety, and W comprises a 5'-Me DNA sugar moiety.

In certain embodiments, one of A or B comprises a bicyclic sugar moiety, another of A or B comprises a 2'-F sugar moiety, and W comprises a 5'-Me DNA sugar moiety. In certain embodiments, one of A or B is an LNA nucleoside, another of A or B comprises a 2'-F sugar moiety, and W comprises a 5'-Me DNA sugar moiety. In certain embodiments, one of A or B is a cEt nucleoside, another of A or B comprises a 2'-F sugar moiety, and W comprises a 5'-Me DNA sugar moiety. In certain embodiments, one of A or B is an α-L-LNA nucleoside, another of A or B comprises a 2'-F sugar moiety, and W comprises a 5'-Me DNA sugar moiety.

In certain embodiments, one of A or B comprises a bicyclic sugar moiety, another of A or B comprises a 2'-(ara)-F sugar moiety, and W comprises a 5'-Me DNA sugar moiety. In certain embodiments, one of A or B is an LNA nucleoside, another of A or B comprises a 2'-(ara)-F sugar moiety, and W comprises a 5'-Me DNA sugar moiety. In certain embodiments, one of A or B is a cEt nucleoside, another of A or B comprises a 2'-(ara)-F sugar moiety, and W comprises a 5'-Me DNA sugar moiety. In certain embodiments, one of A or B is an α-L-LNA nucleoside, another of A or B comprises a 2'-(ara)-F sugar moiety, and W comprises a 5'-Me DNA sugar moiety.

In certain embodiments, one of A or B comprises a bicyclic sugar moiety, another of A or B comprises a 2'-MOE sugar moiety, and W comprises a 5'-(R)-Me DNA sugar moiety. In certain embodiments, one of A or B is an LNA nucleoside, another of A or B comprises a 2'-MOE sugar moiety, and W comprises a 5'-(R)-Me DNA sugar moiety. In certain embodiments, one of A or B is a cEt nucleoside, another of A or B comprises a 2'-MOE sugar moiety, and W comprises a 5'-(R)-Me DNA sugar moiety. In certain embodiments, one of A or B is an α-L-LNA nucleoside, another of A or B comprises a 2'-MOE sugar moiety, and W comprises a 5'-(R)-Me DNA sugar moiety.

In certain embodiments, one of A or B comprises a bicyclic sugar moiety, another of A or B comprises a 2'-F sugar moiety, and W comprises a 5'-(R)-Me DNA sugar moiety. In certain embodiments, one of A or B is an LNA nucleoside, another of A or B comprises a 2'-F sugar moiety, and W comprises a 5'-(R)-Me DNA sugar moiety. In certain embodiments, one of A or B is a cEt nucleoside, another of A or B comprises a 2'-F sugar moiety, and W comprises a 5'-(R)-Me DNA sugar moiety. In certain embodiments, one of A or B is an α-L-LNA nucleoside, another of A or B comprises a 2'-F sugar moiety, and W comprises a 5'-(R)-Me DNA sugar moiety.

In certain embodiments, one of A or B comprises a bicyclic sugar moiety, another of A or B comprises a 2'-(ara)-F sugar moiety, and W comprises a 5'-(R)-Me DNA sugar moiety. In certain embodiments, one of A or B is an LNA nucleoside, another of A or B comprises a 2'-(ara)-F sugar moiety, and W comprises a 5'-(R)-Me DNA sugar moiety. In certain embodiments, one of A or B is a cEt nucleoside, another of A or B comprises a 2'-(ara)-F sugar moiety, and W comprises a 5'-(R)-Me DNA sugar moiety. In certain embodiments, one of A or B is an α-L-LNA nucleoside, another of A or B comprises a 2'-(ara)-F sugar moiety, and W comprises a 5'-(R)-Me DNA sugar moiety.

In certain embodiments, at least two of A, B or W comprises a 2'-substituted sugar moiety, and the other comprises a bicyclic sugar moiety. In certain embodiments, at least two of A, B or W comprises a bicyclic sugar moiety, and the other comprises a 2'-substituted sugar moiety.

f. Certain Overall Lengths

In certain embodiments, the present invention provides oligomeric compounds including oligonucleotides of any of a variety of ranges of lengths. In certain embodiments, the invention provides oligomeric compounds or oligonucleotides consisting of X to Y linked nucleosides, where X represents the fewest number of nucleosides in the range and Y represents the largest number of nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, the invention provides oligomeric compounds which comprise oligonucleotides consisting of 8 to 9, 8 to 10, 8 to 11, 8 to 12, 8 to 13, 8 to 14, 8 to 15, 8 to 16, 8 to 17, 8 to 18, 8 to 19, 8 to 20, 8 to 21, 8 to 22, 8 to 23, 8 to 24, 8 to 25, 8 to 26, 8 to 27, 8 to 28, 8 to 29, 8 to 30, 9 to 10, 9 to 11, 9 to 12, 9 to 13, 9 to 14, 9 to 15, 9 to 16, 9 to 17, 9 to 18, 9 to 19, 9 to 20, 9 to 21, 9 to 22, 9 to 23, 9 to 24, 9 to 25, 9 to 26, 9 to 27, 9 to 28, 9 to 29, 9 to 30, 10 to 11, 10 to 12, 10 to 13, 10 to 14, 10 to 15, 10 to 16, 10 to 17, 10 to 18, 10 to 19, 10 to 20, 10 to 21, 10 to 22, 10 to 23, 10 to 24, 10 to 25, 10 to 26, 10 to 27, 10 to 28, 10 to 29, 10 to 30, 11 to 12, 11 to 13, 11 to 14, 11 to 15, 11 to 16, 11 to 17, 11 to 18, 11 to 19, 11 to 20, 11 to 21, 11 to 22, 11 to 23, 11 to 24, 11 to 25, 11 to 26, 11 to 27, 11 to 28, 11 to 29, 11 to 30, 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides. In embodiments where the number of nucleosides of an oligomeric compound or oligonucleotide is limited, whether to a range or to a specific number, the oligomeric compound or oligonucleotide may, nonetheless further comprise additional other substituents. For example, an oligonucleotide comprising 8-30 nucleosides excludes oligonucleotides having 31 nucleosides, but, unless otherwise indicated, such an oligonucleotide may further comprise, for example one or more conjugates, terminal groups, or other substituents. In certain embodiments, a gapmer oligonucleotide has any of the above lengths.

Further, where an oligonucleotide is described by an overall length range and by regions having specified lengths, and where the sum of specified lengths of the regions is less than the upper limit of the overall length range, the oligonucleotide may have additional nucleosides, beyond those of the specified regions, provided that the total number of nucleosides does not exceed the upper limit of the overall length range.

g. Certain Oligonucleotides

In certain embodiments, oligonucleotides of the present invention are characterized by their modification motif and overall length. In certain embodiments, such parameters are each independent of one another. Thus, unless otherwise indicated, each internucleoside linkage of an oligonucleotide having a gapmer sugar motif may be modified or unmodified and may or may not follow the gapmer modification pattern of the sugar modifications. For example, the internucleoside linkages within the wing regions of a sugar-gapmer may be the same or different from one another and may be the same or different from the internucleoside linkages of the gap region. Likewise, such sugar-gapmer oligonucleotides may comprise one or more modified nucleobase independent of the gapmer pattern of the sugar modifications. One of skill in the art will appreciate that such motifs may be combined to create a variety of oligonucleotides. Herein if a description of an oligonucleotide or oligomeric compound is silent with respect to one or more parameter, such parameter is not limited. Thus, an oligomeric compound described only as having a gapmer sugar motif without further description may have any length, internucleoside linkage motif, and nucleobase modification motif. Unless otherwise indicated, all chemical modifications are independent of nucleobase sequence.

h. Certain Conjugate Groups

In certain embodiments, oligomeric compounds are modified by attachment of one or more conjugate groups. In general, conjugate groups modify one or more properties of the attached oligomeric compound including but not limited to pharmacodynamics, pharmacokinetics, stability, binding, absorption, cellular distribution, cellular uptake, charge and clearance. Conjugate groups are routinely used in the chemical arts and are linked directly or via an optional conjugate linking moiety or conjugate linking group to a parent compound such as an oligomeric compound, such as an oligonucleotide. Conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., do-decan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937).

In certain embodiments, a conjugate group comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

In certain embodiments, conjugate groups are directly attached to oligonucleotides in oligomeric compounds. In certain embodiments, conjugate groups are attached to oligonucleotides by a conjugate linking group. In certain such embodiments, conjugate linking groups, including, but not limited to, bifunctional linking moieties such as those known in the art are amenable to the compounds provided herein. Conjugate linking groups are useful for attachment of conjugate groups, such as chemical stabilizing groups, functional groups, reporter groups and other groups to selective sites in a parent compound such as for example an oligomeric compound. In general a bifunctional linking moiety comprises a hydrocarbyl moiety having two functional groups. One of the functional groups is selected to bind to a parent molecule or compound of interest and the other is selected to bind essentially any selected group such as chemical functional group or a conjugate group. In some embodiments, the conjugate linker comprises a chain structure or an oligomer of repeating units such as ethylene glycol or amino acid units. Examples of functional groups that are routinely used in a bifunctional linking moiety include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like.

Some nonlimiting examples of conjugate linking moieties include pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other linking groups include, but are not limited to, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

Conjugate groups may be attached to either or both ends of an oligonucleotide (terminal conjugate groups) and/or at any internal position.

In certain embodiments, conjugate groups are at the 3'-end of an oligonucleotide of an oligomeric compound. In certain embodiments, conjugate groups are near the 3'-end. In certain embodiments, conjugates are attached at the 3'end of an oligomeric compound, but before one or more terminal group nucleosides. In certain embodiments, conjugate groups are placed within a terminal group.

In certain embodiments, the present invention provides oligomeric compounds. In certain embodiments, oligomeric compounds comprise an oligonucleotide. In certain embodiments, an oligomeric compound comprises an oligonucleotide and one or more conjugate and/or terminal groups. Such conjugate and/or terminal groups may be added to oligonucleotides having any of the motifs discussed above. Thus, for example, an oligomeric compound comprising an oligonucleotide having region of alternating nucleosides may comprise a terminal group.

E. Antisense Compounds

In certain embodiments, oligomeric compounds provided herein are antisense compounds. Such antisense compounds are capable of hybridizing to a target nucleic acid, resulting in at least one antisense activity. In certain embodiments, antisense compounds specifically hybridize to one or more target nucleic acid. In certain embodiments, a specifically hybridizing antisense compound has a nucleobase sequence comprising a region having sufficient complementarity to a target nucleic acid to allow hybridization and result in antisense activity and insufficient complementarity to any non-target so as to avoid non-specific hybridization to any non-target nucleic acid sequences under conditions in which specific hybridization is desired (e.g., under physiological conditions for in vivo or therapeutic uses, and under conditions in which assays are performed in the case of in vitro assays).

In certain embodiments, the present invention provides antisense compounds comprising oligonucleotides that are fully complementary to the target nucleic acid over the entire length of the oligonucleotide. In certain embodiments, oligonucleotides are 99% complementary to the target nucleic acid. In certain embodiments, oligonucleotides are 95% complementary to the target nucleic acid. In certain embodiments, such oligonucleotides are 90% complementary to the target nucleic acid.

In certain embodiments, such oligonucleotides are 85% complementary to the target nucleic acid. In certain embodiments, such oligonucleotides are 80% complementary to the target nucleic acid. In certain embodiments, an antisense compound comprises a region that is fully complementary to a target nucleic acid and is at least 80% complementary to the target nucleic acid over the entire length of the oligonucleotide. In certain such embodiments, the region of full complementarity is from 6 to 14 nucleobases in length.

a. Certain Antisense Activities and Mechanisms

In certain antisense activities, hybridization of an antisense compound results in recruitment of a protein that cleaves of the target nucleic acid. For example, certain antisense compounds result in RNase H mediated cleavage of target nucleic acid. RNase H is a cellular endonuclease that cleaves the RNA strand of an RNA:DNA duplex. The "DNA" in such an RNA:DNA duplex, need not be unmodified DNA. In certain embodiments, the invention provides antisense compounds that are sufficiently "DNA-like" to elicit RNase H activity. Such DNA-like antisense compounds include, but are not limited to gapmers having unmodified deoxyfuronose sugar moieties in the nucleosides of the gap and modified sugar moieties in the nucleosides of the wings.

Antisense activities may be observed directly or indirectly. In certain embodiments, observation or detection of an antisense activity involves observation or detection of a change in an amount of a target nucleic acid or protein encoded by such target nucleic acid; a change in the ratio of splice variants of a nucleic acid or protein; and/or a phenotypic change in a cell or animal.

In certain embodiments, compounds comprising oligonucleotides having a gapmer nucleoside motif described herein have desirable properties compared to non-gapmer oligonucleotides or to gapmers having other motifs. In certain circumstances, it is desirable to identify motifs resulting in a favorable combination of potent antisense activity and relatively low toxicity. In certain embodiments, compounds of the present invention have a favorable therapeutic index (measure of potency divided by measure of toxicity).

F. Certain Pharmaceutical Compositions

In certain embodiments, the present invention provides pharmaceutical compositions comprising one or more antisense compound. In certain embodiments, such pharmaceutical composition comprises a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water. In certain embodiments, a pharmaceutical composition consists of one or more antisense compound and sterile water. In certain embodiments, the sterile saline is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile phosphate-buffered saline (PBS). In certain embodiments, the sterile saline is pharmaceutical grade PBS.

In certain embodiments, antisense compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

Pharmaceutical compositions comprising antisense compounds encompass any pharmaceutically acceptable salts, esters, or salts of such esters. In certain embodiments, pharmaceutical compositions comprising antisense compounds comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligomeric compound which are cleaved by endogenous nucleases within the body, to form the active antisense oligomeric compound.

Lipid moieties have been used in nucleic acid therapies in a variety of methods. In certain such methods, the nucleic acid is introduced into preformed liposomes or lipoplexes made of mixtures of cationic lipids and neutral lipids. In certain methods, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions provided herein comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition provided herein comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition provided herein comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition provided herein is prepared for oral administration. In certain embodiments, pharmaceutical compositions are prepared for buccal administration.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition provided herein comprises an oligonucleotide in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more modified oligonucleotide provided herein is formulated as a prodrug. In certain embodiments, upon in vivo administration, a prodrug is chemically converted to the biologically, pharmaceutically or therapeutically more active form of an oligonucleotide. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, the present invention provides compositions and methods for reducing the amount or activity of a target nucleic acid in a cell. In certain embodiments, the cell is in an animal. In certain embodiments, the animal is a mammal. In certain embodiments, the animal is a rodent. In certain embodiments, the animal is a primate. In certain embodiments, the animal is a non-human primate. In certain embodiments, the animal is a human.

In certain embodiments, the present invention provides methods of administering a pharmaceutical composition comprising an oligomeric compound of the present invention to an animal. Suitable administration routes include, but are not limited to, oral, rectal, transmucosal, intestinal, enteral, topical, suppository, through inhalation, intrathecal, intracerebroventricular, intraperitoneal, intranasal, intraocular, intratumoral, and parenteral (e.g., intravenous, intramuscular, intramedullary, and subcutaneous). In certain embodiments, pharmaceutical intrathecals are administered to achieve local rather than systemic exposures. For example, pharmaceutical compositions may be injected directly in the area of desired effect (e.g., into the liver).

Nonlimiting Disclosure and Incorporation by Reference

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified or naturally occurring bases, such as "AT$^{me}$CGAUCG," wherein $^{me}$C indicates a cytosine base comprising a methyl group at the 5-position.

EXAMPLES

The following examples illustrate certain embodiments of the present invention and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif. And, for example, where a particular high-affinity modification appears at a particular position, other high-affinity modifications at the same position are considered suitable, unless otherwise indicated.

Example 1

Synthesis of Oligomeric Compounds

The oligomeric compounds used in accordance with this disclosure may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as alkylated derivatives and those having phosphorothioate linkages.

Oligomeric compounds: Unsubstituted and substituted phosphodiester (P=O) oligomeric compounds, including without limitation, oligonucleotides can be synthesized on an automated DNA synthesizer (Applied Biosystems model 394) using standard phosphoramidite chemistry with oxidation by iodine.

In certain embodiments, phosphorothioate internucleoside linkages (P=S) are synthesized similar to phosphodiester internucleoside linkages with the following exceptions: thiation is effected by utilizing a 10% w/v solution of 3,H-1,2-benzodithiole-3-one 1,1-dioxide in acetonitrile for the oxidation of the phosphite linkages. The thiation reaction step time is increased to 180 sec and preceded by the normal capping step. After cleavage from the CPG column and deblocking in concentrated ammonium hydroxide at 55° C. (12-16 hr), the oligomeric compounds are recovered by precipitating with greater than 3 volumes of ethanol from a 1 M NH$_4$OAc solution. Phosphinate internucleoside linkages can be prepared as described in U.S. Pat. No. 5,508,270.

Alkyl phosphonate internucleoside linkages can be prepared as described in U.S. Pat. No. 4,469,863.

3'-Deoxy-3'-methylene phosphonate internucleoside linkages can be prepared as described in U.S. Pat. No. 5,610,289 or 5,625,050.

Phosphoramidite internucleoside linkages can be prepared as described in U.S. Pat. No. 5,256,775 or 5,366,878.

Alkylphosphonothioate internucleoside linkages can be prepared as described in published PCT applications PCT/US94/00902 and PCT/US93/06976 (published as WO 94/17093 and WO 94/02499, respectively).

3'-Deoxy-3'-amino phosphoramidate internucleoside linkages can be prepared as described in U.S. Pat. No. 5,476,925.

Phosphotriester internucleoside linkages can be prepared as described in U.S. Pat. No. 5,023,243.

Borano phosphate internucleoside linkages can be prepared as described in U.S. Pat. Nos. 5,130,302 and 5,177,198.

Oligomeric compounds having one or more non-phosphorus containing internucleoside linkages including without limitation methylenemethylimino linked oligonucleosides, also identified as MMI linked oligonucleosides, methylenedimethylhydrazo linked oligonucleosides, also identified as MDH linked oligonucleosides, methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone oligomeric compounds having, for instance, alternating MMI and P=O or P=S linkages can be prepared as described in U.S. Pat. Nos. 5,378,825, 5,386,023, 5,489,677, 5,602,240 and 5,610,289.

Formacetal and thioformacetal internucleoside linkages can be prepared as described in U.S. Pat. Nos. 5,264,562 and 5,264,564.

Ethylene oxide internucleoside linkages can be prepared as described in U.S. Pat. No. 5,223,618.

Example 2

Isolation and Purification of Oligomeric Compounds

After cleavage from the controlled pore glass solid support or other support medium and deblocking in concentrated ammonium hydroxide at 55° C. for 12-16 hours, the oligomeric compounds, including without limitation oligonucleotides and oligonucleosides, are recovered by precipitation out of 1 M NH$_4$OAc with >3 volumes of ethanol. Synthesized oligomeric compounds are analyzed by electrospray mass spectroscopy (molecular weight determination) and by capillary gel electrophoresis. The relative amounts of phosphorothioate and phosphodiester linkages obtained in the synthesis is determined by the ratio of correct molecular weight relative to the −16 amu product (+/−32+/−48). For some studies oligomeric compounds are purified by HPLC, as described by Chiang et al., J. Biol. Chem. 1991, 266, 18162-18171. Results obtained with HPLC-purified material are generally similar to those obtained with non-HPLC purified material.

Example 3

Synthesis of Oligomeric Compounds Using the 96 Well Plate Format

Oligomeric compounds, including without limitation oligonucleotides, can be synthesized via solid phase P(III) phosphoramidite chemistry on an automated synthesizer capable of assembling 96 sequences simultaneously in a 96-well format. Phosphodiester internucleoside linkages are afforded by oxidation with aqueous iodine. Phosphorothioate internucleoside linkages are generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites can be purchased from commercial vendors (e.g. PE-Applied Biosystems, Foster City, Calif., or Pharmacia, Piscataway, N.J.). Non-standard nucleosides are synthesized as per standard or patented methods and can be functionalized as base protected beta-cyanoethyldiisopropyl phosphoramidites.

Oligomeric compounds can be cleaved from support and deprotected with concentrated $NH_4OH$ at elevated temperature (55-60° C.) for 12-16 hours and the released product then dried in vacuo. The dried product is then re-suspended in sterile water to afford a master plate from which all analytical and test plate samples are then diluted utilizing robotic pipettors.

Example 4

Analysis of Oligomeric Compounds Using the 96-Well Plate Format

The concentration of oligomeric compounds in each well can be assessed by dilution of samples and UV absorption spectroscopy. The full-length integrity of the individual products can be evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition is confirmed by mass analysis of the oligomeric compounds utilizing electrospray-mass spectroscopy. All assay test plates are diluted from the master plate using single and multi-channel robotic pipettors. Plates are judged to be acceptable if at least 85% of the oligomeric compounds on the plate are at least 85% full length.

Example 5

In Vitro Treatment of Cells with Oligomeric Compounds

The effect of oligomeric compounds on target nucleic acid expression is tested in any of a variety of cell types provided that the target nucleic acid is present at measurable levels. This can be routinely determined using, for example, PCR or Northern blot analysis. Cell lines derived from multiple tissues and species can be obtained from American Type Culture Collection (ATCC, Manassas, Va.).

The following cell type is provided for illustrative purposes, but other cell types can be routinely used, provided that the target is expressed in the cell type chosen. This can be readily determined by methods routine in the art, for example Northern blot analysis, ribonuclease protection assays or RT-PCR.

b.END cells: The mouse brain endothelial cell line b.END was obtained from Dr. Werner Risau at the Max Plank Institute (Bad Nauheim, Germany). b.END cells are routinely cultured in DMEM, high glucose (Invitrogen Life Technologies, Carlsbad, Calif.) supplemented with 10% fetal bovine serum (Invitrogen Life Technologies, Carlsbad, Calif.). Cells are routinely passaged by trypsinization and dilution when they reached approximately 90% confluence. Cells are seeded into 96-well plates (Falcon-Primaria #353872, BD Biosciences, Bedford, Mass.) at a density of approximately 3000 cells/well for uses including but not limited to oligomeric compound transfection experiments.

Experiments Involving Treatment of Cells with Oligomeric Compounds:

When cells reach appropriate confluency, they are treated with oligomeric compounds using a transfection method as described.

LIPOFECTIN™

When cells reached 65-75% confluency, they are treated with one or more oligomeric compounds. The oligomeric compound is mixed with LIPOFECTIN™ Invitrogen Life Technologies, Carlsbad, Calif.) in Opti-MEM™-1 reduced serum medium (Invitrogen Life Technologies, Carlsbad, Calif.) to achieve the desired concentration of the oligomeric compound(s) and a LIPOFECTIN™ concentration of 2.5 or 3 µg/mL per 100 nM oligomeric compound(s). This transfection mixture is incubated at room temperature for approximately 0.5 hours. For cells grown in 96-well plates, wells are washed once with 100 µL OPTI-MEM™-1 and then treated with 130 µL of the transfection mixture. Cells grown in 24-well plates or other standard tissue culture plates are treated similarly, using appropriate volumes of medium and oligomeric compound(s). Cells are treated and data are obtained in duplicate or triplicate. After approximately 4-7 hours of treatment at 37° C., the medium containing the transfection mixture is replaced with fresh culture medium. Cells are harvested 16-24 hours after treatment with oligomeric compound(s).

Other suitable transfection reagents known in the art include, but are not limited to, CYTOFECTIN™, LIPOFECTAMINE™, OLIGOFECTAMINE™, and FUGENE™. Other suitable transfection methods known in the art include, but are not limited to, electroporation.

Example 6

Real-Time Quantitative PCR Analysis of Target mRNA Levels

Quantitation of target mRNA levels is accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and coefficient of determination of the GAPDH and target signals generated from the multiplexed samples fall within 10% of their corresponding values generated from the single-plexed samples, the primer-probe set specific for that target is deemed multiplexable. Other methods of PCR are also known in the art.

RT and PCR reagents are obtained from Invitrogen Life Technologies (Carlsbad, Calif.). RT, real-time PCR is carried out by adding 20 µL PCR cocktail (2.5×PCR buffer minus $MgCl_2$, 6.6 mM $MgCl_2$, 375 µM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96-well plates containing 30 µL total RNA solution (20-200 ng). The RT reaction is carried out by incubation for 30 minutes at 48° C. Following a 10 minute incubation at 95° C. to activate the PLATINUM® Taq, 40 cycles of a two-step PCR protocol are carried out: 95° C. for 15 seconds (denaturation) followed by 60° C. for 1.5 minutes (annealing/extension).

Gene target quantities obtained by RT, real-time PCR are normalized using either the expression level of GAPDH, a gene whose expression is constant, or by quantifying total RNA using RIBOGREEN™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent (Molecular Probes, Inc. Eugene, Oreg.). Methods of RNA quantification by RIBOGREEN™ are taught in Jones, L. J., et al, (Analytical Biochemistry, 1998, 265, 368-374).

In this assay, 170 µL of RIBOGREEN™ working reagent (RIBOGREEN™ reagent diluted 1:350 in 10 mM Tris-HCl, 1 mM EDTA, pH 7.5) is pipetted into a 96-well plate containing 30 µL purified, cellular RNA. The plate is read in a CytoFluor 4000 (PE Applied Biosystems) with excitation at 485 nm and emission at 530 nm.

Example 7

Analysis of Oligonucleotide Inhibition of Target Expression

Antisense modulation of a target expression can be assayed in a variety of ways known in the art. For example, a target mRNA levels can be quantitated by, e.g., Northern blot analysis, competitive polymerase chain reaction (PCR), or real-time PCR. Real-time quantitative PCR is presently desired. RNA analysis can be performed on total cellular RNA or poly(A)+ mRNA. One method of RNA analysis of the present disclosure is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of a target can be quantitated in a variety of ways well known in the art, such as immunoprecipitation, Western blot analysis (immunoblotting), enzyme-linked immunosorbant assay (ELISA) or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Methods for preparation of polyclonal antisera are taught in, for example, Ausubel, F. M. et al., *Current Protocols in Molecular Biology*, Volume 2, pp. 11.12.1-11.12.9, John Wiley & Sons, Inc., 1997. Preparation of monoclonal antibodies is taught in, for example, Ausubel, F. M. et al., *Current Protocols in Molecular Biology*, Volume 2, pp. 11.4.1-11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1-10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1-10.8.21, John Wiley & Sons, Inc., 1997. Enzyme-linked immunosorbant assays (ELISA) are standard in the art and can be found at, for example, Ausubel, F. M. et al., *Current Protocols in Molecular Biology*, Volume 2, pp. 11.2.1-11.2.22, John Wiley & Sons, Inc., 1991.

Example 8

Design of Phenotypic Assays and In Vivo Studies for the Use of Target Inhibitors Phenotypic Assays Once target inhibitors have been identified by the methods disclosed herein, the oligomeric compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of a target in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with a target inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Measurement of the expression of one or more of the genes of the cell after treatment is also used as an indicator of the efficacy or potency of the a target inhibitors. Hallmark genes, or those genes suspected to be associated with a specific disease state, condition, or phenotype, are measured in both treated and untreated cells.

Example 9

RNA Isolation

Poly(A)+ mRNA Isolation

Poly(A)+ mRNA is isolated according to Miura et al., (Clin. Chem., 1996, 42, 1758-1764). Other methods for poly(A)+ mRNA isolation are routine in the art. Briefly, for cells grown on 96-well plates, growth medium is removed from the cells and each well is washed with 200 μL cold PBS. 60 μL lysis buffer (10 mM Tris-HCl, pH 7.6, 1 mM EDTA, 0.5 M NaCl, 0.5% NP-40, 20 mM vanadyl-ribonucleoside complex) is added to each well, the plate is gently agitated and then incubated at room temperature for five minutes. 55 μL of lysate is transferred to Oligo d(T) coated 96-well plates (AGCT Inc., Irvine Calif.). Plates are incubated for 60 minutes at room temperature, washed 3 times with 200 μL of wash buffer (10 mM Tris-HCl pH 7.6, 1 mM EDTA, 0.3 M NaCl). After the final wash, the plate is blotted on paper towels to remove excess wash buffer and then air-dried for 5 minutes. 60 μL of elution buffer (5 mM Tris-HCl pH 7.6), preheated to 70° C., is added to each well, the plate is incubated on a 90° C. hot plate for 5 minutes, and the eluate is then transferred to a fresh 96-well plate.

Cells grown on 100 mm or other standard plates may be treated similarly, using appropriate volumes of all solutions.

Total RNA Isolation

Total RNA is isolated using an RNEASY 96™ kit and buffers purchased from Qiagen Inc. (Valencia, Calif.) following the manufacturer's recommended procedures. Briefly, for cells grown on 96-well plates, growth medium is removed from the cells and each well is washed with 200 μL cold PBS. 150 μL Buffer RLT is added to each well and the plate vigorously agitated for 20 seconds. 150 μL of 70% ethanol is then added to each well and the contents mixed by pipetting three times up and down. The samples are then transferred to the RNEASY 96™ well plate attached to a QIAVAC™ manifold fitted with a waste collection tray and attached to a vacuum source. Vacuum is applied for 1 minute. 500 μL of Buffer RW1 is added to each well of the RNEASY 96™ plate and incubated for 15 minutes and the vacuum is again applied for 1 minute. An additional 500 μL of Buffer RW1 is added to each well of the RNEASY 96™ plate and the vacuum is applied for 2 minutes. 1 mL of Buffer RPE is then added to each well of the RNEASY 96™ plate and the vacuum applied for a period of 90 seconds. The Buffer RPE wash is then repeated and the vacuum is applied for an additional 3 minutes. The plate is then removed from the QIAVAC™ manifold and blotted dry on paper towels. The plate is then re-attached to the QIAVAC™ manifold fitted with a collection tube rack containing 1.2 mL collection tubes. RNA is then eluted by pipetting 140 μL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 10

Target-Specific Primers and Probes

Probes and primers may be designed to hybridize to a target sequence, using published sequence information.

For example, for human PTEN, the following primer-probe set was designed using published sequence information (GENBANK™ accession number U92436.1, SEQ ID NO: 1).

```
                                           (SEQ ID NO: 2)
    Forward primer:    AATGGCTAAGTGAAGATGACAATCAT (SEQ ID NO: 3)
    Reverse primer:    TGCACATATCATTACACCAGTTCGT
```

And the PCR probe:

```
                                           (SEQ ID NO: 4)
      FAM-TTGCAGCAATTCACTGTAAAGCTGGAAAGG-TAMRA,
``` where FAM is the fluorescent dye and TAMRA is the quencher dye.

Example 11

Western Blot Analysis of Target Protein Levels

Western blot analysis (immunoblot analysis) is carried out using standard methods. Cells are harvested 16-20 h after oligonucleotide treatment, washed once with PBS, suspended in Laemmli buffer (100 l/well), boiled for 5 minutes and loaded on a 16% SDS-PAGE gel. Gels are run for 1.5 hours at 150 V, and transferred to membrane for western blotting. Appropriate primary antibody directed to a target is used, with a radiolabeled or fluorescently labeled secondary antibody directed against the primary antibody species. Bands are visualized using a PHOSPHORIMAGER™ (Molecular Dynamics, Sunnyvale Calif.).

Example 12

2-10-2 LNA Gapmers

The following gapmers comprising a 2-10-2 LNA motif were prepared using the procedures as described above. A subscript "1" indicates a nucleoside comprising a bicyclic sugar moiety comprising a 4'-$CH_2$—O-2'bridge.

TABLE 6

LNA Gapmers

| ISIS No. | Motif Sequence | Backbone | SEQ ID NO |
|---|---|---|---|
| 457847 | 2-10-2 $C_1C_1$TGGTGTACACC$_1C_1$Uniform | PS | 5 |
| 457848 | 2-10-2 $G_1G_1$TCCCTGCAGTA$_1C_1$Uniform | PS | 6 |

Example 13

FVII On-Target Knockdown

The inhibitory concentrations of ISIS No. 457847 and ISIS No. 457848 are presented in Table 6. The inhibitory concentrations were calculated by plotting the doses of ISIS No. 457847 and ISIS No. 457848 versus the percent inhibition of FVII mRNA expression achieved at each concentration, and noting the concentration of oligonucleotide at which 10%, 20%, 50%, 80%, and 90% inhibition of FVII mRNA expression was achieved compared to the control. This example demonstrates that both Isis No. 457847 and Isis No. 457848 are potent inhibitors of FVII, and that Isis No. 457848 is a more potent inhibitor of FVII than Isis No. 457847. In this example, FVII is the "target," all other genes are "off-target genes."

TABLE 7

| 24 hours | Dose (mg/kg) Isis No. 457847 | Dose (mg/kg) Isis No. 457848 |
|---|---|---|
| $IC_{10}$ | 39 | 21 |
| $IC_{20}$ | 30 | 15 |
| $IC_{50}$ | 19 | 9 |
| $IC_{80}$ | 12 | 5 |
| $IC_{90}$ | 9 | 4 |

Example 14

In Vivo Acute Toxicity Study: Identification of Sentinel Genes

Balb/c mice were subcutaneously administered saline, Isis No. 457847, or 457848 at different doses as shown in the table below. Four out of the eight mice in each group were sacrificed 24 hours after administration. Immediately after each mouse was sacrificed, the livers were frozen in liquid nitrogen and then sent to Expression Analysis (Durham, N.C.) for whole genome expression. Gene expression analysis on each of livers of the sacrificed mice was performed using a microarray to obtain whole genome profiling.

Results from the microarray indicated that treatment with both Isis No. 457847 and Isis No. 457848 induced more off-target down regulation than off-target up regulation.

For Isis No. 457848 at 100 mg/kg, it was found that 1617 off-target genes experienced a two-fold change in modulation of amount or activity, meaning that 1617 genes either decreased expression by at least two-fold, or increased expression by at least two-fold. For Isis No. 457847 at 200 mg/kg, it was found that 225 off-target genes experienced a two-fold change in modulation of amount or activity, meaning that 225 genes either decreased expression by at least two-fold, or increased expression by at least two-fold.

Comparison and analysis of the changes in the modulation of amount or activity of these off-target genes resulted in the identification of 143 off-target genes (e.g. sentinel genes) that experienced a two-fold change in modulation of amount or activity after administration of both 100 mg/kg of Isis No. 457848 and 200 mg/kg of Isis No. 457847. These 143 overlapping off-target genes are listed in Table 9.

TABLE 8

| Isis No. | Dose (mg/kg) | Number of Mice |
|---|---|---|
| Saline | 0 | 8 |
| 457847 | 200 | 8 |
| 457847 | 100 | 8 |
| 457847 | 50 | 8 |
| 457847 | 25 | 8 |
| 457847 | 12.5 | 8 |
| Saline | 0 | 8 |
| 457848 | 200 | 8 |
| 457848 | 100 | 8 |
| 457848 | 50 | 8 |
| 457848 | 25 | 8 |
| 457848 | 12.5 | 8 |

TABLE 9

Off-Target Gene Identification

| Symbol | Gene ID |
|---|---|
| Rexo4 | 227656 |
| 1810044A24Rik | 76510 |
| Atic | 108147 |
| Ccdc85b | 240514 |
| Capzb | 12345 |
| Abat | 268860 |
| Pdss2 | 71365 |
| Gcnt2 | 14538 |
| Cadps2 | 320405 |
| Vav2 | 22325 |
| Prei4 | 74182 |
| Prkag2 | 108099 |
| Dnajc12 | 30045 |
| Rab8a | 17274 |
| Lrit1 | 239037 |
| Pawr | 114774 |
| St3gal3 | 20441 |
| Pank1 | 75735 |
| Ssbp3 | 72475 |
| Cdo1 | 12583 |
| Dusp8 | 18218 |
| Kctd17 | 72844 |
| A530050D06Rik | 104816 |
| Fbxl17 | 50758 |
| Zfhx3 | 11906 |
| Ide | 15925 |
| 1810020D17Rik | 66273 |
| Msi2 | 76626 |
| Pard3 | 93742 |
| Ythdf3 | 229096 |
| Usp18 | 24110 |
| BC023892 | 212943 |
| 4933407C03Rik | 74440 |
| Itpr1 | 16438 |
| Dnaic1 | 68922 |
| Tssc1 | 380752 |
| BC048546 | 232400 |
| Ctnnbl1 | 66642 |
| Luc7l2 | 192196 |
| Snd1 | 56463 |
| Ero1lb | 67475 |
| Tyk2 | 54721 |
| Centg2 | 347722 |
| Zfp260 | 26466 |
| Zfp281 | 226442 |
| Ptprk | 19272 |
| Ppp3ca | 19055 |

TABLE 9-continued

Off-Target Gene Identification

| Symbol | Gene ID |
|---|---|
| Adam32 | 353188 |
| Ppp1r1b | 19049 |
| Crip2 | 68337 |
| Ddc | 13195 |
| D630033O11Rik | 235302 |
| Chn2 | 69993 |
| BC018242 | 235044 |
| Ergic1 | 67458 |
| Mapkap1 | 227743 |
| Wwox | 80707 |
| Stx8 | 55943 |
| Bcas3 | 192197 |
| Exoc6b///Sec15l2 | 75914 |
| Ube2e2 | 218793 |
| Parva | 57342 |
| Agpat2 | 67512 |
| Adcy9 | 11515 |
| Pkp4 | 227937 |
| Pcbd2 | 72562 |
| Fbxl20 | 72194 |
| Scly | 50880 |
| Macrod1 | 107227 |
| Vti1a | 53611 |
| Abhd2 | 54608 |
| 4932417H02Rik | 74370 |
| Pgs1 | 74451 |
| Tmem162 | 76415 |
| Adk | 11534 |
| BC029169 | 208659 |
| Nedd4l | 83814 |
| Ank | 11732 |
| 1190005F20Rik | 98685 |
| Atg5 | 11793 |
| Gck | 103988 |
| Mgmt | 17314 |
| Adam23 | 23792 |
| Dym | 69190 |
| Pitpnm2 | 19679 |
| Nfib | 18028 |
| Bre | 107976 |
| Gphn | 268566 |
| Gapvd1 | 66691 |
| Fars2 | 69955 |
| Sfi1 | 78887 |
| Tulp4 | 68842 |
| Sds | 231691 |
| Sgms2 | 74442 |
| Exoc4 | 20336 |
| Pitpnc1 | 71795 |
| Tox | 252838 |
| Lrba | 80877 |
| Npb | 208990 |
| LOC100046025 | 100046025 |
| Myo1b | 17912 |
| Ppm1l | 242083 |
| Prnpip1 | 140546 |
| Pdzrn3 | 55983 |
| Atg7 | 74244 |
| Supt3h | 109115 |
| Hsd3b4 | 15495 |
| Cryl1 | 68631 |
| Ece1 | 230857 |
| Mrap | 77037 |
| Smoc1 | 64075 |
| Ext2 | 14043 |
| Ccdc91 | 67015 |
| Hamp | 84506 |
| LOC100036521 | 100036521 |
| Mnat1 | 17420 |
| Eps15l1 | 13859 |
| Alg14 | 66789 |
| Paqr7 | 71904 |
| Cdca7 | 66953 |
| Arntl | 11865 |
| Slc17a2 | 218103 |
| 2310009E04Rik | 75578 |

TABLE 9-continued

Off-Target Gene Identification

| Symbol | Gene ID |
|---|---|
| Lace1 | 215951 |
| BC057079 | 230393 |
| F7 | 14068 |
| 1810026J23Rik | 69773 |
| Uvrag | 78610 |
| Triobp | 110253 |
| Fto | 26383 |
| Herc2 | 15204 |
| Parn | 74108 |
| Fndc3b | 72007 |
| Sfxn5 | 94282 |
| Epb4.1 | 269587 |
| D930001I22Rik | 228859 |
| Immp2l | 93757 |
| Slc39a11 | 69806 |
| Hamp2 | 66438 |
| Rtp3 | 235636 |
| 6720458F09Rik | 328162 |
| Slc6a6 | 21366 |
| Dynll1 | 56455 |

Example 15

ALT and AST Toxicity

ALT and AST levels were measured in the remaining mice every 24 hours. All mice given Isis No. 457848 either were sacrificed after 48 hours or died before the 48 hour time point. Any remaining mice were then sacrificed at 96 hours. ALT and AST levels were measured by taking a sample of blood from each of the mice, centrifuging the sample, and then analyzing the plasma. ALT or AST levels greater than 10 times the baseline indicated toxicity.

TABLE 10

ALT Levels at 24 hours

| Treatment | | | ALT (IU/mL) | |
|---|---|---|---|---|
| Isis No. | Dose (mg/kg) | Duration (hours) | Mean | STDEV |
| Saline | 0 | 24 | 90 | 59 |
| 457847 | 100 | 24 | 41 | 16 |
| 457847 | 200 | 24 | 35 | 2 |
| 457848 | 100 | 24 | 41 | 6 |
| 457848 | 200 | 24 | 73 | 42 |

TABLE 11

ALT Levels at 48 hours

| Treatment | | | ALT (IU/mL) | |
|---|---|---|---|---|
| Isis No. | Dose (mg/kg) | Duration (hours) | Mean | STDEV |
| Saline | 0 | 48 | 63 | 63 |
| 457847 | 100 | 48 | 30 | 0 |
| 457847 | 200 | 48 | 35 | 7 |
| 457848 | 100 | 48 | 17717 | 4243 |
| 457848 | 200 | 48 | 16667 | NA |

TABLE 12

ALT Levels at 72 hours

| Treatment | | | ALT (IU/mL) | |
|---|---|---|---|---|
| Isis No. | Dose (mg/kg) | Duration (hours) | Mean | STDEV |
| Saline | 0 | 72 | 17 | 1 |
| 457847 | 100 | 72 | 178 | 64 |
| 457847 | 200 | 72 | 284 | 180 |
| 457848 | 100 | 72 | Lethal | NA |
| 457848 | 200 | 72 | Lethal | NA |

TABLE 13

ALT Levels at 96 hours

| Treatment | | | ALT (IU/mL) | |
|---|---|---|---|---|
| Isis No. | Dose (mg/kg) | Duration (hours) | Mean | STDEV |
| Saline | 0 | 96 | 24 | 4 |
| 457847 | 100 | 96 | 1632 | 775 |
| 457847 | 200 | 96 | 15267 | 2620 |
| 457848 | 100 | 96 | Lethal | NA |
| 457848 | 200 | 96 | Lethal | NA |

TABLE 14

AST Levels at 24 hours

| Treatment | | | AST (IU/mL) | |
|---|---|---|---|---|
| Isis No. | Dose (mg/kg) | Duration (hours) | Mean | STDEV |
| Saline | 0 | 24 | 113 | 46 |
| 457847 | 100 | 24 | 85 | 27 |
| 457847 | 200 | 24 | 75 | 13 |
| 457848 | 100 | 24 | 104 | 21 |
| 457848 | 200 | 24 | 91 | 35 |

TABLE 15

AST Levels at 48 hours

| Treatment | | | AST (IU/mL) | |
|---|---|---|---|---|
| Isis No. | Dose (mg/kg) | Duration (hours) | Mean | STDEV |
| Saline | 0 | 48 | 116 | 157 |
| 457847 | 100 | 48 | 98 | 37 |
| 457847 | 200 | 48 | 87 | 32 |
| 457848 | 100 | 48 | 16735 | 3426 |
| 457848 | 200 | 48 | 19859 | NA |

TABLE 16

AST Levels at 72 hours

| Treatment | | | AST (IU/mL) | |
|---|---|---|---|---|
| Isis No. | Dose (mg/kg) | Duration (hours) | Mean | STDEV |
| Saline | 0 | 72 | 27 | 3 |
| 457847 | 100 | 72 | 157 | 84 |
| 457847 | 200 | 72 | 164 | 65 |
| 457848 | 100 | 72 | Lethal | NA |
| 457848 | 200 | 72 | Lethal | NA |

TABLE 17

AST Levels at 96 hours

| Treatment | | | AST (IU/mL) | |
|---|---|---|---|---|
| Isis No. | Dose (mg/kg) | Duration (hours) | Mean | STDEV |
| Saline | 0 | 96 | 41 | 3 |
| 457847 | 100 | 96 | 1026 | 538 |
| 457847 | 200 | 96 | 9480 | 3094 |
| 457848 | 100 | 96 | Lethal | NA |
| 457848 | 200 | 96 | Lethal | NA |

Example 16

Correlation Between Off-Target Gene Modulation and Toxicity: Overlapping Off-Target Genes The degree of the change in modulation of amount or activity of each of the 143 overlapping off-target genes shown in Table 9 may be correlated with the amount of acute toxicity. For example, these off-target genes may be correlated with the increase in AST or ALT levels described in Example 15. Identifying the off-target genes having the highest correlation between the degree of modulation of amount or activity of expression and acute toxicity would yield a sub-set of genes of interest for further in-vitro validation.

Example 17

In Vitro Validation of Off-Target Genes and Identification and Selection of Sentinel Genes After identifying a sub-set of off-target genes of interest for further in-vitro validation, in vitro cells may be used to validate the sub-set of off-target genes, for example, in vitro cells may be used to validate the 143 overlapping off-target genes shown in Table 9.

For example, to validate the 143 overlapping off-target genes shown in Table 9, primary hepatocytes from male Balb/c mice would be isolated. The isolated hepatocytes would be electroporated with water or Isis No. 457848 or Isis No. 457847 at concentrations of 15 µM. At 2.5 hours after electroporation, the cells would then be refed with 100 µM of warm growth medium. At 16 hours after electroporation, the cells would be washed and lysed with RLT+BME. The cells would then be shaken for 1 minute before sealing and freesing at −80° C. Lysate would be used to purify the cells for RT-PCR analysis and genes would be measured by RT-PCR and Ribogreen and UV are read for each sample.

After obtaining the RT-PCR analysis of off-target genes that demonstrated strong amounts of modulation of amount or activity in vivo, the off-target genes that also show strong amounts of modulation of amount or activity in vitro may now be identified. For example, if one of the overlapping off-target genes shows a strong amount of down regulation in vivo upon the administration of a given oligonucleotide, and also demonstrates a strong amount of down regulation in vitro when administered the same oligonucleotide, then this off-target gene may be identified as a good indicator of toxicity (e.g. sentinel gene). Now, one can administer a cell any number of different oligonucleotides having any number of motifs and modifications, and then monitor the regulation of the identified off-target gene by RT-PCR or any other suitable method known to those having skill in the art. In this manner the in vivo toxicity of any number of different

Example 18

Correlation Between Off-Target Gene Modulation and Toxicity: Isis No. 457848

The degree of modulation of amount or activity each of the 1617 off-target genes identified after administration of 100 mg/kg of Isis No. 457848 may be correlated with the degree of increase in acute toxicity. For example, these off-target genes may be correlated with an increase in AST or ALT levels. Identifying the off-target genes having the highest correlation between modulation of amount or activity and acute toxicity would yield a sub-set of genes of interest for further in-vitro validation as detailed in Example 11 above.

Example 19

Correlation Between Off-Target Gene Modulation and Toxicity: Isis No. 457847

The degree of modulation of amount or activity of each of the 225 off-target genes identified after administration of 200 mg/kg of Isis No. 457847 may be correlated with the degree of increase in acute toxicity. For example, these off-target genes may be correlated with an increase in AST or ALT levels. Identifying the off-target genes having the highest correlation between modulation of amount or activity and acute toxicity would yield a sub-set of genes of interest for further in-vitro validation as detailed in Example 11 above.

Example 20

3-10-3 LNA Gapmers

The following 3-10-3 LNA gapmers were prepared using the procedures as described above. A subscript "1" indicates a nucleoside comprising a bicyclic sugar moiety comprising a 4'-$CH_2$—O-2'bridge. Each of the gapmers below have a full phosphorothioate backbone. Table 18 below illustrates the sequences and targets of each compound.

TABLE 18

3-10-3 LNA Gapmers

| Isis No. | Target | Sequence | SEQ ID NO. |
|---|---|---|---|
| 569713 | NA/ASO ctrl | $G_1A_1C_1$GCGCCTGAAGG$_1T_1T_1$ | 7 |
| 571035 | FVII | $C_1A_1G_1$ATATAGGACTG$_1G_1A_1$ | 8 |
| 571033 | FXI | $A_1T_1C_1$CAGAGATGCCT$_1C_1C_1$ | 9 |
| 569714 | FXI | $G_1G_1C_1$CACCACGCTGT$_1C_1A_1$ | 10 |
| 571034 | FXI | $T_1G_1C_1$CACCGTAGACA$_1C_1G_1$ | 11 |
| 569715 | SOD1 | $G_1G_1A_1$CACATTGGCCA$_1C_1A_1$ | 12 |
| 569716 | FVII | $C_1C_1C_1$TGGTGTACACC$_1C_1C_1$ | 13 |
| 569717 | PTEN | $A_1T_1C_1$ATGGCTGCAGC$_1T_1T_1$ | 14 |
| 569718 | FVII | $T_1G_1G_1$TCCCTGCAGTA$_1C_1T_1$ | 15 |

TABLE 18-continued

3-10-3 LNA Gapmers

| Isis No. | Target | Sequence | SEQ ID NO. |
|---|---|---|---|
| 569719 | FXI | $G_1T_1C_1$TGTGCATCTCT$_1C_1C_1$ | 16 |
| 569720 | FXI | $G_1T_1C_1$AGTATCCCAGT$_1G_1T_1$ | 17 |
| 569721 | SOD1 | $T_1G_1A_1$GGTCCTGCACT$_1G_1G_1$ | 18 |
| 554219 | Survivin | $C_1T_1C_1A_1$ATCCATGGC$_1A_1G_1$C | 19 |

Example 21

Off-Target Analysis of 3-10-3 LNA Gapmers

A series of antisense LNA containing oligonucleotides targeting a broad range of targets were designed and synthesized as described above. Balb/c mice were separated into different groups and each group of mice was subcutaneously administered saline, or a single dose of Isis No. 569713, 571035, 571033, 569714, 571034, 569715, 569716, 569717, 569718, 569719, 569720, 569721, or 554219. In order to create a dose-respone curve, the mice in each group were administered single doses of Isis No. 569713, 571035, 571033, 569714, 571034, 569715, 569716, 569717, 569718, 569719, 569720, 569721, and 554219 at different concentrations ranging from 1 mg/kg to 300 mg/kg. At 24 hours post administration, half of the mice in each group for each dosage concentration were sacrificed. Immediately after each mouse was sacrificed, the livers were frozen in liquid nitrogen and then sent to Expression Analysis (Durham, N.C.) for whole genome expression. Gene expression analysis on each of livers of the sacrificed mice was performed using a microarray to obtain whole genome profiling. For each of the mice that were not sacrificed, samples were taken and ALT and AST levels were measured. Animals found dead prior to 96 hours were assigned an ALT value of 20000 IU/mL. A dose-response curve was then generated that plotted dose concentration (mg/kg) vs. ALT levels (IU/mL). The dose response curve for each of Isis No. 569713, 571035, 571033, 569714, 571034, 569715, 569716, 569717, 569718, 569719, 569720, 569721, or 554219 was then analyzed and used to calculate the minimum dosage required to produce 1000 IU/ml ALT at 96 h. As the table below illustrates, doses ranging from 11 mg/kg to 300 mg/kg resulted in ALT levels greater than 1000 IU/ml for 7 compounds: Isis Nos. 569716, 569717, 569718, 569719, 569720, 569721, and 554219. The remaining compounds did not produce ALT levels greater than 1000 IU/ml, even after a single dose of 300 mg/kg.

TABLE 19

1st Toxic Dose (mg/kg) > 1000 IU/ml ALT at 96 h

| Isis No. | Target | On-Target Species | Dose (mg/kg) | 1st Toxic Dose (mg/kg) > 1000 IU/ml ALT at 96 h | SEQ ID NO. |
|---|---|---|---|---|---|
| 569713 | NA/ASO Ctrl | Mouse | 300 | >300 | 7 |
| 571035 | FVII | Human | 300 | >300 | 8 |
| 571033 | FXI | Mouse | 300 | >300 | 9 |
| 569714 | FXI | Mouse | 300 | >300 | 10 |
| 571034 | FXI | Mouse | 300 | >300 | 11 |
| 569715 | SOD1 | Mouse | 300 | >300 | 12 |

TABLE 19-continued

1st Toxic Dose (mg/kg) > 1000 IU/ml ALT at 96 h

| Isis No. | Target | On-Target Species | Dose (mg/kg) | 1st Toxic Dose (mg/kg) > 1000 IU/ml ALT at 96 h | SEQ ID NO. |
|---|---|---|---|---|---|
| 569716 | FVII | Mouse | 33 | 300 | 13 |
| 569717 | PTEN | Mouse | <33 | 33 | 14 |
| 569718 | FVII | Mouse | <33 | 100 | 15 |
| 569719 | FXI | Mouse | <11 | 11 | 16 |
| 569720 | FXI | Mouse | 33 | 100 | 17 |
| 569721 | SOD1 | Mouse | <33 | 33 | 18 |
| 554219 | Survivin | Human | 33 | 300 | 19 |

Example 22

Correlation Between Off-Target Gene Modulation and ALT Increase

Gene expression analysis on each of the mice sacrificed at 24 hours post-administration from Example 21 were analyzed. Expression of each gene on the array was normalized to saline control. The fold change of each downregulated gene as measured at 24 hours post administration was then correlated to the increase in ALT measured at 96 hours. The genes that illustrated the strongest correlation between down-regulation and an increase in ALT were then ranked according to $r^2$ values as illustrated in Table 20. Similarly, the genes that illustrated the strongest correlation between up-regulation and an increase in ALT were then ranked according to $r^2$ values as illustrated in Table 21.

TABLE 20

Down Regulated Genes Correlated to ALT Increase

| Entrez Gene ID | Gene Symbol | $r^2$ | Gene Regulation (Up or Down) |
|---|---|---|---|
| 74370 | 4932417H02Rik | 0.881570237 | Down |
| 75914 | mKIAA0919///Sec15l2///Exoc6b | 0.877706718 | Down |
| 50758 | Fbxl17 | 0.871834582 | Down |
| 69993 | Chn2 | 0.868472413 | Down |
| 26383 | Fto | 0.857328609 | Down |
| 666173 | AK053274///mKIAA0532///Vps13b///AK049111 | 0.852912584 | Down |
| 80877 | Lrba///Lba | 0.831826949 | Down |
| 69955 | Fars2 | 0.825377409 | Down |
| 217734 | Pomt2 | 0.816819711 | Down |
| 211652 | Wwc1 | 0.814841424 | Down |
| 66795 | Atg10 | 0.797656754 | Down |
| 14701 | Gng12 | 0.793469536 | Down |
| 103677 | Smg6 | 0.789202811 | Down |
| 224008 | 2310008H04Rik | 0.78792452 | Down |
| 19272 | Ptprk | 0.785719243 | Down |
| 320405 | Cadps2 | 0.785433781 | Down |
| 109115 | Supt3h | 0.782544958 | Down |
| 20441 | St3gal3 | 0.782160893 | Down |
| 74244 | Atg7 | 0.771958613 | Down |
| 75578 | Fggy | 0.770141201 | Down |
| 218793 | Ube2e2 | 0.768562158 | Down |
| 93757 | Immp2l | 0.766370426 | Down |
| 192197 | Bcas3 | 0.763707226 | Down |
| 17420 | Mnat1 | 0.763237657 | Down |
| 16439 | Itpr2 | 0.755316427 | Down |
| 11515 | Adcy9 | 0.752314856 | Down |
| 218103 | Slc17a2 | 0.751397383 | Down |
| 27414 | Sergef | 0.74669734 | Down |
| 64075 | Smoc1 | 0.745821158 | Down |
| 69190 | Dym | 0.745739189 | Down |
| 18027 | Nfia | 0.745678305 | Down |
| 23965 | Odz3 | 0.745633647 | Down |
| 209224 | Enox2 | 0.745318111 | Down |
| 72238 | Tbc1d5 | 0.74475067 | Down |
| 230393 | BC057079 | 0.743701723 | Down |
| 12808 | Cobl | 0.743510516 | Down |
| 76626 | Msi2 | 0.74312008 | Down |
| 13982 | Esr1 | 0.743009136 | Down |
| 58239 | Dexi | 0.741767493 | Down |
| 26936 | AA536749 | 0.740805736 | Down |
| 13640 | Efna5 | 0.738026555 | Down |
| 68975 | Med27 | 0.737264649 | Down |
| 68916 | Cdkal1 | 0.73405334 | Down |
| 50771 | Atp9b | 0.73127855 | Down |
| 16010 | Igfbp4 | 0.729708609 | Down |
| 20211 | Saa4 | 0.725536568 | Down |
| 72313 | Fryl | 0.723712037 | Down |
| 194401 | Mical3///Kiaa0819 | 0.722136142 | Down |
| 16438 | Itpr1 | 0.721919362 | Down |
| 242083 | AK031097///Ppm1l | 0.720131701 | Down |
| 93742 | Pard3 | 0.719281305 | Down |
| 17314 | Mgmt | 0.717297987 | Down |
| 97287 | Mtmr14 | 0.715716221 | Down |
| 18705 | Pik3c2g | 0.711058186 | Down |
| 72007 | Fndc3b | 0.707287944 | Down |
| 12361 | Cask | 0.706570871 | Down |
| 171212 | Galnt10 | 0.704933641 | Down |
| 223754 | Tbc1d22a | 0.703695636 | Down |
| 107227 | Macrod1 | 0.698975352 | Down |
| 74374 | Clec16a | 0.697481709 | Down |
| 208718 | Dis3l2 | 0.696060142 | Down |
| 74519 | Cyp2j9 | 0.695058095 | Down |
| 268534 | Sntg2 | 0.694530379 | Down |
| 81500 | Sil1 | 0.694446922 | Down |
| 219189 | 1300010F03Rik | 0.694202597 | Down |
| 13047 | Cux1 | 0.69203827 | Down |
| 68618 | 1110012L19Rik | 0.688947418 | Down |
| 140546 | Prnpip1 | 0.688766285 | Down |
| 20238 | Atxn1 | 0.68713467 | Down |
| 71111 | Gpr39 | 0.686579986 | Down |
| 14600 | Ghr | 0.683133879 | Down |
| 19266 | Ptprd | 0.679746496 | Down |
| 74155 | Errfi1 | 0.679613946 | Down |
| 227835 | AK137808///Gtdc1 | 0.678056969 | Down |
| 320940 | Atp11c | 0.677044007 | Down |
| 108099 | Prkag2 | 0.676318162 | Down |
| 239037 | Lrit1 | 0.676002874 | Down |
| 213988 | Tnrc6b | 0.672130399 | Down |
| 68178 | Cgnl1 | 0.67019584 | Down |
| 16795 | Large | 0.669312813 | Down |
| 268566 | Gphn | 0.663682789 | Down |
| 319845 | Bbs9 | 0.66198502 | Down |
| 18563 | Pcx | 0.659174176 | Down |
| 94040 | mKIAA1188///Clmn | 0.659028801 | Down |
| 229487 | Pet112l | 0.658191741 | Down |
| 78808 | Stxbp5 | 0.65802987 | Down |
| 14043 | Ext2 | 0.655674984 | Down |
| 94245 | Dtnbp1 | 0.653677345 | Down |
| 11881 | Arsb | 0.652843338 | Down |
| 224454 | Zdhhc14 | 0.651947144 | Down |
| 105559 | Mbnl2 | 0.650606525 | Down |
| 13528 | Dtnb | 0.65026389 | Down |
| 19679 | Pitpnm2 | 0.649808523 | Down |
| 15204 | Herc2 | 0.649722071 | Down |
| 18606 | Enpp2 | 0.648732736 | Down |
| 53611 | Vti1a | 0.645315814 | Down |
| 238130 | Dock4///mKIAA0716 | 0.644365345 | Down |
| 99586 | Dpyd | 0.643599698 | Down |
| 74008 | Arsg | 0.643248092 | Down |
| 110821 | Pcca | 0.642571153 | Down |
| 56463 | Snd1 | 0.640221713 | Down |
| 67015 | Ccdc91 | 0.637646731 | Down |
| 272428 | Acsm5 | 0.636080214 | Down |

TABLE 20-continued

Down Regulated Genes Correlated to ALT Increase

| Entrez Gene ID | Gene Symbol | $r^2$ | Gene Regulation (Up or Down) |
|---|---|---|---|
| 14886 | Gtf2i | 0.635173991 | Down |
| 69806 | Slc39a11 | 0.634795581 | Down |
| 110532 | Adarb1 | 0.632312769 | Down |
| 54604 | Pcnx | 0.631496126 | Down |
| 319885 | Zcchc7 | 0.63146848 | Down |
| 102774 | Bbs4 | 0.630868233 | Down |
| 243537 | Uroc1 | 0.626857311 | Down |
| 12558 | Cdh2 | 0.626328157 | Down |
| 26396 | Map2k2 | 0.626020226 | Down |
| 233977 | BC038349 | 0.625763342 | Down |
| 98496 | 5033414K04Rik | 0.622537661 | Down |
| 269587 | Epb4.1 | 0.622028322 | Down |
| 330662 | Dock1 | 0.621512901 | Down |
| 75735 | Pank1 | 0.621009598 | Down |
| 54403 | Slc4a4 | 0.61967098 | Down |
| 278279 | Tmtc2 | 0.617639658 | Down |
| 228730 | Ncrna00153 | 0.617418242 | Down |
| 73652 | BC099512 | 0.616894972 | Down |
| 223254 | Farp1 | 0.616836211 | Down |
| 18028 | Nfib | 0.616081199 | Down |
| 213498 | Arhgef11 | 0.615577511 | Down |
| 14718 | Got1 | 0.614119517 | Down |
| 63955 | Cables1 | 0.613107576 | Down |
| 68801 | Elovl5 | 0.612792288 | Down |
| 74270 | Usp20 | 0.612454854 | Down |
| 17925 | Myo9b | 0.611954099 | Down |
| 83814 | Nedd4l///mKIAA0439 | 0.611375334 | Down |
| 74088 | 0610012H03Rik | 0.610067554 | Down |
| 233865 | D430042O09Rik | 0.609934771 | Down |
| 216565 | Ehbp1 | 0.609655313 | Down |
| 104718 | Ttc7b | 0.609371418 | Down |
| 20338 | Sel1l | 0.608270142 | Down |
| 271564 | Vps13a///CHAC | 0.608063281 | Down |
| 107986 | Ddb2 | 0.606166164 | Down |
| 672511 | Rnf213 | 0.605363852 | Down |
| 71602 | Myo1e | 0.604467637 | Down |
| 17175 | Masp2 | 0.603726298 | Down |
| 14585 | Gfra1 | 0.603632842 | Down |
| 15486 | Hsd17b2 | 0.603323943 | Down |
| 192786 | Rapgef6///mKIAA4052 | 0.60322277 | Down |
| 77987 | Ascc3///AK144867 | 0.602976597 | Down |
| 18750 | Prkca | 0.602949949 | Down |
| 57342 | Parva | 0.602253239 | Down |
| 14158 | Fert2 | 0.601937675 | Down |
| 29819 | Stau2 | 0.601830334 | Down |
| 227743 | Mapkap1 | 0.601738633 | Down |
| 241308 | AK140547///Ralgps1 | 0.599029779 | Down |
| 20678 | Sox5 | 0.59802968 | Down |
| 218865 | Chdh | 0.597817574 | Down |
| 17127 | Smad3 | 0.597594387 | Down |
| 54353 | Skap2 | 0.597275862 | Down |
| 17120 | Mad1///Mad1l1 | 0.597192128 | Down |
| 55983 | Pdzrn3 | 0.596823197 | Down |
| 239985 | Arid1b | 0.596763305 | Down |
| 104816 | Aspg | 0.596526332 | Down |
| 11749 | Anxa6 | 0.59605341 | Down |
| 211673 | Arfgef1 | 0.594411456 | Down |
| 50785 | Hs6st1 | 0.593828373 | Down |
| 71302 | Arhgap26///mKIAA0621 | 0.593619374 | Down |
| 104082 | Wdr7 | 0.592931146 | Down |
| 100637 | B230342M21Rik///N4bp2l1 | 0.592696965 | Down |
| 65973 | Asph | 0.592305859 | Down |
| 544963 | Iqgap2 | 0.591705376 | Down |
| 320011 | Ugcgl1 | 0.5897969 | Down |
| 70661 | BC033915 | 0.58976308 | Down |
| 215445 | mKIAA0665///Rab11fip3 | 0.589224941 | Down |
| 20679 | Sox6 | 0.588615413 | Down |
| 76454 | Fbxo31 | 0.588503735 | Down |
| 68889 | Ubac2 | 0.587940107 | Down |
| 94353 | Hmgn3 | 0.586699681 | Down |
| 228602 | 4930402H24Rik | 0.586564331 | Down |
| 108655 | Foxp1 | 0.586468849 | Down |
| 171486 | Cd99l2 | 0.586443991 | Down |
| 223978 | C530044N13Rik///Cpped1 | 0.585623518 | Down |
| 76510 | Trappc9///1810044A24Rik | 0.582060196 | Down |
| 29809 | Rabgap1l | 0.581796202 | Down |
| 21372 | Tbl1x | 0.581345739 | Down |
| 23908 | Hs2st1 | 0.581201637 | Down |
| 102566 | Tmem16k///Ano10 | 0.579746255 | Down |
| 347722 | Agap1 | 0.579494425 | Down |
| 23938 | Map2k5 | 0.579447394 | Down |
| 96935 | Susd4 | 0.578851694 | Down |
| 56878 | Rbms1///AK011205 | 0.578650042 | Down |
| 100036521 | Gig18 | 0.578509922 | Down |
| 74440 | 4933407C03Rik///mKIAA1694 | 0.578167843 | Down |
| 102644 | Oaf | 0.577524669 | Down |
| 54725 | Cadm1 | 0.576998479 | Down |
| 22084 | Tsc2 | 0.576392104 | Down |
| 56490 | Zbtb20 | 0.575959654 | Down |
| 66253 | Aig1 | 0.5755063 | Down |
| 246196 | Zfp277///AK172713 | 0.575391946 | Down |
| 18201 | Nsmaf | 0.573842299 | Down |
| 19045 | Ppp1ca | 0.573112804 | Down |
| 22325 | Vav2 | 0.57267834 | Down |
| 23945 | Mgll | 0.572572051 | Down |
| 26930 | Ppnr | 0.571883753 | Down |
| 76429 | 2310007H09Rik | 0.570953791 | Down |
| 231051 | Mll3 | 0.57076196 | Down |
| 93834 | Peli2 | 0.570020747 | Down |
| 70834 | Spag9///JSAP2 | 0.56678755 | Down |
| 12385 | Ctnna1 | 0.566049233 | Down |
| 20409 | Ostf1 | 0.565624252 | Down |
| 52398 | 11-Sep | 0.563024508 | Down |
| 17158 | Man2a1 | 0.563022255 | Down |
| 18099 | Nlk | 0.562409972 | Down |
| 216831 | AU040829 | 0.561880909 | Down |
| 11787 | Apbb2 | 0.561732807 | Down |
| 68501 | Nsmce2 | 0.561289726 | Down |
| 224671 | Btbd9 | 0.56054694 | Down |
| 229877 | Rap1gds1 | 0.560281909 | Down |
| 68631 | Cryl1 | 0.560090087 | Down |
| 24059 | Slco2a1 | 0.560080102 | Down |
| 22222 | Ubr1 | 0.559857296 | Down |
| 68732 | Lrrc16a///Lrrc16 | 0.559393676 | Down |
| 67074 | Mon2 | 0.559331869 | Down |
| 50754 | Fbxw7 | 0.559122106 | Down |
| 19055 | Ppp3ca | 0.558920628 | Down |
| 107476 | AK040794///Acaca | 0.558791978 | Down |
| 17155 | Man1a | 0.558773698 | Down |
| 207181 | Rbms3 | 0.558605596 | Down |
| 68465 | Adipor2 | 0.558226759 | Down |
| 20192 | Ryr3 | 0.557339048 | Down |
| 29807 | Tpk1 | 0.557197421 | Down |
| 18624 | Pepd | 0.557093355 | Down |
| 71764 | C2cd2l | 0.555663167 | Down |
| 432442 | Akap7 | 0.55457384 | Down |
| 103220 | BC030307 | 0.554449533 | Down |
| 105428 | Fam149b | 0.554372745 | Down |
| 20747 | Spop | 0.554035756 | Down |
| 108138 | Xrcc4 | 0.55386123 | Down |
| 208440 | Dip2c | 0.553415197 | Down |
| 75472 | 1700009P17Rik | 0.553150905 | Down |
| 72599 | Pdia5 | 0.552830011 | Down |
| 18534 | Pck1 | 0.552604806 | Down |
| 68299 | Vps53 | 0.552307087 | Down |
| 65967 | Eefsec | 0.549508286 | Down |
| 68371 | Pbld | 0.547859009 | Down |
| 227801 | Dennd1a | 0.547051646 | Down |
| 17977 | Ncoa1 | 0.545367828 | Down |
| 60344 | Fign | 0.54532852 | Down |

TABLE 21

Up Regulated Genes Correlated to ALT Increase

| Entrez Gene ID | Gene Symbol | r² | Gene Regulation (Up or Down) |
|---|---|---|---|
| 321000 | 4933421E11Rik | 0.828781401 | Up |
| 71989 | Rpusd4 | 0.821214015 | Up |
| 68185 | AK019895///Chchd8 | 0.812766903 | Up |
| 52477 | Angel2 | 0.809563061 | Up |
| 14911 | Thumpd3 | 0.804718994 | Up |
| 69241 | Polr2d | 0.80039532 | Up |
| 13197 | Gadd45a | 0.792167641 | Up |
| 107522 | Ece2 | 0.784864986 | Up |
| 69549 | 2310009B15Rik | 0.784498393 | Up |
| 68550 | 1110002N22Rik | 0.783538519 | Up |
| 233904 | Setd1a | 0.763731607 | Up |
| 69961 | 2810432D09Rik | 0.758340494 | Up |
| 66870 | Serbp1 | 0.752501221 | Up |
| 67101 | 2310039H08Rik | 0.747968837 | Up |
| 270058 | Mtap1s | 0.744064198 | Up |
| 27260 | Plek2 | 0.741994766 | Up |
| 69168 | Bola1 | 0.738818242 | Up |
| 68115 | AK172713///9430016H08Rik | 0.738387466 | Up |
| 73419 | 1700052N19Rik | 0.738021033 | Up |
| 74132 | Rnf6 | 0.734273477 | Up |
| 105663 | Thtpa | 0.73343318 | Up |
| 227102 | Ormdl1 | 0.730356662 | Up |
| 243219 | 2900026A02Rik | 0.728731593 | Up |
| 20020 | Polr2a | 0.727986948 | Up |
| 22629 | Ywhah | 0.727808243 | Up |
| 16668 | Krt18 | 0.727121927 | Up |
| 100515 | Zfp518b | 0.724764518 | Up |
| 66701 | Spryd4 | 0.722478849 | Up |
| 104457 | 0610010K14Rik | 0.717842951 | Up |
| 328099 | AU021838///Mipol1 | 0.715445754 | Up |
| 353188 | Adam32 | 0.71430195 | Up |
| 69962 | 2810422O20Rik | 0.713719025 | Up |
| 19039 | Lgals3bp | 0.713151192 | Up |
| 353258 | Ltv1 | 0.710511059 | Up |
| 68636 | Fahd1 | 0.709898912 | Up |
| 68327 | 0610007P22Rik | 0.709257388 | Up |
| 107701 | Sf3b4 | 0.706098027 | Up |
| 218952 | Fermt2 | 0.702510392 | Up |
| 448850 | Znhit3 | 0.702398526 | Up |
| 69228 | Znf746 | 0.700863921 | Up |
| 71787 | Trnau1ap | 0.700801498 | Up |
| 270106 | Rpl13 | 0.700293178 | Up |
| 68193 | Rpl24 | 0.699970694 | Up |
| 18590 | Pdgfa | 0.699591372 | Up |
| 66664 | Tmem41a | 0.698860497 | Up |
| 208518 | Cep78 | 0.698481328 | Up |
| 67781 | Ilf2 | 0.698448036 | Up |
| 70291 | 2510049J12Rik | 0.69714475 | Up |
| 67489 | Ap4b1 | 0.692430642 | Up |
| 76497 | Ppp1r11 | 0.691954689 | Up |
| 77038 | Arfgap2 | 0.690659625 | Up |
| 11676 | Aldoc | 0.687782385 | Up |
| 15574 | Hus1 | 0.687124907 | Up |
| 51792 | Ppp2r1a | 0.686680263 | Up |
| 66083 | Setd6 | 0.685885535 | Up |
| 22040 | AK036897///Trex1 | 0.685752435 | Up |
| 227522 | Rpp38 | 0.685477194 | Up |
| 70223 | Nars | 0.685365907 | Up |
| 28028 | Mrpl50 | 0.682327964 | Up |
| 17768 | Mthfd2 | 0.682320691 | Up |
| 69882 | 2010321M09Rik | 0.682121395 | Up |
| 66606 | Lrrc57 | 0.681908453 | Up |
| 231430 | Cox18 | 0.680319474 | Up |
| 22247 | Umps | 0.679307722 | Up |
| 11757 | Prdx3 | 0.678891516 | Up |
| 24110 | Usp18 | 0.678408208 | Up |
| 16391 | Isgf3g | 0.677375454 | Up |
| 68979 | Nol11 | 0.676746807 | Up |
| 66653 | Brf2 | 0.676339046 | Up |
| 67738 | Ppid | 0.676289037 | Up |
| 50918 | Myadm | 0.674621176 | Up |
| 16691 | Krt8 | 0.674433977 | Up |
| 69534 | Avpi1 | 0.673529456 | Up |
| 19340 | Rab3d | 0.670975146 | Up |
| 15374 | Hn1 | 0.670724081 | Up |
| 70020 | Ino80b | 0.670427391 | Up |
| 69573 | 2310016C08Rik | 0.668340356 | Up |
| 66596 | Gtf3a | 0.667461159 | Up |
| 83701 | Srrt | 0.666193892 | Up |
| 50887 | Nsbp1 | 0.664511092 | Up |
| 245841 | Polr2h | 0.663503343 | Up |
| 68512 | Tomm5 | 0.662237729 | Up |
| 55963 | Slc1a4 | 0.661815979 | Up |
| 67832 | Bxdc2 | 0.660961873 | Up |
| 276919 | Gemin4 | 0.660309894 | Up |
| 56716 | Gbl | 0.658651254 | Up |
| 100554 | C87414///AA792892 | 0.658411355 | Up |
| 235302 | AK052711 | 0.657733584 | Up |
| 78394 | Ddx52 | 0.656175645 | Up |
| 12238 | Commd3 | 0.655418374 | Up |
| 108037 | Shmt2 | 0.655013627 | Up |
| 69071 | Tmem97 | 0.654795198 | Up |
| 64406 | Sp5 | 0.654602739 | Up |
| 68147 | Gar1 | 0.654371413 | Up |
| 71988 | Esco2 | 0.653785092 | Up |
| 66962 | 2310047B19Rik | 0.653171224 | Up |
| 74097 | Pop7 | 0.652820242 | Up |
| 53317 | Plrg1 | 0.650910996 | Up |
| 12464 | Cct4 | 0.650849041 | Up |
| 20308 | Ccl9 | 0.650463831 | Up |
| 18950 | Pnp1 | 0.647576204 | Up |
| 68145 | Etaa1 | 0.646511359 | Up |
| 76560 | Prss8 | 0.645826963 | Up |
| 19671 | Rce1 | 0.645558171 | Up |
| 216825 | Usp22 | 0.644677729 | Up |
| 20174 | Ruvbl2 | 0.644207037 | Up |
| 23918 | Impdh2 | 0.644160463 | Up |
| 208990 | Npb | 0.643688534 | Up |
| 227715 | Exosc2 | 0.643331854 | Up |
| 71916 | Dus4l | 0.642261732 | Up |
| 69479 | 1700029J07Rik | 0.641809029 | Up |
| 58248 | 1700123O20Rik | 0.641420014 | Up |
| 66401 | Nudt2 | 0.640767939 | Up |
| 79554 | Gltpd1 | 0.640567138 | Up |
| 83703 | Dbr1 | 0.64042371 | Up |
| 27356 | Insl6 | 0.638467326 | Up |
| 20102 | Rps4x | 0.6383911 | Up |
| 66658 | Ccdc51 | 0.637337398 | Up |
| 69902 | Mrto4 | 0.637181622 | Up |
| 56209 | Gde1 | 0.637166586 | Up |
| 71059 | Hexim2 | 0.635654881 | Up |
| 234776 | Atmin | 0.635066457 | Up |
| 74026 | Msl1 | 0.63337818 | Up |
| 97541 | Qars | 0.632918392 | Up |
| 225913 | Dak | 0.632596985 | Up |
| 105278 | Ccrk | 0.632551012 | Up |
| 76813 | Armc6 | 0.632428466 | Up |
| 75078 | 2810008M24Rik | 0.63153931 | Up |
| 75623 | Kdelc1///1700029F09Rik | 0.631128792 | Up |
| 57357 | Srd5a3 | 0.630154401 | Up |
| 233876 | Hirip3 | 0.629817864 | Up |
| 97159 | A430005L14Rik | 0.628500508 | Up |
| 230234 | BC026590 | 0.628443782 | Up |
| 12739 | Cldn3///Wbscr25 | 0.628153864 | Up |
| 232337 | Zfp637 | 0.627445127 | Up |
| 14156 | Fen1 | 0.62707061 | Up |
| 66248 | Alg5 | 0.626283145 | Up |
| 227154 | Als2cr2///Stradb | 0.626171704 | Up |
| 622707 | Rpl29 | 0.625940105 | Up |
| 64295 | Tmub1 | 0.62580345 | Up |
| 26961 | Rpl8 | 0.624738153 | Up |
| 22666 | Zfp161 | 0.62395442 | Up |
| 28010 | D4Wsu114e | 0.623435791 | Up |
| 71986 | Ddx28 | 0.623316076 | Up |
| 18148 | Npm1 | 0.622979601 | Up |
| 77286 | Nkrf | 0.622712352 | Up |

TABLE 21-continued

Up Regulated Genes Correlated to ALT Increase

| Entrez Gene ID | Gene Symbol | r² | Gene Regulation (Up or Down) |
|---|---|---|---|
| 68002 | 1110058L19Rik | 0.622440056 | Up |
| 227644 | Snapc4 | 0.622065994 | Up |
| 79059 | Nme3 | 0.621781774 | Up |
| 226153 | Peo1 | 0.621769908 | Up |
| 19921 | Rpl19 | 0.621648931 | Up |
| 18515 | Pbx2 | 0.621321591 | Up |
| 664968 | 2210411K11Rik | 0.620986253 | Up |
| 67097 | Rps10 | 0.62018374 | Up |
| 100040298 | Rps8 | 0.620012694 | Up |
| 230082 | Nol6 | 0.619384089 | Up |
| 66481 | Rps21 | 0.619315838 | Up |
| 15495 | Hsd3b4 | 0.619240278 | Up |
| 214424 | Parp16 | 0.618433307 | Up |
| 18483 | Palm | 0.617369158 | Up |
| 22051 | Trip6 | 0.617293652 | Up |
| 217700 | Acot6 | 0.617209221 | Up |
| 68644 | Abhd14a | 0.61700942 | Up |
| 18100 | Mrpl40 | 0.616505506 | Up |
| 20042 | Rps12 | 0.616251041 | Up |
| 217057 | Ptrh2 | 0.615272427 | Up |
| 20821 | Trim21 | 0.614943327 | Up |
| 67602 | Necap1 | 0.613081792 | Up |
| 231386 | Ythdc1 | 0.612826851 | Up |
| 68080 | Gpn3 | 0.612417706 | Up |
| 67996 | Sfrs6 | 0.611610127 | Up |
| 27370 | ENSMUSG00000059775///Rps26 | 0.610651846 | Up |
| 69912 | Nup43 | 0.610583513 | Up |
| 19826 | Rnps1 | 0.610497157 | Up |
| 101739 | Psip1 | 0.609866248 | Up |
| 399566 | Btbd6 | 0.609659323 | Up |
| 52626 | Cdkn2aipnl | 0.608900685 | Up |
| 19989 | Rpl7 | 0.607843346 | Up |
| 13667 | Eif2b4 | 0.607447824 | Up |
| 26441 | Psma4 | 0.607302102 | Up |
| 22758 | Zscan12 | 0.605678685 | Up |
| 667682 | Rpl31 | 0.605360844 | Up |
| 211255 | Kbtbd7 | 0.605148748 | Up |
| 69185 | Dtwd1 | 0.605123393 | Up |
| 320226 | 4930473A06Rik///AK029637 | 0.604141033 | Up |
| 216760 | Mfap3 | 0.603674722 | Up |
| 67736 | Ccdc130 | 0.603600403 | Up |
| 216150 | Cdc34 | 0.603551354 | Up |
| 65972 | Ifi30 | 0.603338123 | Up |
| 68044 | Chac2 | 0.602240646 | Up |
| 70240 | Ufsp1 | 0.601764375 | Up |
| 67242 | Gemin6 | 0.601630906 | Up |
| 16145 | Igtp | 0.601376355 | Up |
| 56503 | Ankrd49 | 0.600941885 | Up |
| 214489 | AK206957///AK050697 | 0.600265025 | Up |
| 269336 | Ccdc32 | 0.600259909 | Up |
| 208595 | ENSMUSG00000053178 | 0.6002454 | Up |
| 269955 | Rccd1 | 0.600195992 | Up |
| 66172 | Med11 | 0.600137828 | Up |
| 100040353 | 2810416G20Rik | 0.600052118 | Up |
| 14070 | F8a | 0.599086685 | Up |
| 66757 | Adat2 | 0.598703368 | Up |
| 20229 | Sat1 | 0.598621988 | Up |
| 70650 | Zcchc8 | 0.59793997 | Up |
| 52830 | Pnrc2 | 0.597172683 | Up |
| 68366 | Tmem129 | 0.596902461 | Up |
| 64655 | Mrps22 | 0.596839038 | Up |
| 223626 | 4930572J05Rik | 0.596704273 | Up |
| 269261 | Rpl12 | 0.596680782 | Up |
| 225280 | Ino80c | 0.59649754 | Up |
| 66953 | Cdca7 | 0.596271741 | Up |
| 231915 | Uspl1 | 0.596199279 | Up |
| 208768 | BC031781 | 0.595639474 | Up |
| 72275 | 2200002D01Rik | 0.595226971 | Up |
| 192231 | Hexim1 | 0.595082591 | Up |
| 208967 | Thnsl1 | 0.594889153 | Up |
| 381792 | AK009724 | 0.593903234 | Up |
| 77862 | Thyn1///mThy28 | 0.593293926 | Up |
| 68879 | Prpf6 | 0.592652691 | Up |
| 108098 | Med21 | 0.592576963 | Up |
| 22381 | Wbp5 | 0.592072955 | Up |
| 105148 | Iars | 0.592040457 | Up |
| 68294 | Mfsd10 | 0.591390672 | Up |
| 70021 | Nt5dc2 | 0.590503402 | Up |
| 69861 | 2010003K11Rik | 0.590433914 | Up |
| 67676 | Rpp21 | 0.589799041 | Up |
| 16205 | Gimap1 | 0.588793908 | Up |
| 66985 | Rassf7 | 0.588743485 | Up |
| 217140 | Scrn2 | 0.588506321 | Up |
| 70333 | Cd3eap | 0.588454054 | Up |
| 240514 | Ccdc85b | 0.588420718 | Up |
| 109163 | AK087382 | 0.588267639 | Up |
| 56088 | Psmg1 | 0.588101108 | Up |
| 108147 | Atic | 0.58752055 | Up |
| 67706 | Tmem179b | 0.587035814 | Up |
| 67136 | Kbtbd4 | 0.58667231 | Up |
| 212090 | Tmem60 | 0.585540086 | Up |
| 72655 | 2810026P18Rik | 0.584433095 | Up |
| 449521 | Zfp213 | 0.584222958 | Up |
| 107047 | Psmg2 | 0.582393668 | Up |
| 231841 | AA881470 | 0.581273744 | Up |
| 66656 | Eef1d | 0.581247585 | Up |
| 66170 | Chchd5 | 0.581205624 | Up |
| 56791 | Ube2l6 | 0.581062896 | Up |
| 14865 | Gstm4 | 0.58002253 | Up |
| 21339 | Taf1a | 0.579742839 | Up |
| 231583 | Slc26a1 | 0.579592368 | Up |
| 57837 | Eral1 | 0.579409625 | Up |
| 27395 | Mrpl15///AK017820 | 0.578731847 | Up |
| 69216 | Ccdc23 | 0.578281126 | Up |
| 14113 | Fbl | 0.578077881 | Up |
| 232236 | C130022K22Rik | 0.57804613 | Up |
| 554292 | LOC554292 | 0.577954571 | Up |
| 66973 | Mrps18b | 0.577310846 | Up |
| 66343 | Tmem177 | 0.577302833 | Up |
| 59053 | Brp16 | 0.577115872 | Up |
| 380712 | Tlcd2 | 0.576999831 | Up |
| 105014 | Rdh14 | 0.576469122 | Up |
| 226351 | Tmem185b | 0.575340901 | Up |
| 66489 | Rpl35 | 0.574558571 | Up |
| 66419 | Mrpl11 | 0.574368522 | Up |
| 213541 | Ythdf2 | 0.573980554 | Up |
| 18567 | Pdcd2 | 0.573748231 | Up |
| 26905 | Eif2s3x | 0.573638411 | Up |
| 11674 | Aldoa | 0.573198881 | Up |
| 14534 | Kat2a | 0.572866985 | Up |
| 66599 | Rdm1 | 0.57158232 | Up |
| 67186 | Rplp2 | 0.571268544 | Up |
| 219158 | 2610301G19Rik | 0.571254833 | Up |
| 100043000 | Rpl3 | 0.570441285 | Up |
| 21924 | Tnnc1 | 0.569822051 | Up |
| 18648 | Pgam1 | 0.569389772 | Up |
| 71726 | Smug1 | 0.569262976 | Up |
| 66358 | 2310004I24Rik | 0.569017971 | Up |
| 60406 | Sap30 | 0.568829534 | Up |
| 68949 | 1500012F01Rik | 0.568756138 | Up |
| 101943 | Sf3b3 | 0.568595763 | Up |
| 72536 | Tagap///Tagap1 | 0.568292844 | Up |
| 72388 | Ripk4 | 0.568112975 | Up |
| 15931 | BC160215///Ids | 0.568096931 | Up |
| 234309 | Cbr4 | 0.568058926 | Up |
| 76800 | Usp42 | 0.567858939 | Up |
| 22059 | Trp53 | 0.566787444 | Up |
| 19175 | Psmb6 | 0.565451493 | Up |
| 213233 | Tapbpl | 0.565247118 | Up |
| 231872 | Jtv1 | 0.5650143 | Up |
| 16549 | Khsrp | 0.56470297 | Up |
| 231655 | Oasl1 | 0.564257429 | Up |
| 15239 | Hgs | 0.564155733 | Up |
| 67427 | Rps20 | 0.564113737 | Up |
| 15270 | H2afx | 0.563830152 | Up |

TABLE 21-continued

Up Regulated Genes Correlated to ALT Increase

| Entrez Gene ID | Gene Symbol | r² | Gene Regulation (Up or Down) |
|---|---|---|---|
| 19172 | Psmb4 | 0.563063414 | Up |
| 21816 | Tgm1 | 0.562841486 | Up |
| 13163 | Daxx | 0.562685101 | Up |
| 24045 | Clk2///Scamp3 | 0.562455587 | Up |
| 225027 | Sfrs7 | 0.562278505 | Up |
| 67843 | Slc35a4 | 0.560934038 | Up |
| 214987 | Chtf8 | 0.560908881 | Up |
| 23877 | Fiz1 | 0.560848911 | Up |
| 78372 | Snrnp25 | 0.560175416 | Up |
| 52440 | Tax1bp1 | 0.559550144 | Up |
| 53902 | Rcan3 | 0.559014128 | Up |
| 69269 | Scnm1 | 0.558513651 | Up |
| 12812 | Coil | 0.558208066 | Up |
| 97484 | Cog8 | 0.557842373 | Up |
| 12567 | Cdk4 | 0.557273744 | Up |
| 27756 | Lsm2 | 0.557213698 | Up |
| 23849 | Klf6 | 0.556951617 | Up |
| 12469 | Cct8 | 0.556929134 | Up |
| 66910 | Tmem107 | 0.556716411 | Up |
| 57741 | Noc2l | 0.556220338 | Up |
| 67211 | Armc10 | 0.556028811 | Up |
| 97031 | C430004E15Rik | 0.555933123 | Up |
| 57785 | Rangrf | 0.555885298 | Up |
| 210973 | Kbtbd2 | 0.555784936 | Up |
| 16210 | Impact | 0.555775361 | Up |
| 67390 | Rnmtl1 | 0.555625742 | Up |
| 14272 | Fnta | 0.555039858 | Up |
| 76650 | Srxn1 | 0.554132183 | Up |
| 67053 | Rpp14 | 0.554111651 | Up |
| 68763 | AK003073 | 0.554047447 | Up |
| 66480 | Rpl15 | 0.55308007 | Up |
| 382423 | ENSMUSG00000074747 | 0.552900656 | Up |
| 12366 | Casp2 | 0.552565452 | Up |
| 101565 | 6330503K22Rik | 0.552523353 | Up |
| 327959 | Xafl | 0.552462295 | Up |
| 56361 | Pus1 | 0.552350536 | Up |
| 108660 | Rnf187 | 0.552206839 | Up |
| 56412 | 2610024G14Rik | 0.551909024 | Up |
| 64656 | Mrps23 | 0.551870129 | Up |
| 232087 | Mat2a | 0.551664066 | Up |
| 217869 | Eif5 | 0.551630047 | Up |
| 14155 | Fem1b | 0.551581421 | Up |
| 19899 | Rpl18 | 0.550314468 | Up |
| 59054 | Mrps30 | 0.550202135 | Up |
| 100039731 | Rpl28 | 0.550102699 | Up |
| 107260 | Otub1 | 0.549562967 | Up |
| 50772 | Mapk6 | 0.549277905 | Up |
| 21899 | Tlr6 | 0.548283895 | Up |
| 20088 | Rps24 | 0.548272783 | Up |
| 13681 | Eif4a1 | 0.548199142 | Up |
| 56176 | Pigp | 0.547310532 | Up |
| 104458 | Rars | 0.547261513 | Up |
| 232491 | Pyroxd1 | 0.546887964 | Up |
| 230721 | Pabpc4 | 0.546883546 | Up |
| 20085 | Rps19 | 0.546638269 | Up |
| 66242 | Mrps16 | 0.54599052 | Up |
| 27407 | Abcf2 | 0.5459486 | Up |
| 80291 | Rilpl2 | 0.545930544 | Up |
| 225160 | Thoc1 | 0.545914264 | Up |
| 66614 | Gpatch4 | 0.545621087 | Up |
| 100217418 | AK009175 | 0.545345774 | Up |
| 217715 | Eif2b2 | 0.545319888 | Up |

Example 23

Selection of Off-Target Genes as Sentinel Genes

Any off-target gene that demonstrates a correlation between up regulation or down regulation and an increase in ALT or some other value predictive of toxicity may be selected for for in vitro validation. In certain embodiments, a single gene that demonstrates correlation between down regulation and ALT increase may be selected for in vitro validation. In certain embodiments, a single gene that demonstrates correlation between up regulation and ALT increase may be selected for in vitro validation. In certain embodiments, a gene from Table 20 that demonstrates correlation between down regulation and ALT increase may be selected for in vitro validation. In certain embodiments, a single gene from Table 21 that demonstrates correlation between up regulation and ALT increase may be selected for in vitro validation. In certain embodiments, one or more genes from Table 20 that demonstrates a correlation between down regulation and ALT increase may be selected for in vitro validation. In certain embodiments, one or more genes from Table 21 that demonstrates a correlation between up regulation and ALT increase may be selected for in vitro validation. In certain embodiments, one or more genes from Table 20 and one or more genes from Table 21 that demonstrate a correlation between modulation and ALT increase may be selected for in vitro validation.

After identifying a sub-set of off-target genes, in vitro cells may be used to validate the sub-set of off-target genes. For example, in vitro cells may be used to validate the off-target genes shown in Table 20. For example, in vitro cells may be used to validate the off-target genes shown in Table 21.

To validate any of the off-target genes in Table 20 or Table 21, primary hepatocytes from male Balb/c mice are isolated. The isolated hepatocytes are electroporated with water or any compound that produced an increase in ALT levels of greater than 1000 IU. At 2.5 hours after electroporation, the cells can then be refed with 100 µM of warm growth medium. At 16 hours after electroporation, the cells are washed and lysed with RLT+BME. The cells are shaken for 1 minute before sealing and freesing at −80° C. Lysate is used to purify the cells for RT-PCR analysis. Genes may be measured by RT-PCR and Ribogreen and UV are read for each sample.

After obtaining the RT-PCR analysis of off-target genes that demonstrated strong amounts of modulation of amount or activity in vivo, the off-target genes that also show strong amounts of modulation of amount or activity in vitro may now be identified. For example, if one of the off-target genes shows a strong amount of down regulation in vivo upon the administration of a given oligonucleotide, and also demonstrates a strong amount of down regulation in vitro when administered the same oligonucleotide, then this off-target gene may be identified as a good indicator of toxicity (e.g. sentinel gene). In the future, one could then administer a cell any number of different oligonucleotides having any number of motifs and modifications, and then monitor the regulation of the identified off-target gene by RT-PCR or any other suitable method known to those having skill in the art. In this manner the in vivo toxicity of any number of different oligonucleotides having any number of motifs and modifications, may be identified.

Example 24

Median Length of mRNA Transcripts

Data from the whole genome expression in Example 21 was analyzed. Each down regulated gene was ranked according to its mRNA length. Each unchanged gene was ranked according to its mRNA length. Each up regulated gene was ranked according to its mRNA length. The median length of each down regulated gene's mRNA, unchanged gene's mRNA, and up regulated gene's mRNA was then calculated. The results are presented below in Table 22.

TABLE 22

Median Length of mRNA Transcripts

| Modulation | Median Length |
|---|---|
| Down Regulated | 3962 |
| Unchanged | 2652 |
| Up Regulated | 1879 |

Example 25

Median Length of Pre-mRNA Transcripts

Data from the whole genome expression in Example 21 was analyzed. Each down regulated gene was ranked according to its pre-mRNA length. Each unchanged gene was ranked according to its pre-mRNA length. Each up regulated gene was ranked according to its pre-mRNA length. The median length of each down regulated gene's pre-mRNA, unchanged gene's pre-mRNA, and up regulated gene's pre-mRNA was then calculated. The results are presented below in Table 23.

TABLE 23

Median Length of Pre-mRNA Transcripts

| Modulation | Median Length |
|---|---|
| Down Regulated | 176442 |
| Unchanged | 19862 |
| Up Regulated | 7673 |

Example 26

Combined Effects of Sentinel Genes

Six off-target genes, the modulation of which correlate strongly to ALT and/or AST increases were selected: RAPTOR, FTO, PPP3CA, PTPRK, IQGAP2, and ADK. These genes were identified as sentinel genes. Six 5-10-5 MOE gapmers with phosphorothioate backbones were then designed. Each 5-10-5 MOE gapmer targeted a different sentinel gene. For example, the RAPTOR 5-10-5 MOE gapmer would target and knock down the RAPTOR gene. For example, the FTO 5-10-5 MOE gapmer would target and knock down the FTO gene. For example, the PPP3CA 5-10-5 MOE gapmer would target and knock down the PPP3CA gene. For example, the PTPRK 5-10-5 MOE gapmer would target and knock down the PTPRK gene. For example, the IQGAP2 5-10-5 MOE gapmer would target and knock down the IQGAP2 gene. For example, the ADK 5-10-5 MOE gapmer would target and knock down the ADK gene. Balb/c mice were then separated into groups of 4 mice. Each group of mice was then given a subcutaneous 50 mg/kg dose seven times every other day of the various 5-10-5 MOE gapmers as illustrated in Table 24 below. Mice were then bled at 24 hours after every other dose and a necropsy was performed 48 hours after the last dose. ALT was then measured. Isis No.: 104838 is a 5-10-5 MOE gapmer that does not match a mouse target and was used to ensure that the mice received standardized doses of gapmers. This example shows that the modulation of combinations of sentinel genes may correlate to higher increases ALT levels as compared to increases in ALT levels associated with the modulation of singular sentinel genes.

TABLE 24

Combined Effects of Sentinel Genes

| ASO (mg/kg) | | | | | | | ALT (IU/mL) | |
|---|---|---|---|---|---|---|---|---|
| RAPTOR | FTO | PPP3CA | PTPRK | IQGAP2 | ADK | 104838 | Mean | Std. Dev |
| 0 | 0 | 0 | 0 | 0 | 0 | 0 | 27.6 | 12.5 |
| 0 | 0 | 0 | 0 | 0 | 0 | 200 | 77 | 8.8 |
| 0 | 0 | 0 | 0 | 0 | 0 | 300 | 131.8 | 20.5 |
| 0 | 0 | 0 | 0 | 0 | 50 | 0 | 40.5 | 10 |
| 0 | 0 | 0 | 0 | 50 | 0 | 0 | 50.8 | 8.7 |
| 0 | 0 | 0 | 50 | 0 | 0 | 150 | 103.3 | 11.2 |
| 0 | 0 | 50 | 0 | 0 | 0 | 150 | 44.3 | 8.7 |
| 0 | 0 | 50 | 50 | 50 | 50 | 100 | 201.5 | 23.7 |
| 0 | 50 | 0 | 0 | 0 | 0 | 150 | 46.5 | 8.1 |
| 0 | 50 | 0 | 50 | 50 | 50 | 100 | 199.3 | 82.8 |
| 0 | 50 | 50 | 0 | 50 | 50 | 100 | 127.5 | 28.8 |
| 0 | 50 | 50 | 50 | 0 | 50 | 100 | 179 | 101.1 |
| 0 | 50 | 50 | 50 | 50 | 0 | 100 | 210.5 | 32.4 |
| 0 | 50 | 50 | 50 | 50 | 50 | 50 | 170.8 | 48.3 |
| 50 | 0 | 0 | 0 | 0 | 0 | 150 | 125.5 | 8.1 |
| 50 | 0 | 0 | 50 | 50 | 50 | 100 | 276.8 | 54.9 |
| 50 | 0 | 50 | 0 | 50 | 50 | 100 | 498.3 | 61 |
| 50 | 0 | 50 | 50 | 0 | 50 | 100 | 323.5 | 82 |
| 50 | 0 | 50 | 50 | 50 | 0 | 100 | 247 | 47.5 |
| 50 | 0 | 50 | 50 | 50 | 50 | 50 | 300.5 | 109.8 |
| 50 | 50 | 0 | 0 | 50 | 50 | 100 | 546.5 | 394 |
| 50 | 50 | 0 | 50 | 0 | 0 | 50 | 378.3 | 144.5 |
| 50 | 50 | 0 | 50 | 0 | 50 | 100 | 386.3 | 91.2 |
| 50 | 50 | 0 | 50 | 50 | 0 | 100 | 402.8 | 119.2 |
| 50 | 50 | 0 | 50 | 50 | 50 | 50 | 361.5 | 73.3 |
| 50 | 50 | 50 | 0 | 0 | 50 | 100 | 354.8 | 95.3 |
| 50 | 50 | 50 | 0 | 50 | 0 | 100 | 553 | 178.7 |
| 50 | 50 | 50 | 0 | 50 | 50 | 50 | 851.5 | 32.3 |

TABLE 24-continued

| Combined Effects of Sentinel Genes | | | | | | | | |
|---|---|---|---|---|---|---|---|---|
| ASO (mg/kg) | | | | | | | ALT (IU/mL) | |
| RAPTOR | FTO | PPP3CA | PTPRK | IQGAP2 | ADK | 104838 | Mean | Std. Dev |
| 50 | 50 | 50 | 50 | 0 | 0 | 100 | 785 | 286.3 |
| 50 | 50 | 50 | 50 | 0 | 0 | 0 | 929.3 | 100 |
| 50 | 50 | 50 | 50 | 0 | 50 | 50 | 801.3 | 237.6 |
| 50 | 50 | 50 | 50 | 50 | 0 | 50 | 1169.3 | 257.8 |
| 50 | 50 | 50 | 50 | 50 | 50 | 0 | 458.3 | 73.8 |

I claim:

1. A method of predicting the in vivo toxicity of an oligomeric compound comprising:
   contacting a cell in vitro with the oligomeric compound; and measuring the modulation of the amount of at least two transcripts encoded by sentinel genes, wherein one of the at least two sentinel genes is protein phosphatase 3, catalytic subunit, alpha isoform (Ppp3ca);
   wherein the oligomeric compound is not targeted to any of the at least two sentinel gene transcripts, and wherein the modulation of the amount of the at least two sentinel gene transcripts correlates with toxicity of the oligomeric compound in vivo.

2. The method of claim 1, wherein one of the at least two sentinel genes is regulatory associated protein of MTOR, complex 1 (RAPTOR).

3. The method of claim 1, wherein one of the at least two sentinel genes is fat mass and obesity associated (Fto).

4. The method of claim 1, wherein one of the at least two sentinel genes is Ptprk.

5. The method of claim 1, wherein one of the at least two sentinel genes is Iqgap2.

6. The method of claim 1, wherein one of the at least two sentinel genes is Fars2.

7. The method of claim 1, wherein the amount of the at least two sentinel gene transcripts is reduced.

8. The method of claim 1, wherein the oligomeric compound comprises a gapmer oligonucleotide consisting of 10 to 30 linked nucleosides, wherein the gapmer oligonucleotide has a 5' wing region positioned at the 5' end of a deoxynucleotide gap, and a 3' wing region positioned at the 3' end of the deoxynucleotide gap.

9. The method of claim 8, wherein each of the wing regions is between about 1 to about 7 nucleotides in length.

10. The method of claim 8, wherein each of the wing regions is between about 1 to about 3 nucleotides in length.

11. The method of claim 8, wherein the deoxy gap region is between about 7 to about 18 nucleotides in length.

12. The method of claim 8, wherein the deoxy gap region is between about 7 to about 10 nucleotides in length.

13. The method of claim 8, wherein the oligomeric compound comprises at least one modified nucleoside.

14. The method of claim 13, wherein the modified nucleoside is a bicyclic modified nucleoside.

15. The method of claim 14, wherein the bicyclic modified nucleoside is an LNA nucleoside.

16. The method of claim 14, wherein the bicyclic modified nucleoside is a cEt nucleoside.

17. The method of claim 13, wherein the modified nucleoside is a 2'-modified nucleoside, wherein the 2'-modified nucleoside is substituted at the 2' position with a substituted or unsubstituted O-alkyl or substituted or unsubstituted O-(2-acetylamide), wherein the non-bicyclic 2'-modified nucleoside comprises a 2'-OCH$_3$, 2'-O(CH$_2$)$_2$OCH$_3$, or 2'-OCH$_2$C(O)—NR$_1$R$_2$, wherein R$_1$ and R$_2$ are independently hydrogen or substituted or unsubstituted alkyl or, in the alternative, are taken together to make a heterocyclic moiety.

18. The method of claim 1, wherein the modulation of the amount of a transcript encoded by Ppp3ca and one or more transcripts encoded by adenosine kinase (Adk), Fto, IQ motif containing GTPase activating protein 2 (Iqgap2), protein tyrosine phosphatase, receptor type, K (Ptprk), and/or RAPTOR is measured.

* * * * *

SEQUENCE LISTING

<160> NUMBER OF SEQ ID NOS: 19

<210> SEQ ID NO 1
<211> LENGTH: 3160
<212> TYPE: DNA
<213> ORGANISM: Homo sapiens

<400> SEQUENCE: 1

```
cctcccctcg cccggcgcgg tcccgtccgc ctctcgctcg cctcccgcct cccctcggtc      60
ttccgaggcg cccgggctcc cggcgcggcg gcggaggggg cgggcaggcc ggcgggcggt     120
gatgtggcag gactctttat gcgctgcggc aggatacgcg ctcggcgctg ggacgcgact     180
gcgctcagtt ctctcctctc ggaagctgca gccatgatgg aagtttgaga gttgagccgc     240
tgtgaggcga ggccgggctc aggcgaggga gatgagagac ggcggcggcc gcggcccgga     300 gccccctctca gcgcctgtga gcagccgcgg gggcagcgcc ctcggggagc cggccggcct     360
gcggcggcgg cagcggcggc gtttctcgcc tcctcttcgt cttttctaac cgtgcagcct     420
cttcctcggc ttctcctgaa agggaaggtg gaagccgtgg gctcgggcgg gagccggctg     480
aggcgcggcg gcggcggcgg cggcacctcc cgctcctgga gcggggggga gaagcggcgg     540
cggcggcggc cgcggcggct gcagctccag ggaggggggtc tgagtcgcct gtcaccattt     600
ccagggctgg gaacgccgga gagttggtct ctcccctctct actgcctcca acacggcggc     660
ggcggcggcg gcacatccag ggacccgggc cggttttaaa cctcccgtcc gccgccgccg     720 cacccccccgt ggcccgggct ccggaggccg ccggcggagg cagccgttcg gaggattatt     780
cgtcttctcc ccattccgct gccgccgctg ccaggcctct ggctgctgag gagaagcagg     840
cccagtcgct gcaaccatcc agcagccgcc gcagcagcca ttacccggct gcggtccaga     900
gccaagcggc ggcagagcga ggggcatcag ctaccgccaa gtccagagcc atttccatcc     960
tgcagaagaa gcccgccac cagcagcttc tgccatctct ctcctccttt ttcttcagcc    1020
acaggctccc agacatgaca gccatcatca aagagatcgt tagcagaaac aaaaggagat    1080
atcaagagga tggattcgac ttagacttga cctatattta tccaaacatt attgctatgg    1140
gatttcctgc agaaagactt gaaggcgtat acaggaacaa tattgatgat gtagtaaggt    1200
ttttggattc aaagcataaa aaccattaca agatatacaa tctttgtgct gaaagacatt    1260
atgacaccgc caaatttaat tgcagagttg cacaatatcc ttttgaagac cataacccac    1320
cacagctaga acttatcaaa cccttttgtg aagatcttga ccaatggcta agtgaagatg    1380
acaatcatgt tgcagcaatt cactgtaaag ctggaaaggg acgaactggt gtaatgatat    1440
gtgcatattt attacatcgg ggcaaatttt taaaggcaca agaggccta gatttctatg    1500 gggaagtaag gaccagagac aaaaagggag taactattcc cagtcagagg cgctatgtgt    1560
```

| | |
|---|---|
| attattatag ctacctgtta aagaatcatc tggattatag accagtggca ctgttgtttc | 1620 |
| acaagatgat gtttgaaact attccaatgt tcagtggcgg aacttgcaat cctcagtttg | 1680 |
| tggtctgcca gctaaaggtg aagatatatt cctccaattc aggacccaca cgacgggaag | 1740 |
| acaagttcat gtactttgag ttccctcagc cgttacctgt gtgtggtgat atcaaagtag | 1800 |
| agttcttcca caaacagaac aagatgctaa aaaaggacaa aatgtttcac ttttgggtaa | 1860 |
| atacattctt cataccagga ccagaggaaa cctcagaaaa agtagaaaat ggaagtctat | 1920 |
| gtgatcaaga aatcgatagc atttgcagta tagagcgtgc agataatgac aaggaatatc | 1980 |
| tagtacttac tttaacaaaa aatgatcttg acaaagcaaa taaagacaaa gccaaccgat | 2040 |
| acttttctcc aaattttaag gtgaagctgt acttcacaaa aacagtagag gagccgtcaa | 2100 |
| atccagaggc tagcagttca acttctgtaa caccagatgt tagtgacaat gaacctgatc | 2160 |
| attatagata ttctgacacc actgactctg atccagagaa tgaaccttt gatgaagatc | 2220 |
| agcatacaca aattacaaaa gtctgaattt ttttttatca agagggataa aacaccatga | 2280 |
| aaataaactt gaataaactg aaaatggacc tttttttttt taatggcaat aggacattgt | 2340 |
| gtcagattac cagttatagg aacaattctc ttttcctgac caatcttgtt ttaccctata | 2400 |
| catccacagg gttttgacac ttgttgtcca gttgaaaaaa ggttgtgtag ctgtgtcatg | 2460 |
| tataccctt tttgtgtcaa aaggacattt aaaattcaat taggattaat aaagatggca | 2520 |
| cttccccgtt ttattccagt tttataaaaa gtggagacag actgatgtgt atacgtagga | 2580 |
| atttttcct tttgtgttct gtcaccaact gaagtggcta aagagctttg tgatatactg | 2640 |
| gttcacatcc tacccctttg cacttgtggc aacagataag tttgcagttg gctaagagag | 2700 |
| gtttccgaaa ggttttgcta ccattctaat gcatgtattc gggttagggc aatggagggg | 2760 |
| aatgctcaga aaggaaataa tttatgctg gactctggac catataccat ctccagctat | 2820 |
| ttacacacac ctttctttag catgctacag ttattaatct ggacattcga ggaattggcc | 2880 |
| gctgtcactg cttgttgttt gcgcattttt ttttaaagca tattggtgct agaaaaggca | 2940 |
| gctaaaggaa gtgaatctgt attggggtac aggaatgaac cttctgcaac atcttaagat | 3000 |
| ccacaaatga agggatataa aaataatgtc ataggtaaga aacacagcaa caatgactta | 3060 |
| accatataaa tgtggaggct atcaacaaag aatgggcttg aaacattata aaaattgaca | 3120 |
| atgatttatt aaatatgttt tctcaattgt aaaaaaaaaa | 3160 |

<210> SEQ ID NO 2
<211> LENGTH: 26
<212> TYPE: DNA
<213> ORGANISM: Artificial sequence
<220> FEATURE:
<223> OTHER INFORMATION: Primer

<400> SEQUENCE: 2
aatggctaag tgaagatgac aatcat                                     26

<210> SEQ ID NO 3
<211> LENGTH: 25
<212> TYPE: DNA
<213> ORGANISM: Artificial sequence
<220> FEATURE:
<223> OTHER INFORMATION: Primer

<400> SEQUENCE: 3
tgcacatatc attacaccag ttcgt                                      25

```
<210> SEQ ID NO 4
<211> LENGTH: 30
<212> TYPE: DNA
<213> ORGANISM: Artificial sequence
<220> FEATURE:
<223> OTHER INFORMATION: Probe

<400> SEQUENCE: 4
ttgcagcaat tcactgtaaa gctggaaagg                                   30

<210> SEQ ID NO 5
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 5
cctggtgtac accc                                                    14

<210> SEQ ID NO 6
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 6
ggtccctgca gtac                                                    14

<210> SEQ ID NO 7
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 7
gacgcgcctg aaggtt                                                  16

<210> SEQ ID NO 8
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 8
cagatatagg actgga                                                  16

<210> SEQ ID NO 9
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 9
atccagagat gcctcc                                                  16

<210> SEQ ID NO 10
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 10
ggccaccacg ctgtca                                                     16

<210> SEQ ID NO 11
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 11
tgccaccgta gacacg                                                     16

<210> SEQ ID NO 12
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 12
ggacacattg gccaca                                                     16

<210> SEQ ID NO 13
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 13
ccctggtgta cacccc                                                     16

<210> SEQ ID NO 14
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 14
atcatggctg cagctt                                                     16

<210> SEQ ID NO 15
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 15
tggtccctgc agtact                                                     16

<210> SEQ ID NO 16
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 16
gtctgtgcat ctctcc                                                     16

<210> SEQ ID NO 17
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 17
gtcagtatcc cagtgt                                                      16

<210> SEQ ID NO 18
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 18
tgaggtcctg cactgg                                                      16

<210> SEQ ID NO 19
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 19
ctcaatccat ggcagc                                                      16
```